United States Patent
Helm et al.

(10) Patent No.: US 12,412,297 B2
(45) Date of Patent: Sep. 9, 2025

(54) SYSTEM AND METHOD FOR IDENTIFYING AND CLASSIFYING A FEATURE IN AN IMAGE OF A SUBJECT

(71) Applicants: Medtronic Navigation, Inc., Louisville, CO (US); The Johns Hopkins University, Baltimore, MD (US)

(72) Inventors: Patrick A. Helm, Canton, MA (US); Jeffrey H. Siewerdsen, Baltimore, MD (US); Ali Uneri, Columbia, MD (US); Craig K. Jones, Reisterstown, MD (US); Yixuan Huang, Baltimore, MD (US); Xiaoxuan Zhang, Baltimore, MD (US)

(73) Assignees: Medtronic Navigation, Inc., Lafayette, CO (US); The Johns Hopkins University, Baltimore, MD (US)

( * ) Notice: Subject to any disclaimer, the term of this patent is extended or adjusted under 35 U.S.C. 154(b) by 296 days.

(21) Appl. No.: 17/887,649

(22) Filed: Aug. 15, 2022

(65) Prior Publication Data
US 2023/0169646 A1    Jun. 1, 2023

Related U.S. Application Data

(60) Provisional application No. 63/283,762, filed on Nov. 29, 2021.

(51) Int. Cl.
*G06T 7/73* (2017.01)
*A61B 90/00* (2016.01)
(Continued)

(52) U.S. Cl.
CPC ............... *G06T 7/73* (2017.01); *A61B 90/37* (2016.02); *G06T 5/50* (2013.01); *G06T 7/0012* (2013.01);
(Continued)

(58) Field of Classification Search
CPC ........... G06T 7/73; G06T 5/50; G06T 7/0012; G06T 7/11; G06T 7/337;
(Continued)

(56) References Cited

U.S. PATENT DOCUMENTS

| 8,238,631 B2 | 8/2012 | Hartmann et al. |
| 10,881,371 B2 | 1/2021 | Helm et al. |

(Continued)

FOREIGN PATENT DOCUMENTS

| WO | 2023096831 A1 | 6/2023 |
| WO | 2023096834 A1 | 6/2023 |

(Continued)

OTHER PUBLICATIONS

Schmidt, S., Kappes, J., Bergtholdt, M., Pekar, V., Dries, S., Bystrov, D. and Schnorr., C., "Spine Detection and Labeling Using a Parts-Based Graphical Model," Bienn. Int. Conf. Inf. Process. Med. Imaging, 122-133 (2007).

(Continued)

*Primary Examiner* — Juan M Guillermety

(57) ABSTRACT

A method and system is disclosed for analyzing image data of a subject. The image data can be collected with an imaging system in a selected manner and/or motion. The image data may include selected overlap and be acquired with an imaging system that generates a plurality of perspectives for more than one location. An automatic system and method may then define or identify various features and/or allow for registration for alternative image data.

20 Claims, 14 Drawing Sheets

(51) Int. Cl.
| | |
|---|---|
| *G06T 5/50* | (2006.01) |
| *G06T 7/00* | (2017.01) |
| *G06T 7/11* | (2017.01) |
| *G06T 7/33* | (2017.01) |
| *G06V 10/10* | (2022.01) |
| *G06V 10/22* | (2022.01) |
| *G06V 10/25* | (2022.01) |
| *G06V 10/40* | (2022.01) |
| *G06V 10/44* | (2022.01) |
| *G06V 10/764* | (2022.01) |
| *G06V 10/82* | (2022.01) |

(52) U.S. Cl.
CPC ............... *G06T 7/11* (2017.01); *G06T 7/337* (2017.01); *G06V 10/16* (2022.01); *G06V 10/22* (2022.01); *G06V 10/25* (2022.01); *G06V 10/40* (2022.01); *G06V 10/44* (2022.01); *G06V 10/764* (2022.01); *G06V 10/82* (2022.01); *A61B 2090/376* (2016.02); *G06T 2207/10116* (2013.01); *G06T 2207/20081* (2013.01); *G06T 2207/20084* (2013.01); *G06T 2207/20212* (2013.01); *G06T 2207/20221* (2013.01); *G06V 2201/03* (2022.01); *G06V 2201/07* (2022.01)

(58) Field of Classification Search
CPC . G06T 2207/10116; G06T 2207/20081; G06T 2207/20084; G06T 2207/20212; G06T 2207/20221; G06T 2207/10072; G06T 2207/30012; G06T 7/33; A61B 90/37; A61B 2090/376; G06V 10/16; G06V 10/22; G06V 10/25; G06V 10/40; G06V 10/44; G06V 10/764; G06V 10/82; G06V 2201/03; G06V 2201/07; G06V 10/143; G06V 10/454

See application file for complete search history.

(56) References Cited

U.S. PATENT DOCUMENTS

| | | | |
|---|---|---|---|
| 11,071,507 | B2 | 7/2021 | Helm et al. |
| 11,138,768 | B2 | 10/2021 | Helm et al. |
| 2010/0290690 | A1 | 11/2010 | Hartmann et al. |
| 2012/0099772 | A1 | 4/2012 | Helm et al. |
| 2012/0250822 | A1 | 10/2012 | Helm et al. |
| 2017/0231713 | A1 | 8/2017 | Siewerdsen et al. |
| 2019/0030370 | A1 | 1/2019 | Hibbard |
| 2019/0311505 | A1 | 10/2019 | Helm et al. |
| 2020/0085382 | A1* | 3/2020 | Taerum ................. G06T 7/0016 |
| 2020/0205763 | A1 | 7/2020 | Helm et al. |
| 2020/0205764 | A1 | 7/2020 | Helm et al. |
| 2021/0077047 | A1 | 3/2021 | Tolkowsky |
| 2021/0397254 | A1 | 12/2021 | Seibel et al. |
| 2022/0207722 | A1* | 6/2022 | Kim ....................... G06T 7/0012 |
| 2022/0309675 | A1 | 9/2022 | Conjeti et al. |
| 2024/0307122 | A1 | 9/2024 | Tolkowsky et al. |

FOREIGN PATENT DOCUMENTS

| | | |
|---|---|---|
| WO | 2023096835 A1 | 6/2023 |
| WO | 2023096836 A1 | 6/2023 |

OTHER PUBLICATIONS

Uneri, A., De Silva, T., Stayman, J. W., Kleinszig, G., Vogt, S., Khanna, A. J., Gokaslan, Z. L., Wolinsky, J. P. and Siewerdsen, J. H., "Known-component 3D-2D registration for quality assurance of spine surgery pedicle screw placement," Phys. Med. Biol. 60(20), 8007-8024 (2015).

Weinstein, S. L., Dolan, L. A., Cheng, J. C. Y., Danielsson, A. and Morcuende, J. A., "Adolescent idiopathic scoliosis Stuart," Lancet 371, 1527-1537 (2008).
Murphy, R. F. and Mooney, J. F., "Complications following spine fusion for adolescent idiopathic scoliosis," Curr. Rev. Musculoskelet. Med. 9(4), 462-469 (2016).
Tonetti, J., Boudissa, M., Kerschbaumer, G. and Seurat, O., "Role of 3D intraoperative imaging in orthopedic and trauma surgery," Orthop. Traumatol. Surg. Res. 106(1), S19-S25 (2020).
Penney, G. P., Little, J. A., Weese, J., Hill, D. L. G. and Hawkes, D. J., "Deforming a Preoperative Volume to Represent the Intraoperative Scene," Comput. Aided Surg. 7(2), 63-73 (2002).
Park, S., Plishker, W., Quon, H., Wong, J., Shekhar, R. and Lee, J., "Deformable registration of CT and cone-beam CT with local intensity matching," Phys. Med. Biol. 62(3), 927-947 (2017).
Sharp, G. C., Kandasamy, N., Singh, H. and Folkert, M., "GPU-based streaming architectures for fast cone-beam CT image reconstruction and demons deformable registration," Phys. Med. Biol. 52(19), 5771-5783 (2007).
Nithiananthan, S., Schafer, S., Uneri, A., Mirota, D. J., Stayman, J. W., Zbijewski, W., Brock, K. K., Daly, M. J., Chan, H., Irish, J. C. and Siewerdsen, J. H., "Demons deformable registration of CT and cone-beam CT using an iterative intensity matching approach," Med. Phys. 38(4), 1785-1798 (2011).
Pei, Y., Zhang, Y., Qin, H., Ma, G., Guo, Y., Xu, T. and Zha, H., "Non-rigid Craniofacial 2D-3D Registration Using CNN-Based Regression," Int. Work. Deep Learn. Med. Image Anal., 117-125 (2017).
Miao, S., Wang, Z. J. and Liao, R., "A CNN Regression Approach for Real-Time 2D/3D Registration," IEEE Trans. Med. Imaging 35(5), 1352-1363 (2016).
Luckner, C., Herbst, M., Weber, T., Beister, M., Ritschl, L., Kappler, S. and Maier, A., "High-speed slot-scanning radiography using small-angle tomosynthesis: Investigation of spatial resolution," Med. Phys. 46(12), 5454-5466 (2019).
Uneri, A., Zhang, X., Yi, T., Stayman, J. W., Helm, P. A., Theodore, N. and Siewerdsen, J. H., "Image quality and dose characteristics for an O-arm intraoperative imagingsystem with model-based image reconstruction," Med. Phys. 45(11), 4857-4868 (2018).
Otake, Y., Wang, A. S., Webster Stayman, J., Uneri, A., Kleinszig, G., Vogt, S., Khanna, A. J., Gokaslan, Z. L. and Siewerdsen, J. H., "Robust 3D-2D image registration: application to spine interventions and vertebral labeling in the presence of anatomical deformation.," Phys. Med. Biol. 58(23), 8535-8553 (2013).
Uneri, A., Zhang, X., Siewerdsen, J. H., Theodore, N., Helm, P. A., Stayman, J. W. and Osgood, G. M., "3D-2D image registration in virtual long-film imaging: application to spinal deformity correction," 52 (2019).
Penney, G. P., Weese, J., Little, J. a, Desmedt, P., Hill, D. L. and Hawkes, D. J., "A comparison of similarity measures for use in 2-D-3-D medical image registration.," IEEE Trans. Med. Imaging 17(4), 586-595 (1998).
Uneri, A., Goerres, J., Silva, T. De, Jacobson, M. W., Ketcha, M. D., Reaungamornrat, S., Kleinszig, G., Vogt, S., Khanna, A. J., Wolinsky, J. P. and Siewerdsen, J. H., "Deformable 3D-2D registration of known components for image guidance in spine surgery," Med. Image Comput. Comput. Interv. 990, 124-132 (2016).
Uneri, A., Wu, P., Jones, C. K., Ketcha, M. D., Vagdargi, P., Han, R., Helm, P. A., Luciano, M., Anderson, W. S. and Siewerdsen, J. H., "Data-driven deformable 3D-2D registration for guiding neuroelectrode placement in deep brain stimulation," 44 (2021).
Otake, Y., Wang, A. S., Uneri, A., Kleinszig, G., Vogt, S., Aygun, N., Sheng-fu, L. L., Wolinsky, J.-P., Gokaslan, Z. L. and Siewerdsen, J. H., "3D-2D registration in mobile radiographs: algorithm development and preliminary clinical evaluation," Phys. Med. Biol. 60(5), 2075 (2015).
Rampersaud, Y. R., Simon, D. A. and Foley, K. T., "Accuracy requirements for image-guided spinal pedicle screw placement," Spine (Phila. Pa. 1976). 26(4), 352-359 (2001).
Ren, S., He, K., Girshick, R. and Sun, J., "Faster R-CNN: Towards Real-Time Object Detection with Region Proposal Networks," IEEE Trans. Pattern Anal. Mach. Intell. 39(6), 1137-1149 (2017).

(56) References Cited

OTHER PUBLICATIONS

Nguyen, N. T., Tran, D. Q., Nguyen, N. T., & Nguyen, H. Q. (2020). A CNN-LSTM Architecture for Detection of Intracranial Hemorrhage on CT scans. arXiv preprint arXiv:2005.10992.
Pauly, O., Glocker, B., Criminisi, A., Mateus, D., Möller, A. M., Nekolla, S., & Navab, N. (Sep. 2011). Fast multiple organ detection and localization in whole-body MR Dixon sequences. In International Conference on Medical Image Computing and Computer-Assisted Intervention (pp. 239-247). Springer, Berlin, Heidelberg.
Sa, R., Owens, W., Wiegand, R., Studin, M., Capoferri, D., Barooha, K., . . . & Chaudhary, V. (Jul. 2017). Intervertebral disc detection in X-ray images using faster R-CNN. In 2017 39th Annual International Conference of the IEEE Engineering in Medicine and Biology Society (EMBC) (pp. 564-567). IEEE.
Sekuboyina, Anjany, et al. "Labeling Vertebrae with Two-dimensional Reformations of Multidetector CT Images: An Adversarial Approach for Incorporating Prior Knowledge of Spine Anatomy." Radiology: Artificial Intelligence 2.2 (2020): e190074.
Thian, Y. L., Li, Y., Jagmohan, P., Sia, D., Chan, V. E. Y., & Tan, R. T. (2019). Convolutional neural networks for automated fracture detection and localization on wrist radiographs. Radiology: Artificial Intelligence, 1(1), e180001.
Uhercík, Marián, et al. "Model fitting using RANSAC for surgical tool localization in 3-D ultrasound images." IEEE Transactions on Biomedical Engineering 57.8 (2010): 1907-1916.
Uneri A, De Silva T, Goerres J, Jacobson MW, Ketcha MD, Reaungamorrat S, Kleinszig G, Vogt S, Khanna AJ, Osgood GM, Wolinsky JP, Siewerdsen JH. Intraoperative evaluation of device placement in spine surgery using known-component 3D-2D image registration. Phys Med Biol. Apr. 21, 2017;62(8):3330-3351. doi: 10.1088/1361-6560/aa62c5. Epub Feb. 24, 2017. PMID: 28233760; PMCID: PMC5901722.
Luo, X., Pu, Z., Xu, Y., Wong, W. Y., Su, J., Dou, X., Ye, B., Hu, J., & Mou, L. (2021). MVDRNet: Multi-view diabetic retinopathy detection by combining DCNNs and attention mechanisms. Pattern Recognition, 120, 108104. https://doi.org/10.1016/j.patcog.2021.108104.
Ma, J., Li, X., Li, H., Wang, R., Menze, B. H., & Zheng, W. (2021). Cross-View Relation Networks for Mammogram Mass Detection. International Conference on Pattern Recognition. https://doi.org/10.1109/icpr48806.2021.9413132.
Manbachi, A., De Silva, T., Uneri, A., Jacobson, M. P., Goerres, J., Ketcha, M. D., Han, R., Aygun, N., Thompson, D. R., Ye, X., Vogt, S., Kleinszig, G., Molina, C. A., Iyer, R. R., Garzon-Muvdi, T., Raber, M., Groves, M. L., Wolinsky, J. P., & Siewerdsen, J. H. (2018). Clinical Translation of the LevelCheck Decision Support Algorithm for Target Localization in Spine Surgery. Annals of Biomedical Engineering, 46(10), 1548-1557. https://doi.org/10.1007/s10439-018-2099-2.
Mody, M. G., Nourbakhsh, A., Stahl, D. L., Gibbs, M., Alfawareh, M., & Garges, K. J. (2008). The Prevalence of Wrong Level Surgery Among Spine Surgeons. Spine, 33(2), 194-198. https://doi.org/10.1097/brs.0b013e31816043d1.
Nakai, S., Yoshizawa, H., & Kobayashi, S. (1999). Long-Term Follow-Up Study of Posterior Lumbar Interbody Fusion. Journal of Spinal Disorders, 12(4), 293???299. https://doi.org/10.1097/00002517-199908000-00004.
Panjabi, M. M., Duranceau, J., Goel, V. K., Oxland, T. R., & Takata, K. (1991). Cervical Human Vertebrae Quantitative Three-Dimensional Anatomy of the Middle and Lower Regions. Spine, 16(8), 861-869. https://doi.org/10.1097/00007632-199108000-00001.
Panjabi, M. M., Takata, K., Goel, V. K., Federico, D. J., Oxland, T. R., Duranceau, J., & Krag, M. H. (1991). Thoracic Human Vertebrae Quantitative Three-Dimensional Anatomy. Spine, 16(8), 888-901. https://doi.org/10.1097/00007632-199108000-00006.
Panjabi, M. M., Goel, V. K., Oxland, T. R., Takata, K., Duranceau, J., Krag, M. H., & Price, M. (1992). Human Lumbar Vertebrae. Spine, 17(3), 299-306. https://doi.org/10.1097/00007632-199203000-00010.

Qin, C., Yao, D., Zhuang, H. R., Wang, H., Shi, Y., & Song, Z. (2019). Residual Block-based Multi-Label Classification and Localization Network with Integral Regression for Vertebrae Labeling. ArXiv (Cornell University). https://doi.org/10.48550/arxiv.2001.00170.
Rasoulian, A., Rohling, R., & Abolmaesumi, P. (2013). Lumbar Spine Segmentation Using a Statistical Multi-Vertebrae Anatomical Shape+Pose Model. IEEE Transactions on Medical Imaging, 32(10), 1890-1900. https://doi.org/10.1109/tmi.2013.2268424.
Rubin, J. M., Sanghavi, D., Claire, Z., Lee, K. L., Qadir, A., & Xu-Wilson, M. (2018). Large Scale Automated Reading of Frontal and Lateral Chest X-Rays using Dual Convolutional Neural Networks. ArXiv: Computer Vision and Pattern Recognition. http://export.arxiv.org/pdf/1804.07839.
Scholtz, J., Wichmann, J. L., Kaup, M., Fischer, S., Kerl, J. M., Lehnert, T., Vogl, T. J., & Bauer, R. W. (2015). First performance evaluation of software for automatic segmentation, labeling and reformation of anatomical aligned axial images of the thoracolumbar spine at CT. European Journal of Radiology, 84(3), 437-442. https://doi.org/10.1016/j.ejrad.2014.11.043.
Takami, M., Taiji, R., Tsutsui, S., Iwasaki, H., Okada, M., Minamide, A., Yukawa, Y., Hashizume, H., & Yamada, H. (2021). Impact of an intraoperative coronal spinal alignment measurement technique using a navigational tool for a 3D spinal rod bending system in adult spinal deformity cases. Journal of Neurosurgery, 36(1), 62-70. https://doi.org/10.3171/2021.3.spine201856.
Tran, V. H., Lin, H., & Liu, H. (2020). MBNet: A Multi-task Deep Neural Network for Semantic Segmentation and Lumbar Vertebra Inspection on X-Ray Images. Lecture Notes in Computer Science, 635-651. https://doi.org/10.1007/978-3-030-69541-5_38.
Van Tulder, G., Tong, Y., & Marchiori, E. (2021). Multi-view Analysis of Unregistered Medical Images Using Cross-View Transformers. Lecture Notes in Computer Science, 104-113. https://doi.org/10.1007/978-3-030-87199-4_10.
Uneri, A., Wang, S. A., Otake, Y., Kleinszig, G., Teske, J., Khanna, A. J., Gallia, G. L., Gokaslan, Z. L., & Siewerdsen, J. H. (2014). Evaluation of low-dose limits in 3D-2D rigid registration for surgical guidance. Physics in Medicine and Biology, 59(18), 5329-5345. https://doi.org/10.1088/0031-9155/59/18/5329.
Vaynrub, M., Hirsch, B. E., Tishelman, J. C., Vasquez-Montes, D., Buckland, A. J., Errico, T. J., & Protopsaltis, T. S. (2018). Validation of prone intraoperative measurements of global spinal alignment. Journal of Neurosurgery, 29(2), 187-192. https://doi.org/10.3171/2018.1.spine17808.
Wang, F., Zheng, K., Lu, L., Xiao, J., Wu, M., & Miao, S. (2021). Automatic Vertebra Localization and Identification in CT by Spine Rectification and Anatomically-constrained Optimization. Computer Vision and Pattern Recognition. https://doi.org/10.1109/cvpr46437.2021.00524.
Wang, L., Xu, Q., Leung, S., Chung, J. H., Chen, B., & Li, S. (2019). Accurate automated Cobb angles estimation using multi-view extrapolation net. Medical Image Analysis, 58, 101542. https://doi.org/10.1016/j.media.2019.101542.
Wang, L., Traub, J., Heining, S. M., Benhimane, S., Euler, E., Graumann, R., & Navab, N. (2008). Long Bone X-Ray Image Stitching Using Camera Augmented Mobile C-Arm. Lecture Notes in Computer Science, 578-586. https://doi.org/10.1007/978-3-540-85990-1_69.
Watanabe, K., Aoki, Y., & Matsumoto, M. (2019). An Application of Artificial Intelligence to Diagnostic Imaging of Spine Disease: Estimating Spinal Alignment From Moire Images. Neurospine, 16(4), 697-702. https://doi.org/10.14245/ns.1938426.213.
Weng, C., Wang, T., Huang, Y., Yeh, Y., Fu, C., Yeh, C., & Tsai, T. (2019). Artificial Intelligence for Automatic Measurement of Sagittal Vertical Axis Using ResUNet Framework. Journal of Clinical Medicine, 8(11), 1826. https://doi.org/10.3390/jcm8111826.
International Preliminary Report on Patentability related to International Application No. PCT/US2022/050406 dated May 2, 2024, 13 pages.
International Preliminary Report on Patentability related to International Application No. PCT/US2022/050422 dated May 2, 2024, 12 pages.

(56) References Cited

OTHER PUBLICATIONS

International Preliminary Report on Patentability related to International Application No. PCT/US2022/050414 dated May 2, 2024, 14 pages.

International Preliminary Report on Patentability related to International Application No. PCT/US2022/050400 dated May 2, 2024, 15 pages.

Huang, Y., Uneri, A., Jones, C. K., Zhang, X., Ketcha, M. D., Aygun, N., Helm, P. A. and Siewerdsen, J. H., "3D vertebrae labeling in spine CT: An accurate, memory-efficient (Ortho2D) framework," Phys. Med. Biol. 66(12) (2021).

Klinder, T., Ostermann, J., Ehm, M., Franz, A., Kneser, R. and Lorenz, C., "Automated model-based vertebra detection, identification, and segmentation in CT images," Med. Image Anal. 13(3), 471-482 (2009).

Chen, Y., Gao, Y., Li, K., Zhao, L. and Zhao, J., "Vertebrae Identification and Localization Utilizing Fully Convolutional Networks and a Hidden Markov Model," IEEE Trans. Med. Imaging 39(2), 387-399 (2020).

Ailon, T., Smith, J. S., Shaffrey, C. I., Lenke, L. G., Brodke, D., Harrop, J. S., Fehlings, M. and Ames, C. P., "Degenerative spinal deformity," Neurosurgery 77(4), S75-S91 (2015).

Betz, R. R., Kim, J., D'Andrea, L. P., Mulcahey, M. J., Balsara, R. K. and Clements, D. H., "An innovative technique of vertebral body stapling for the treatment of patients with adolescent idiopathic scoliosis: A feasibility, safety, and utility study," Spine (Phila. Pa. 1976). 28(20 Suppl.), 255-265 (2003).

Diebo, B. G., Shah, N. V., Boachie-Adjei, O., Zhu, F., Rothenfluh, D. A., Paulino, C. B., Schwab, F. J. and Lafage, V., "Adult spinal deformity," Lancet 394(10193), 160-172 (2019).

Jain, A., Hassanzadeh, H., Puvanesarajah, V., Klineberg, E. O., Sciubba, D. M., Kelly, M. P., Hamilton, D. K., Lafage, V., Buckland, A. J., Passias, P. G., Protopsaltis, T. S., Lafage, R., Smith, J. S., Shaffrey, C. I. and Kebaish, K. M., "Incidence of perioperative medical complications and mortality among elderly patients undergoing surgery for spinal deformity: Analysis of 3519 patients," J. Neurosurg. Spine 27(5), 534-539 (2017).

Hu, X., Ohnmeiss, D. D. and Lieberman, I. H., "Robotic-assisted pedicle screw placement: Lessons learned from the first 102 patients," Eur. Spine J. 22(3), 661-666 (2013).

Little, J. A., Hill, D. L. G. and Hawkes, D. J., "Deformations Incorporating Rigid Structures," Comput. Vis. Image Underst. 66(2), 223-232 (1997).

Kohlrausch, J., Rohr, K. and Stiehl, H. S., "A new class of elastic body splines for nonrigid registration of medical images," J. Math. Imaging Vis. 23(3), 253-280 (2005).

Brock, K. K., Sharpe, M. B., Dawson, L. A., Kim, S. M. and Jaffray, D. A., "Accuracy of finite element model-based multi-organ deformable image registration," Med. Phys. 32(6), 1647-1659 (2005).

Gill, S., Abolmaesumi, P., Fichtinger, G., Boisvert, J., Pichora, D., Borshneck, D. and Mousavi, P., "Biomechanically constrained groupwise ultrasound to CT registration of the lumbar spine," Med. Image Anal. 16(3), 662-674 (2012).

Lawson, J. D., Schreibmann, E., Jani, A. B. and Fox, T., "Quantitative evaluation of a cone-beam computed tomography-planning computed tomography deformable image registration method for adaptive radiation therapy," J. Appl. Clin. Med. Phys. 8(4), 96-113 (2007).

Kearney, V., Haaf, S., Sudhyadhom, A., Valdes, G. and Solberg, T. D., "An unsupervised convolutional neural network-based algorithm for deformable image registration," Phys. Med. Biol. 63(18) (2018).

Eppenhof, K. A. J. and Pluim, J. P. W., "Pulmonary CT Registration Through Supervised Learning With Convolutional Neural Networks," IEEE Trans. Med. Imaging 38(5), 1097-1105 (2019).

Esfandiari, H., Newell, R., Anglin, C., Street, J. and Hodgson, A. J., "A deep learning framework for segmentation and pose estimation of pedicle screw implants based on C-arm fluoroscopy," Int. J. Comput. Assist. Radiol. Surg. 13(8), 1269-1282 (2018).

Ladd, B., Jones, K. and Polly, D., "2-Dimensional Long Film O-Arm Imaging, an Alternative When Intraoperative Fluoroscopy Is Inadequate," World Neurosurg. 150, 54-55 (2021).

Ketcha, M. D., De Silva, T., Uneri, A., Jacobson, M. W., Goerres, J., Kleinszig, G., Vogt, S., Wolinsky, J. P. and Siewerdsen, J. H., "Multi-stage 3D-2D registration for correction of anatomical deformation in image-guided spine surgery," Phys. Med. Biol. 62(11), 4604 (2017).

Helm, P. A., Teichman, R., Hartmann, S. L. and Simon, D., "Spinal Navigation and Imaging: History, Trends, and Future," IEEE Trans. Med. Imaging 34(8), 1738-1746 (2015).

De Silva, T., Uneri, A., Ketcha, M. D., Reaungamornrat, S., Kleinszig, G., Vogt, S., Aygun, N., Lo, S. F., Wolinsky, J. P. and Siewerdsen, J. H., "3D-2D image registration for target localization in spine surgery: investigation of similarity metrics providing robustness to content mismatch," Phys. Med. Biol. 61(8), 3009 (2016).

Jansen, N. and Ostermeier, A., "Completely derandomized self-adaptation in evolution strategies.," Evol. Comput. 9(2), 159-195 (2001).

Ketcha, M. D., De Silva, T., Uneri, A., Jacobson, M. W., Goerres, J., Kleinszig, G., Vogt, S., Wolinsky, J. P. and Siewerdsen, J. H., "Multi-stage 3D-2D registration for correction of anatomical deformation in image-guided spine surgery," Phys. Med. Biol. 62(11), 4604-4622 (2017). *Duplicate****.

Hartley, R., Trumpf, J., Dai, Y. and Li, H., "Rotation averaging," Int. J. Comput. Vis. 103(3), 267-305 (2013).

Been, E. and Kalichman, L., "Lumbar lordosis," Spine J. 14(1), 87-97 (2014).

Johnson, H., Harris, G. and Williams, K., "BRAINSFit: mutual information rigid registrations of whole-brain 3D images, using the insight toolkit," Insight J 57(1) (2007).

Li, P., Chen, X. and Shen, S., "Stereo R-CNN based 3D Object Detection for Autonomous Driving," Proc. IEEE/CVF Conf. Comput. Vis. Pattern Recognit., 7644-7652 (2019).

Lin, T.-Y., Dollar, P., Girshick, R., He, K., Hariharan, B. and Belongie, S., "Feature Pyramid Networks for Object Detection" (2016).

Glocker, B., Feulner, J., Criminisi, A., Haynor, D. R. and Konukoglu, E., "Automatic localization and identification of vertebrae in arbitrary field-of-view CT scans," Lect. Notes Comput. Sci. (including Subser. Lect. Notes Artif. Intell. Lect. Notes Bioinformatics) 7512 LNCS, 590-598, Springer Verlag (2012).

Clark, K., Vendt, B., Smith, K., Freymann, J., Kirby, J., Koppel, P., Moore, S., Phillips, S., Maffitt, D., Pringle, M., Tarbox, L. and Prior, F., "The Cancer Imaging Archive (TCIA): Maintaining and Operating a Public Information Repository," J. Digit. Imaging 2013 266 26(6), 1045-1057 (2013).

Ketcha, M. D., De Silva, T., Han, R., Uneri, A., Vogt, S., Kleinszig, G. and Siewerdsen, J. H., "A Statistical Model for Rigid Image Registration Performance: The Influence of Soft-Tissue Deformation as a Confounding Noise Source," IEEE Trans. Med. Imaging 38(9), 2016-2027 (2019).

"A Pedestrian Detection Model Based on Binocular Information Fusion https://ieeexplore.ieee.org/document/8770601".

"Aerial Target Tracking Algorithm Based on Faster R-CNN Combined with Frame Differencing https://www.mdpi.com/2226-4310/4/2/32/pdf".

Akselrod-Ballin, A., Karlinsky, L., Alpert, S., Hasoul, S., Ben-Ari, R., & Barkan, E. (2016). A region based convolutional network for tumor detection and classification in breast mammography. In Deep learning and data labeling for medical applications (pp. 197-205). Springer, Cham.

"Automatic Localization of the Left Ventricle from Cardiac Cine Magnetic Resonance Imaging: A New Spectrum-Based Computer-Aided Tool https://www.ncbi.nlm.nih.gov/pmc/articles/PMC3982962/".

Bouget, D., Allan, M., Stoyanov, D., & Jannin, P. (2017). Vision-based and marker-less surgical tool detection and tracking: a review of the literature. Medical image analysis, 35, 633-654.

Cao, Z., Duan, L., Yang, G., Yue, T., Chen, Q., Fu, H., & Xu, Y. (Sep. 2017). Breast tumor detection in ultrasound images using deep learning. In International Workshop on Patch-based Techniques in Medical Imaging (pp. 121-128). Springer, Cham.

(56) References Cited

OTHER PUBLICATIONS

"Convolutional Neural Networks: A Binocular Vision Perspective https://arxiv.org/pdf/1912.10201v1.pdf".

Criminisi, A., Shotton, J., Robertson, D., & Konukoglu, E. (Sep. 2010). Regression forests for efficient anatomy detection and localization in CT studies. In International MICCAI Workshop on Medical Computer Vision (pp. 106-117). Springer, Berlin, Heidelberg.

"Deep Learning for Cardiac Image Segmentation: A Review https://www.frontiersin.org/articles/10.3389/fcvm.2020.00025/full".

"Deep Object Co-Segmentation https://arxiv.org/abs/1804.06423".

"Deep Sequential Segmentation of Organs in Volumetric Medical Scans https://arxiv.org/pdf/1807.02437.pdf".

Doerr, S. A., et al. "Data-driven detection and registration of spine surgery instrumentation in intraoperative images." Medical Imaging 2020: Image-Guided Procedures, Robotic Interventions, and Modeling. vol. 11315. International Society for Optics and Photonics, 2020.

Dong, Hao, et al. "Automatic brain tumor detection and segmentation using u-net based fully convolutional networks." annual conference on medical image understanding and analysis. Springer, Cham, 2017.

Faster R-CNN: Towards Real-Time Object Detection with Region Proposal Networks https://ieeexplore.ieee.org/document/7485869.

Forsberg, Daniel, Erik Sjoblom, and Jeffrey L. Sunshine. "Detection and labeling of vertebrae in MR images using deep learning with clinical annotations as training data." Journal of digital imaging 30.4 (2017): 406-412.

Gao, C., Unberath, M., Taylor, R., & Armand, M. (2019). Localizing dexterous surgical tools in X-ray for image-based navigation. arXiv preprint arXiv:1901.06672.

Ghesu, F. C., Georgescu, B., Zheng, Y., Grbic, S., Maier, A., Hornegger, J., & Comaniciu, D. (2017). Multi-scale deep reinforcement learning for real-time 3D-landmark detection in CT scans. IEEE transactions on pattern analysis and machine intelligence, 41(1), 176-189.

Gooßen, A., Deshpande, H., Harder, T., Schwab, E., Baltruschat, I., Mabotuwana, T., . . . & Saalbach, A. (2019). Deep learning for pneumothorax detection and localization in chest radiographs. arXiv preprint arXiv:1907.07324.

"Group-wise Deep Object Co-Segmentation with Co-Attention Recurrent Neural Network https://openaccess.thecvf.com/content_ICCV_2019/papers/Li_Group-Wise_Deep_Object_Co-Segmentation_With_Co-Attention_Recurrent_Neural_Network_ICCV_2019_paper.pdf".

Hasan, S. M., & Linte, C. A. (2019). U-NetPlus: a modified encoder-decoder U-Net architecture for semantic and instance segmentation of surgical instrument. arXiv preprint arXiv:1902.08994.

Li Peiliang et al: " Stereo R-CNN Based 3D Object Detection for Autonomous Driving", 2019 IEEE/CVF Conference on Computer Vision and Pattern Recognition ( CVPR), IEEE, Jun. 15, 2019 ( Jun. 15, 2019), pp. 7636-7644.

Zhang Xiaoxuan et al: "Deformable 3D-2D 1-20 image registration and analysis of global spinal alignment in long-length intraoperative spine imaging", Medical Physics., vol. 49, No. 9, Jul. 27, 2022 (Jul. 27, 2022), pp. 5715-5727.

Uneri Ali et al: "Multi-slot intraoperative imaging and 3D-2D registration for evaluation of long surgical constructs in spine surgery", Medical Imaging 2020: Image-Guided Procedures, Robotic Interventions, and Modeling, Mar. 16, 2020 (Mar. 16, 2020), pp. 113152M-1.

Uneri A et al: "Intraoperative evaluation of device placement in spine surgery using known-component 30-20•image registration", Physics in Medicine and Biology, Institute of Physics Publishing, Bristol GB, vol. 62,. No. 8, Mar. 28, 2017 (Mar. 28, 2017), pp. 3330-3351.

Drobny David et al: "Towards Automated Spine Mobility Quantification: A Locally Rigid CT to X-ray Registration Framework", Jun. 9, 2020 (Jun. 9. 2020), 16th European Conference—Computer Vision—ECCV 2020, Cornell University L:Cbrary, 201 Olin Library Cornell University Ithaca, NY 14853, pp. 67-77.

International Search Report and Written Opinion regarding International Patent Application No. PCT/US2022/050414, dated Mar. 9, 2023.

Zhang Xiaoxuan et al: "Long-length tomosynthesis and 3D-2D registration for intraoperative assessment of spine instrumentation", Physics in Medicine and Biology, Institute of Physics Publishing, Bristol, GB, vol. 66,. No. 5, Feb. 16, 2021, p. 55008.

International Search Report and Written Opinion regarding International Patent Application No. PCT/US2022/050422, dated Mar. 10, 2023.

International Search Report and Written Opinion regarding International Patent Application No. PCT/US2022/050406, dated Mar. 9, 2023.

Xie, Y., Chao, M., Lee, P. and Xing, L., "Feature-based rectal contour propagation from planning CT to cone beam CT," Med. Phys. 35(10), 4450-4459 (2008).

Zhen, X., Yan, H., Zhou, L., Jia, X. and Jiang, S. B., "Deformable image registration of CT and truncated cone-beam CT for adaptive radiation therapy," Phys. Med. Biol. 58(22), 7979-7993 (2013).

Zhang, X., Uneri, A., Wu, P., Ketcha, M. D., Jones, C. K., Huang, Y., Lo, S. F. L., Helm, P. A. and Siewerdsen, J. H., "Long-length tomosynthesis and 3D-2D registration for intraoperative assessment of spine instrumentation," Phys. Med. Biol. 66(5), 0-17 (2021).

Zhang, J., Weir, V., Fajardo, L., Lin, J., Hsiung, H. and Ritenour, E. R., "Dosimetric characterization of a cone-beam O-armTM imaging system," J. Xray. Sci. Technol. 12(4), 305-317 (2009).

Wozniak, M., Sitka, J., & Wieczorek, M. (2021). Deep neural network correlation learning mechanism for CT brain tumor detection. Neural Computing and Applications, 1-16.

Yamazaki, Y., Kanaji, S., Matsuda, T., Oshikiri, T., Nakamura, T., Suzuki, S., . . . & Kakeji, Y. (2020). Automated surgical instrument detection from laparoscopic gastrectomy video images using an open source convolutional neural network platform. Journal of the American College of Surgeons, 230(5), 725-732.

Zhang, R., Cheng, C., Zhao, X., & Li, X. (2019). Multiscale mask R-CNN-based lung tumor detection using PET Imaging. Molecular imaging, 18, 1536012119863531.

Zhang, X., Uneri, A., Wu, P., Ketcha, M. D., Doerr, S. A., Jones, C. K., Helm, P. A., & Siewerdsen, J. H. (2020). Multi-slot extended view imaging on the O-Arm: image quality and application to intraoperative assessment of spinal morphology. Medical Imaging 2020: Image-Guided Procedures, Robotic Interventions, and Modeling, Proc. of SPIE 11315 113152B-1, CCCcode: 1605-7422/20/$21. https://doi.org/10.1117/12.2549710.

Wu, H., Bailey, C., Rasoulinejad, P., & Li, S. (2018). Automated comprehensive Adolescent Idiopathic Scoliosis assessment using MVC-Net. Medical Image Analysis, 48, 1-11. https://doi.org/10.1016/j.media.2018.05.005.

Yang, D. H., Xiong, T., & Xu, D. (2018). Automatic Vertebra Labeling in Large-Scale Medical Images Using Deep Image-to-Image Network with Message Passing and Sparsity Regularization. Advances in Computer Vision and Pattern Recognition, 179-197. https://doi.org/10.1007/978-3-030-13969-8_9.

Yang, Z., Cao, Z., Zhang, Y., Tang, Y., Lin, X., Ouyang, R., Wu, M., Han, M. K., Xiao, J., Huang, L., Wu, S., Chang, P. Y., & Ma, J. (2021). MommiNet-v2: Mammographic multi-view mass identification networks. Medical Image Analysis, 73, 102204. https://doi.org/10.1016/j.media.2021.102204.

Yeh, Y., Weng, C., Huang, Y., Fu, C., Tsai, T., & Yeh, C. (2021). Deep learning approach for automatic landmark detection and alignment analysis in whole-spine lateral radiographs. Scientific Reports, 11(1). https://doi.org/10.1038/s41598-021-87141-x.

Huang Y. et al: "Multi-perspective region-based CNNs for vertebrae labeling in intraoperative long-length images", Computer Methods and Programs in Biomedicine., vol. 227, Nov. 3, 2022 (Nov. 3, 2022), p. 107222.

Haofu Liao et al: "Joint Vertebrae Identification and Localization in Spinal CT Images by Combining Short- and Long-Range Contextual Information", arxiv.org, Cornell University Library, 201 Olin Library Cornell University Ithaca, NY 14853, Dec. 9, 2018 (Dec. 9, 2018).

(56) References Cited

OTHER PUBLICATIONS

Zhang Kailai et al: "MPF-net: An effective framework for automated cobb angle estimation", Medical Image Analysis, Oxford University Press, Oxofrd, GB, vol. 75, Oct. 16, 2021 (Oct. 16, 2021).

International Search Report and Written Opinion regarding International Application No. PCT/US2022/050400, dated Mar. 2, 2023.

"Image Co-Segmentation Using Graph Convolution Neural Network https://www.ee.iitb.ac.in/course/~avik/ICVGIP18_arXiv.pdf".

Jin, Y., Dou, Q., Chen, H., Yu, L., Qin, J., Fu, C. W., & Heng, P. A. (2017). SV-RCNet: workflow recognition from surgical videos using recurrent convolutional network. IEEE transactions on medical imaging, 37(5), 1114-1126.

Kim, K. C., Cho, H. C., Jang, T. J., Choi, J. M., & Seo, J. K. (2020). Automatic detection and segmentation of lumbar vertebrae from X-ray images for compression fracture evaluation. Computer Methods and Programs in Biomedicine, 105833.

"Object Detection Based on Binocular Vision with Convolutional Neural Network https://doi.org/10.1145/3297067.3297081".

"Object Detection in Multi-view X-Ray Images https://link.springer.com/chapter/10.1007/978-3-642-32717-9_15".

"Semantic Segmentation of Video Sequences with Convolutional LSTMs https://arxiv.org/pdf/1905.01058.pdf".

"Spatiotemporal CNN for Video Object Segmentation https://openaccess.thecvf.com/content_CVPR_2019/papers/Xu_Spatiotemporal_CNN_for_Video_Object_Segmentation_CVPR_2019_paper.pdf".

"X-Net: A Binocular Summation Network for Foreground Segmentation https://doi.org/10.1109/ACCESS.2019.2919802".

"You Only Look Once https://pjreddie.com/darknet/yolo/".

Bayat, A., Sekuboyina, A., Hofmann, F., Husseini, M. E., Kirschke, J. S., & Menze, B. H. (2019). Vertebral Labelling in Radiographs: Learning a Coordinate Corrector to Enforce Spinal Shape. Springer International Publishing EBooks, 39-46. https://doi.org/10.1007/978-3-030-39752-4_4.

Arif, S. M. M. R. A., Knapp, K. M., & Slabaugh, G. (2018). Fully automatic cervical vertebrae segmentation framework for X-ray images. Computer Methods and Programs in Biomedicine, 157, 95-111. https://doi.org/10.1016/j.cmpb.2018.01.006.

De Silva, T., Vedula, S. S., Perdomo-Pantoja, A., Vijayan, R. C., Doerr, S. A., Uneri, A., Han, R., Ketcha, M. D., Skolasky, R. L., Witham, T. F., Theodore, N., & Siewerdsen, J. H. (2020). SpineCloud: image analytics for predictive modeling of spine surgery outcomes. Journal of Medical Imaging, 7(03), 1. https://doi.org/10.1117/1.jmi.7.3.031502.

DeVine, J. G., Chutkan, N. B., Norvell, D. C., & Dettori, J. R. (2010). Avoiding Wrong Site Surgery. Spine, 35 (Supplement), S28-S36. https://doi.org/10.1097/brs.0b013e3181d833ac.

Diebo, B. G., Oren, J. H., Challier, V., Lafage, R., Ferrero, E., Liu, S., Vira, S., Spiegel, M., Harris, B. P., Liabaud, B., Henry, J. K., Errico, T. J., Schwab, F. J., & Lafage, V. (2016). Global sagittal axis: a step toward full-body assessment of sagittal plane deformity in the human body. Journal of Neurosurgery, 25(4), 494-499. https://doi.org/10.3171/2016.2.spine151311.

Doerr, S. A., De Silva, T., Vijayan, R. C., Han, R., Uneri, A., Ketcha, M. D., Zhang, X., Khanna, N., Westbroek, E. M., Jiang, B., Zygourakis, C. C., Aygun, N., Theodore, N., & Siewerdsen, J. H. (2020). Automatic analysis of global spinal alignment from simple annotation of vertebral bodies. Journal of Medical Imaging, 7(03), 1. https://doi.org/10.1117/1.imi.7.3.035001.

Gilad, I., & Nissan, M. (1985). Sagittal radiographic measurements of the cervical and lumbar vertebrae in normal adults. British Journal of Radiology, 58(695), 1031-1034. https://doi.org/10.1259/0007-1285-58-695-1031.

Huang, Y., Uneri, A., Jones, C. K., Zhang, X., Ketcha, M. D., Aygun, N., Helm, P. A., & Siewerdsen, J. H. (2021). 3D vertebrae labeling in spine CT: an accurate, memory-efficient (Ortho2D) framework. Physics in Medicine and Biology, 66(12), 125020. https://doi.org/10.1088/1361-6560/ac07c7.

Huang, Y., Jones, C. K., Zhang, X., Johnston, A., Aygun, N., Witham, T. F., Helm, P. A., Siewerdsen, J., & Uneri, A. (2022). Automatic labeling of vertebrae in long-length intraoperative imaging with a multi-view, region-based CNN. Medical Imaging 2022: Image-Guided Procedures, Robotic Interventions, and Modeling. https://doi.org/10.1117/12.2611912.

Kurochka, K. S., & Panarin, K. A. (2021). An algorithm of segmentation of a human spine X-ray image with the help of Mask R-CNN neural network for the purpose of vertebrae localization. 2021 56th International Scientific Conference on Information, Communication and Energy Systems and Technologies (ICEST). https://doi.org/10.1109/icest52640.2021.9483467.

Lehman, R. A., Lenke, L. G., Helgeson, M. D., Eckel, T. T., & Keeler, K. A. (2010). Do Intraoperative Radiographs in Scoliosis Surgery Reflect Radiographic Result? Clinical Orthopaedics and Related Research, 468(3), 679-686. https://doi.org/10.1007/s11999-009-0873-z.

Li, Y., Liang, W., Zhang, Y., An, H., & Tan, J. (2016). Automatic Lumbar Vertebrae Detection Based on Feature Fusion Deep Learning for Partial Occluded C-arm X-ray Images. International Conference of the IEEE Engineering in Medicine and Biology Society. https://doi.org/10.1109/embc.2016.7590785.

Liao, H., Mesfin, A., & Luo, J. (2018). Joint Vertebrae Identification and Localization in Spinal CT Images by Combining Short- and Long-Range Contextual Information. IEEE Transactions on Medical Imaging, 37(5), 1266-1275. https://doi.org/10.1109/tmi.2018.2798293.

Illés, T., & Somoskeöy, S. (2012). The EOSTM imaging system and its uses in daily orthopaedic practice. International Orthopaedics, 36(7), 1325-1331. https://doi.org/10.1007/s00264-012-1512-y.

Cai, Yunliang, et al. "Multi-modality vertebra recognition in arbitrary views using 3D deformable hierarchical model." IEEE transactions on medical imaging 34.8 (2015): 1676-1693. (Year: 2015).

Qin, Chunli, et al. "Vertebrae labeling via end-to-end integral regression localization and multi-label classification network." IEEE Transactions on Neural Networks and Learning Systems 33.6 (2021): 2726-2736. (Year: 2021).

\* cited by examiner

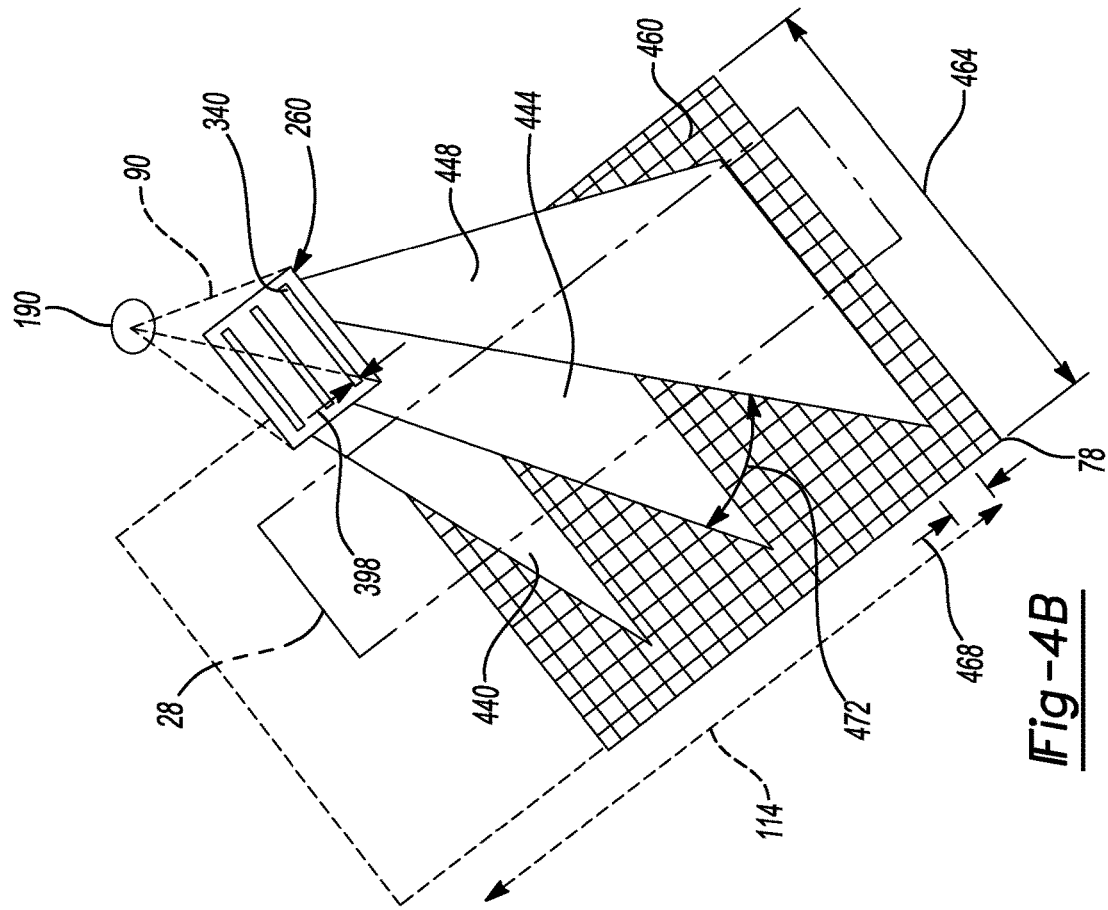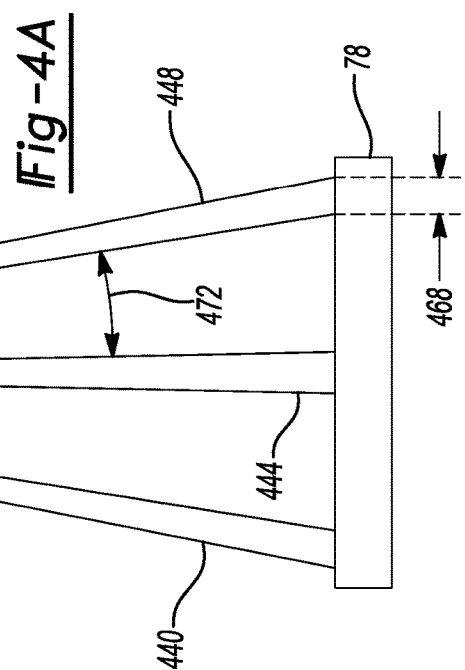

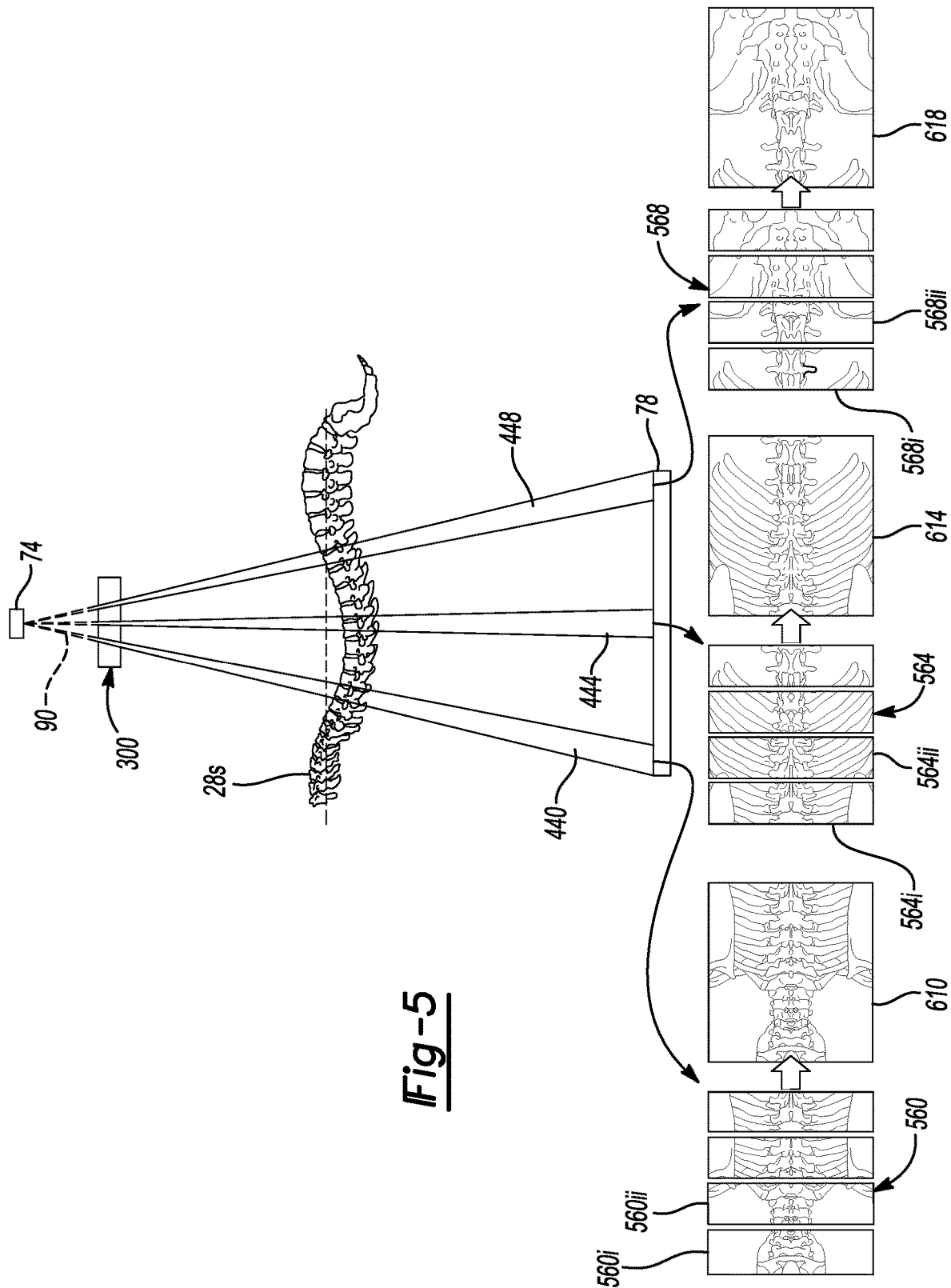

SYSTEM AND METHOD FOR IDENTIFYING AND CLASSIFYING A FEATURE IN AN IMAGE OF A SUBJECT

CROSS-REFERENCE TO RELATED APPLICATIONS

This application claims the benefit of U.S. Provisional Application No. 63/283,762, filed on Nov. 29, 2021, entitled "Feature Detection of a Plurality of Images." This application includes subject matter similar to that disclosed in concurrently filed U.S. patents application Ser. Nos. 17/887,599; 17/887,618; and 17/887,637. The entire disclosures of all of the above applications are incorporated herein by reference.

FIELD

The present disclosure relates to imaging a subject, and particularly to a system to acquire image data for generating a selected view of the subject and identifying and/or classifying features within the image of the subject.

BACKGROUND

This section provides background information related to the present disclosure which is not necessarily prior art.

A subject, such as a human patient, may undergo a procedure. The procedure may include a surgical procedure to correct or augment an anatomy of the subject. The augmentation of the anatomy can include various procedures, such as movement or augmentation of bone, insertion of an implant (i.e., an implantable device), or other appropriate procedures.

A surgeon can perform the procedure on the subject with images of the subject that are based on projections of the subject. The images may be generated with one or more imaging systems such as a magnetic resonance imaging (MRI) system, a computed tomography (CT) system, a fluoroscopy (e.g., C-Arm imaging systems).

SUMMARY

This section provides a general summary of the disclosure, and is not a comprehensive disclosure of its full scope or all of its features.

According to various embodiments, a system to acquire image data of a subject may be an imaging system that uses x-rays. The subject may be a living patient (e.g., a human patient). The subject may also be a non-living subject, such as an enclosure, a casing, etc. Generally, the imaging system may acquire image data of an interior of the subject. The imaging system may include a moveable source and/or detector that is moveable relative to the subject.

An imaging system may include a movable source and/or detector to create a plurality of projections of a subject. The plurality of projections may be acquired in a linear path of movement of the source and/or detector. The plurality of projections may then be combined, such as by stitching together, to generate or form a long view (also referred to as a long film). The long view may be a two-dimensional view of the subject. In various embodiments, however, the long film may also be a three-dimensional (3D) image. The 3D image may be reconstructed based on image data acquired with the imaging system.

In various embodiments, the imaging system may acquire a plurality of projections at different perspectives relative to the subject. The different perspectives may be generated due to a parallax effect between different paths of x-rays from a single source to a detector through the subject. The parallax effect may allow for different views of the same position of the subject. The parallax effect may be formed due to a filter having a plurality of slits or slots through which the x-rays pass and impinge upon the detector. Accordingly, movement of the source and/or detector relative to the subject may allow for acquisition of a plurality of projections through the subject including a parallax effect. The plurality of projections may then be stitched to form a plurality of long views of the subject due to movement of the source and/or detector. An imaging system may include that disclosed in U.S. Pat. No. 10,881,371 to Helm et al., incorporated herein by reference.

In one or more of the projections, a feature may be identified, such as a selected edge or portion. For example, a selected one or more vertebrae may be identified in each of a plurality of projections. The vertebra may be a specific vertebra, such as L5, T3, etc. Various projections that include the same portion may then be combined, such as stitched together. The identification may then be incorporated or applied to the stitched image.

The identification may be performed in one or more manners, as discussed herein. For example, an edge detection algorithm may be applied to determine edges and/or identify portions based thereon. One or more machine learning systems may be used to identify one or more features, such as an edge or a portion. The machine learning system may be used to identify selected portions in one or more projections and/or a stitched image.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4A and FIG. 4B are schematic illustrations of a slotted filter assembly relative to a source and a detector;

FIG. 5 is a schematic illustration of acquiring a plurality of projections in intermediate images, according to various embodiments;

Corresponding reference numerals indicate corresponding parts throughout the several views of the drawings.

DETAILED DESCRIPTION

Example embodiments will now be described more fully with reference to the accompanying drawings.

A subject may be imaged with an imaging system, as discussed further herein. The subject may be a living subject, such as a human patient. Image data may be acquired of the human patient and may be combined to provide an image of the human patient that is greater than any dimension of any single projection acquired with the imagining system. It is understood, however, that image data may be acquired of a non-living subject, such an inanimate subject including a housing, casing, interior of a super structure, or the like. For example, image data may be acquired of an airframe for various purposes, such as diagnosing issues and/or planning repair work.

Further, the image data may be acquired having a plurality of projections that may be generated by dividing a single projection area into a plurality of projections. As discussed further herein, an imaging system may include a filter or construct that divides a beam, such as an x-ray cone beam, into a plurality of portions (e.g., fans). Each of the fans may be used to acquire image data of the subject at a single position, but due to the division of a cone into a plurality of distinct portions, such as fans, a single cone projection may include a plurality of projections due to the fans. In various embodiments, three slots may be used to generate three fans. The source may also and/or thereafter move relative to the subject to acquire the plurality of distinct projections at a plurality of positions relative of the subject to the source.

Figure 1:
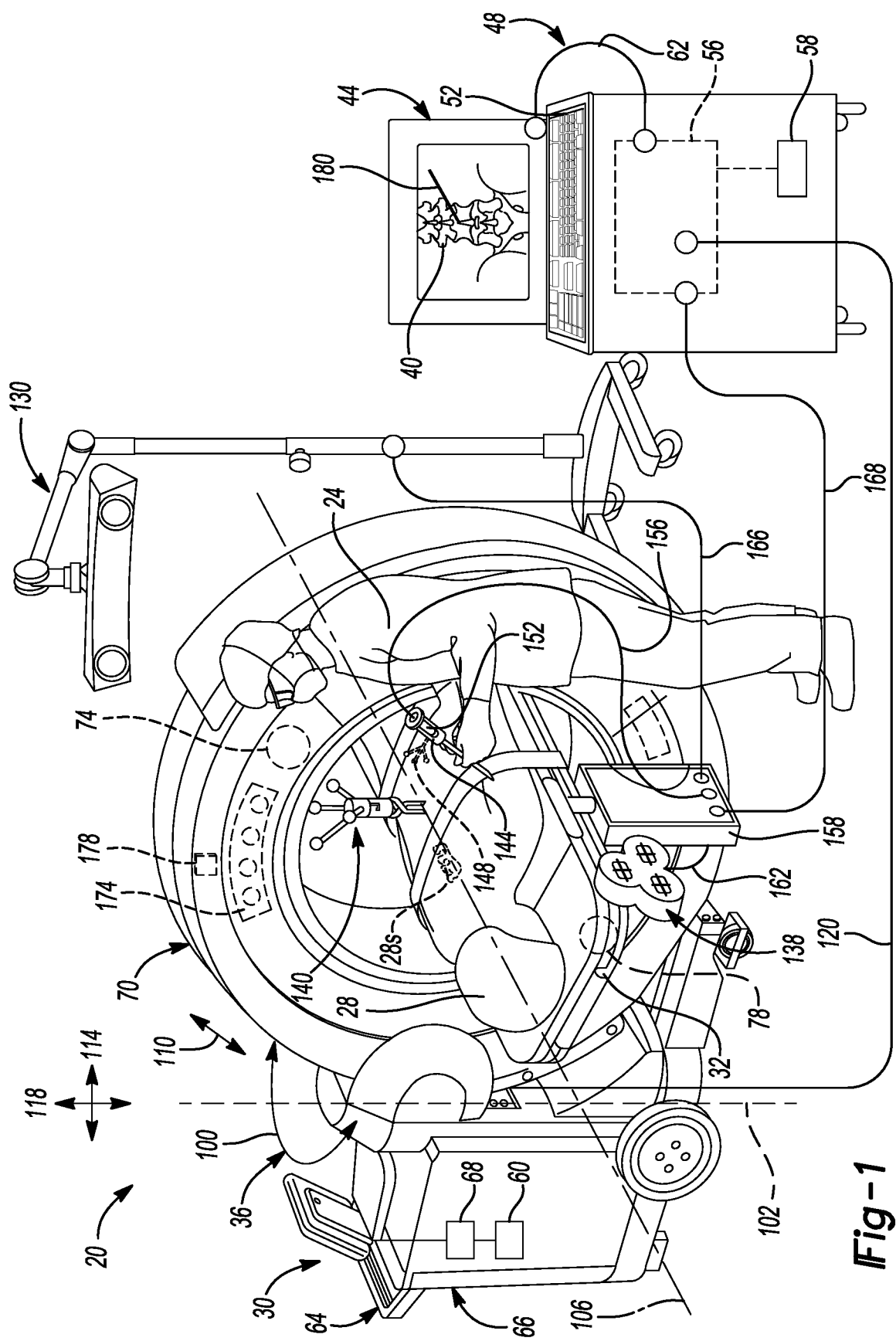
FIG. 1 is an environmental view of an imaging system in an operating theatre.

With reference to FIG. 1, a schematic view of a procedure room 20 is illustrated. A user 24, such as a surgeon, can perform a procedure on a subject, such as a patient 28. The subject may be placed on a support, such as a table 32 for a selected portion of the procedure. The table 32 may not interfere with image data acquisition with an imaging system 36. In performing the procedure, the user 24 can use the imaging system 36 to acquire image data of the patient 28 to allow a selected system to generate or create images to assist in performing a procedure. Images generated with the image data may be two-dimensional (2D) images, three-dimensional (3D), or appropriate type of images, such as a model (such as a three-dimensional (3D) image), long views, single projections views, etc. can be generated using the image data and displayed as an image 40 on a display device 44. The display device 44 can be part of and/or connected to a processor system 48 that includes an input device 52, such as a keyboard, and a processor 56, which can include one or more processors, processor module, and/or microprocessors incorporated with the processing system 48 along with selected types of non-transitory and/or transitory memory 58. A connection 62 can be provided between the processor 56 and the display device 44 for data communication to allow driving the display device 44 to display or illustrate the image 40. The processor 56 may be any appropriate type of processor such as a general-purpose processor that executes instructions included in a program or an application specific processor such as an application specific integrated circuit.

The imaging system 36 can include an O-Arm® imaging system sold by Medtronic Navigation, Inc. having a place of business in Louisville, CO, USA. The imaging system 36, including the O-Arm® imaging system, or other appropriate imaging systems may be in use during a selected procedure, such as the imaging system described in U.S. Patent App. Pubs. 2012/0250822, 2012/0099772, and 2010/0290690, all the above incorporated herein by reference. Further, the imaging system may include various features and elements, such as a slotted filter, such as that disclosed in U.S. Pat. No. 10,881,371 to Helm et al. and U.S. Pat. No. 11,071,507 to Helm et al., all the above incorporated herein by reference.

The imaging system 36, when, for example, including the O-Arm® imaging system, may include a mobile cart 60 that includes a controller and/or control system 64. The control system 64 may include a processor and/or processor system 66 (similar to the processor 56) and a memory 68 (e.g., a non-transitory memory). The memory 68 may include various instructions that are executed by the processor 66 to control the imaging system 36, including various portions of the imaging system 36.

The imaging system 36 may include further additional portions, such as an imaging gantry 70 in which is positioned a source unit (also referred to as a source assembly) 74 and a detector unit (also referred to as a detector assembly) 78. In various embodiments, the detector 78 alone and/or together with the source unit may be referred to as an imaging head of the imaging system 36. The gantry 70 is moveably connected to the mobile cart 60. The gantry 70 may be O-shaped or toroid shaped, wherein the gantry 70 is substantially annular and includes walls that form a volume in which the source unit 74 and detector 78 may move. The mobile cart 60 may also be moved. In various embodiments, the gantry 70 and/or the cart 60 may be moved while image data is acquired, including both being moved simultaneously. Also, the imaging system 36 via the mobile cart 60 can be moved from one operating theater to another (e.g., another room). The gantry 70 can move relative to the cart 60, as discussed further herein. This allows the imaging system 36 to be mobile and moveable relative to the subject 28, thus allowing it to be used in multiple locations and with multiple procedures without requiring a capital expenditure or space dedicated to a fixed imaging system.

The processor 66 may be a general-purpose processor or an application specific application processor. The memory system 68 may be a non-transitory memory such as a spinning disk or solid-state non-volatile memory. In various embodiments, the memory system may include instructions to be executed by the processor 66 to perform functions and determine results, as discussed herein.

In various embodiments, the imaging system 36 may include an imaging system that acquires images and/or image data by the use of emitting x-rays and detecting x-rays after interactions and/or attenuations of the x-rays with or by the subject 28. The x-ray imaging may be an imaging modality. It is understood that other imaging modalities are possible, such as other high energy beams, etc.

Figure 2:
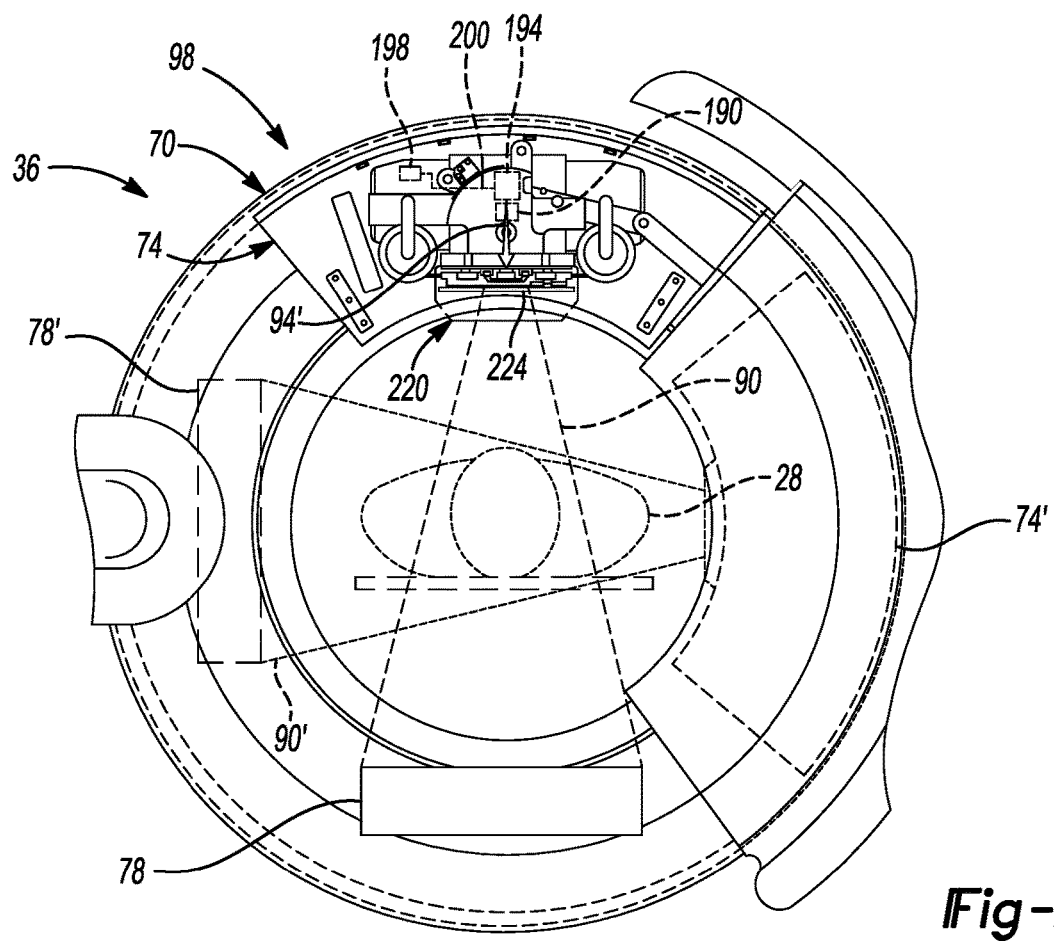
FIG. 2 is a detailed schematic view of an imaging system with a source and detector configured to move around a subject, according to various embodiments.

Thus, in the imaging system 36 the source unit 74 may be an x-ray emitter that can emit x-rays at and/or through the patient 28 to be detected by the detector 78. As is understood by one skilled in the art, the x-rays emitted by the source 74 can be emitted in a cone 90 along a selected main vector 94 and detected by the detector 78, as illustrated in FIG. 2. The source 74 and the detector 78 may also be referred to together as a source/detector unit 98, especially wherein the source 74 is generally diametrically opposed (e.g., 180 degrees (°) apart) from the detector 78 within the gantry 70.

The imaging system 36 may move, as a whole or in part, relative to the subject 28. For example, the source 74 and the detector 78 can move around the patient 28, e.g., a 360° motion, spiral, portion of a circle, etc. The movement of the source/detector unit 98 within the gantry 70 may allow the source 74 to remain generally 180° opposed (such as with a fixed inner gantry or rotor or moving system) to the detector 78. Thus, the detector 78 may be referred to as moving around (e.g., in a circle or spiral) the subject 28 and it is understood that the source 74 is remaining opposed thereto, unless disclosed otherwise.

Also, the gantry 70 can move isometrically (also referred as "wag") relative to the subject 28 generally in the direction of arrow 100 around an axis 102, such as through the cart 60, as illustrated in FIG. 1. The gantry 70 can also tilt relative to a long axis 106 of the patient 28 illustrated by arrows 110. In tilting, a plane of the gantry 70 may tilt or form a non-orthogonal angle with the axis 106 of the subject 28.

The gantry 70 may also move longitudinally in the direction of arrows 114 along the line 106 relative to the subject 28 and/or the cart 60. Also, the cart 60 may move to move the gantry 70. Further, the gantry 70 can move up and down generally in the direction of arrows 118 relative to the cart 30 and/or the subject 28, generally transverse to the axis 106 and parallel with the axis 102.

The movement of the imaging system 36, in whole or in part is to allow for positioning of the source/detector unit (SDU) 98 relative to the subject 28. The imaging device 36 can be precisely controlled to move the SDU 98 relative to the subject 28 to generate precise image data of the subject 28. The imaging device 36 can be connected to the processor 56 via a connection 120, which can include a wired or wireless connection or physical media transfer from the imaging system 36 to the processor 56. Thus, image data collected with the imaging system 36 can be transferred to the processing system 56 for navigation, display, reconstruction, etc.

The source 74, as discussed herein, may include one or more sources of x-rays for imaging the subject 28. In various embodiments, the source 74 may include a single source that may be powered by more than one power source to generate and/or emit x-rays at different energy characteristics. Further, more than one x-ray source may be the source 74 that may be powered to emit x-rays with differing energy characteristics at selected times.

According to various embodiments, the imaging system 36 can be used with an un-navigated or navigated procedure. In a navigated procedure, a localizer and/or digitizer, including either or both of an optical localizer 130 and/or an electromagnetic localizer 138 can be used to generate a field and/or receive and/or send a signal within a navigation domain relative to the subject 28. The navigated space or navigational domain relative to the subject 28 can be registered to the image 40. Correlation, as understood in the art, is to allow registration of a navigation space defined within the navigational domain and an image space defined by the image 40. A patient tracker or dynamic reference frame 140 can be connected to the subject 28 to allow for a dynamic registration and maintenance of registration of the subject 28 to the image 40.

The patient tracking device or dynamic registration device 140 and an instrument 144 can then be tracked relative to the subject 28 to allow for a navigated procedure. The instrument 144 can include a tracking device, such as an optical tracking device 148 and/or an electromagnetic tracking device 152 to allow for tracking of the instrument 144 with either or both of the optical localizer 130 or the electromagnetic localizer 138. A navigation/probe interface device 158 may have communications (e.g., wired or wireless) with the instrument 144 (e.g., via a communication line 156), with the electromagnetic localizer 138 (e.g., via a communication line 162), and/or the optical localizer 130 (e.g., via a communication line 166). The interface 158 can also communicate with the processor 56 with a communication line 168 and may communicate information (e.g., signals) regarding the various items connected to the interface 158. It will be understood that any of the communication lines can be wired, wireless, physical media transmission or movement, or any other appropriate communication. Nevertheless, the appropriate communication systems can be provided with the respective localizers to allow for tracking of the instrument 144 relative to the subject 28 to allow for illustration of a tracked location of the instrument 144 relative to the image 40 for performing a procedure.

One skilled in the art will understand that the instrument 144 may be any appropriate instrument, such as a ventricular or vascular stent, spinal implant, neurological stent or stimulator, ablation device, or the like. The instrument 144 can be an interventional instrument or can include or be an implantable device. Tracking the instrument 144 allows for viewing a location (including x,y,z position and orientation) of the instrument 144 relative to the subject 28 with use of the registered image 40 without direct viewing of the instrument 144 within the subject 28.

Further, the imaging system 36, such as the gantry 70, can include an optical tracking device 174 and/or an electromagnetic tracking device 178 to be tracked with the respective optical localizer 130 and/or electromagnetic localizer 138. Accordingly, the imaging device 36 can be tracked relative to the subject 28 as can the instrument 144 to allow for initial registration, automatic registration, or continued registration of the subject 28 relative to the image 40. Registration and navigated procedures are discussed in the above incorporated U.S. Pat. No. 8,238,631, incorporated herein by reference. Upon registration and tracking of the instrument 144, an icon 180 may be displayed relative to, including overlaid on, the image 40. The image 40 may be an appropriate image and may include a long film image, 2D image, 3D image, or any appropriate image as discussed herein.

With continuing reference to FIG. 2, according to various embodiments, the source 74 can include a single assembly that may include a single x-ray tube 190 that can be connected to a switch 194 that can interconnect a first power source 198 via a connection or power line 200. As discussed above, x-rays can be emitted from the x-ray tube 190 generally in the cone shape 90 towards the detector 78 and generally in the direction from the x-ray tube 190 as indicated by arrow, beam arrow, beam or vector 94. The switch 194 can switch power on or off to the tube 190 to emit x-rays of selected characteristics, as is understood by one skilled in the art. The vector 94 may be a central vector or ray within the cone 90 of x-rays. An x-ray beam may be emitted as the cone 90 or other appropriate geometry. The vector 94 may include a selected line or axis relevant for further interaction with the beam, such as with a filter member, as discussed further herein.

The subject 28 can be positioned within the x-ray cone 90 to allow for acquiring image data of the subject 28 based upon the emission of x-rays in the direction of vector 94 towards the detector 78. The x-ray tube 190 may be used to generate two-dimensional (2D) x-ray projections of the subject 28, including selected portions of the subject 28, or any area, region or volume of interest, in light of the x-rays impinging upon or being detected on a 2D or flat panel detector, as the detector 78. The 2D x-ray projections can be reconstructed, as discussed herein, to generate and/or display three-dimensional (3D) volumetric models of the subject 28, selected portion of the subject 28, or any area, region or volume of interest. As discussed herein, the 2D x-ray projections can be image data acquired with the imaging system 36, while the 3D volumetric models can be generated or model image data.

For reconstructing or forming the 3D volumetric image, appropriate techniques include Expectation maximization (EM), Ordered Subsets EM (OS-EM), Simultaneous Algebraic Reconstruction Technique (SART) and Total Variation Minimization (TVM), as generally understood by those skilled in the art. Various reconstruction techniques may also and alternatively include machine learning systems and algebraic techniques. The application to perform a 3D volumetric reconstruction based on the 2D projections allows for efficient and complete volumetric reconstruction. Generally, an algebraic technique can include an iterative process to perform a reconstruction of the subject 28 for display as the image 40. For example, a pure or theoretical image data projection, such as those based on or generated from an atlas or stylized model of a "theoretical" patient, can be iteratively changed until the theoretical projection images match the acquired 2D projection image data of the subject 28. Then, the stylized model can be appropriately altered as the 3D volumetric reconstruction model of the acquired 2D projection image data of the selected subject 28 and can be used in a surgical intervention, such as navigation, diagnosis, or planning. The theoretical model can be associated with theoretical image data to construct the theoretical model. In this way, the model or the image data 40 can be built based upon image data acquired of the subject 28 with the imaging device 36.

With continuing reference to FIG. 2, the source 74 may include various elements or features that may be moved relative to the x-ray tube 190. In various embodiments, for example, a collimator 220 may be positioned relative to the x-ray tube 190 to assist in forming the cone 90 relative to the subject 28. The collimator 220 may include various features such as movable members that may assist in positioning one or more filters within the cone 90 of the x-rays prior to reaching the subject 28. One or more movement systems 224 may be provided to move all and/or various portions of the collimator 220. Further, as discussed further herein, various filters may be used to shape the x-ray beam, such as shaping the cone 90, into a selected shape prior to reaching the subject 28. In various embodiments, as discussed herein, the x-rays may be formed into a thin fan or plane to reach and pass through the subject 28 and be detected by the detector 78.

Figure 3:
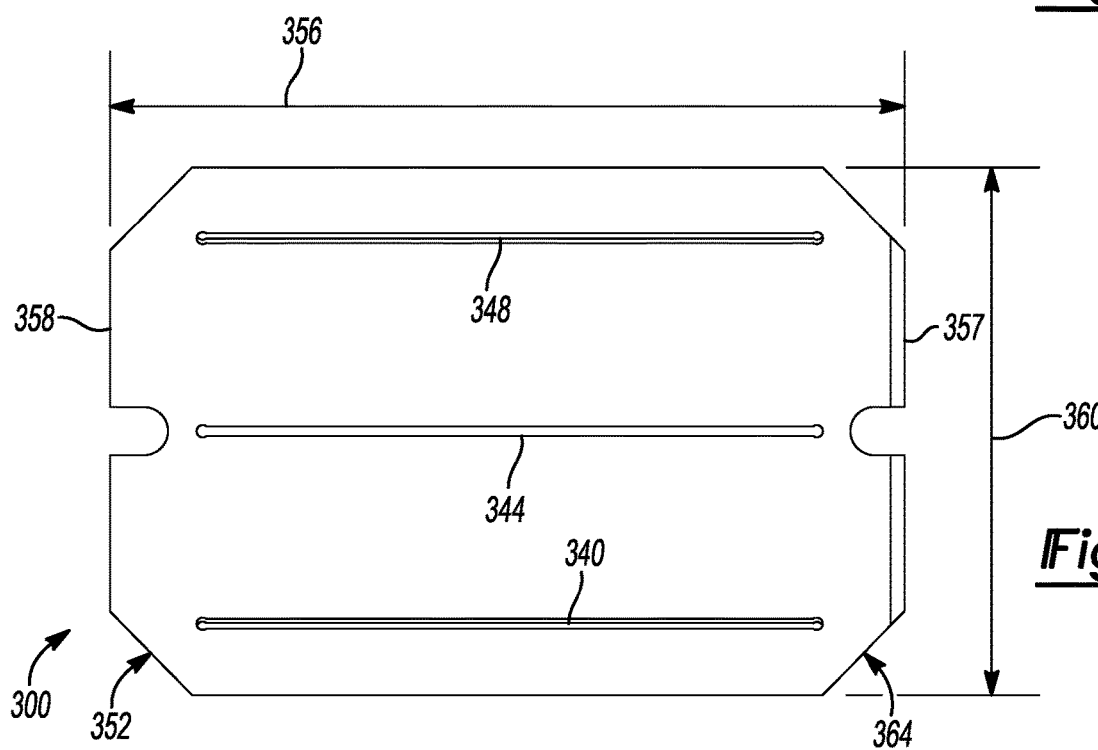
FIG. 3 is a top plan view of a slotted filter body, according to various embodiments.

Accordingly, the source 74 including the collimator 220 may include a filter assembly, such as that disclosed in U.S. Pat. No. 10,881,371 to Helm et al., incorporated herein by reference. The filter assembly may include one or more portions that allow for moving a filter relative to the x-ray tube 190 to shape and/or position the x-rays prior to reaching the subject 28. For example, with reference to FIG. 3, the filter assembly may include a slotted filter 300. The slotted filter 300 may be included in the filter assembly that is formed of one or more members. For example, the slotted filter 300 that may be sandwiched between or placed between one or more members. Nevertheless, for the subject discussion the slotted filter 300 will be discussed, briefly. As discussed herein, the slotted filter 300 may be used to filter and shape the beam from the x-ray source 74 such that three separate fans are created for generating image data of the subject 28.

The slotted filter 300 may include dimensions, as discussed further herein. The slotted filter 300 may be formed of a selected material such as tungsten carbide having a selected amount of tungsten, such as about 90% minimum tungsten. In various embodiments, the tungsten carbide is ANSI grade C2 tungsten carbide. The slotted filter 300 further includes a selected number of slots or slits that are formed through the slotted filter 300, such as a first slot 340, a second or middle slot 344, and a third slot 348. The slots 340, 344, 348 may be used to form selected x-ray beams, volumes, or areas, such as fans, when positioned to limit passage of the beam in the cone 90. Thus, the slotted filter 300 does not allow the entire cone 90 to pass to the subject 28 when positioned in the beam by the collimator 220.

Generally, the slotted filter 300 will block all or substantially all of the x-rays, save for the x-rays that pass through the slots 340, 344, 348. Accordingly, x-rays that engage the detector 78 when passing through the slotted filter 300 are limited to only those x-rays that pass through the slots 340, 344, 348. It is understood by one skilled in the art that the filter assembly may include additional portions in addition to the slotted filter 300 that may assist in refining and/or selecting spectral content of the x-rays that pass through the filter assembly 260.

The slotted filter 300 includes various features including the slots 340, 344, 348. The slotted filter 300 includes a main body or member 352 through which the slots 340, 344, 348 are formed. The main body 352 may have a selected thickness 354 (FIG. 4A) between a first surface 320 and a second surface 330 of the slotted filter 300. The thickness 354 may be about 0.01 in to about 1 in, including about 0.01 in to about 0.1 in, and further including about 0.07 in to about 0.1 in and further about 0.09 in (about 2.2 mm). It is understood that the thickness 354 of the main body 352 may be used to form or define the x-rays that pass through the slotted filter 300. The main body 352 may include further dimensions for various purposes, however, these dimensions may be based upon the size of the collimator or other appropriate constrictions. Nevertheless, in various embodiments, the main plate 352 of the slotted filter 300 may include a length dimension 356 between terminal ends 357, 358 of the main plate 352. The length 356 may be about 0.5 in. to about 2 in., and including about 1.4 in. (35 mm). A width dimension 360 may be about 0.1 in to about 2 in., and further including about 0.9 in. (22 mm). The main plate 352 of the slotted filter 300 may include various configurations, such as chamfered or angled corners 364 that may form an angle of about 45 degrees relative to the ends of the main body 352.

Again, it is understood, that the slotted filter 300 may include various configuration for fitting in a selected imaging system, such as the imaging system 36, and specific shapes of the exterior may be based upon configurations of the imaging system 36. The thickness 354, however, may be selected to ensure minimal or no x-ray radiation passes through the filter assembly 260 other than through the slots 340, 344, 348. In various embodiments, the slots may be filled with a radio transparent material and/or only be thinned areas rather than complete passages. Further, the slots may be formed in different shapes than slots. Regardless, the slotted member 300 member be used to form a plurality of x-ray beams or regions, as discussed herein.

With reference to FIGS. 4A and 4B, the slotted member 300, according to various embodiments, allows for a formation of three x-ray fans or areas of x-rays including a first fan 440, a second fan 444, and a third fan 448 due to the respective slots 340, 344, 348. The three fans are formed by the slotted filter 300 filtering x-rays from the source 190 save for the area of the slots 340, 344, 348. In other words, slotted filter 300 filters the x-rays from the source 190 and allows the x-rays to pass through the slots 340, 344, 348 to form the fans 440, 444, 448.

As discussed further herein, the three fans 440, 444, 448 allow for generation of selected image projections due to an imaging area on the detector 78. Further, due to angles of formation of the slots, the first and third fans 440, 448 are not substantially distorted due to interaction of x-rays with the plate member 352. It is further understood that the numbering of the slots 340, 344, 348 and the respective fans 440, 444, 448 is merely for clarity of the current discussion, and not intended to require any specific order. Further, it is understood, that slotted filter 300 may include a selected number of slots, such as less than three or more than three; three slots are illustrated and discussed for the current disclosure. It is understood, however, that the three slots 340, 344, 348 allow for the generation of a long view in an efficient and fast manner, as discussed further herein. Including a selected different number of slots may allow for a generation of a different number of intermediate images as discussed herein, but is not required.

As discussed above, the slotted filter 300 may be used in the imaging system 36 to acquire images of the subject 28. Returning reference to FIG. 2, the SDU 98 may be moved around the subject 28 within the gantry 70. It is understood that the SDU 98 may be moved in any appropriate manner, and that the imaging system 36 is exemplary. For example, the slotted filter 300 may be used with a C-arm imaging system, or any appropriate imaging system. Nevertheless, in various embodiments, the SDU 98 may be rotated from a first position to a second position, such as about 90 degrees apart. For example, as illustrated in FIG. 2, a first position of the SDU 98 may include the source 74 directing the x-rays along the cone 90 for the detector 78 which may be generally an anterior to posterior (AP) orientation relative to the subject 28. The SDU 90 may be rotated 90 degrees, such that the source is at a second source position 74' (which may emit a second beam cone 90') and the detector may be moved to a different position such as at a second detector position 78', which may be a lateral (LAT) or side-to-side view of the subject 28. The SDU 98 may be positioned at either or both of the positions and a line scan of the subject 78 may be formed.

The line scan may include moving the gantry 70, including the SDU 98, along the long axis 106 of the subject 28 which may also be referred to as a Z-axis or Z-direction of the imaging system 36 generally in the direction of the double headed arrow 114 which may be, in various embodiments, along the axis 106 of the subject 28, as illustrated in FIG. 1. The detector 78 may, therefore, be moved in a linear direction substantially with movement only in the direction of the double headed arrow 114 along a Z-axis. The acquired image data may be used to form a long film or long view of the subject 28 with the image data acquired at one or both of the positions of the detector 78, 78' as illustrated in FIG. 2. The use of slotted filter 300 may be used to generate a plurality of views along the Z axis, as discussed further herein.

As illustrated in FIGS. 4A, 4B, and 5, the slotted filter 300 may be used to form the three fans 440, 444, 448 that reach or have attenuations that are detected by the detector 78. Each of the fans 440, 444, 448 directly or have attenuations that impinge or contact the detector 78 at a substantially narrow position or area. The detector 78 may include a plurality of excitable or detector regions or portions 460. The detector regions 460 may also be referred to as pixels and may relate to a single picture element (pixel) that is illustrated on the display 44 in the image 40.

The entire cone 90 from the source 74 may have an area that would excite or impinge upon the entire surface of the detector 78. However, the individual fans 440, 444, 448 generally impinge upon only a narrow band or number of the pixels 460. It is understood that the number of pixels excited may include an entire width 464 of the detector 78, but limited to only a selected length 468 of the detector. For example, the respective fans 440, 444, 448 may impinge upon, assuming that no object or subject is within the path of the x-rays (e.g., an air scan), about 10 to about 100 pixels. The number of pixels excited in the dimension 468 on the detector 78, however, may be augmented or adjusted depending upon the distance from the detector 78 of slotted filter 300, the width of the slots (340, 344, 348), or other appropriate considerations. Nevertheless, each of the respective fans 440, 444, 448 will impinge upon the detector 78 at a substantially narrow position and excite a length 468 of pixels that may be along a substantially entire width 464 of the detector 78. A width of 398 of one or more of the slots 340-348 may allow the length of pixels 468 to be excited (e.g., generate image data) limits or eliminates parallax distortion within the image portion collected with the imaging system using the slotted filter 300, as discussed herein. Again, it is understood that any one or more of the fans may excite a selected portion of the detector that is not an entire width of the detector. The collected image data, however, may still be used as discussed herein, such as for feature detection and/or registration.

Further, the detector 78 may be impinged upon by the three fans 440, 444, 448 substantially simultaneously from a single position of the source tube 190 along the Z axis generally in the direction of the double headed arrow 114. The detector 78, therefore, may output three different images or image data for three different positions of the x-ray at each single position of the source tube 190. Movement, of the source tube 190 of the source 74 generally in the direction of the double headed arrow 114, however, may create a plurality of three views along the Z axis, as discussed further herein. Each of the fans 440, 444, 448 may be separated by a selected distance, which may also be an angular distance 472.

The imaging system 36 may be used to generate images of the subject 28, for various purposes. As discussed above, the images may be generated of the subject 28 for performing a procedure on the subject 28, such as a spinal fusion and/or implants relative to or adjunct to a spinal fusion. In various embodiments, therefore, user 24 may evaluate the subject 28 by viewing and evaluating images of the subject 28 for determination of placement of selected implants, such as pedicle screws. Accordingly, the imaging system 36 may be used to acquire an image of the subject 28. The image system 36 may be used to acquire one or a plurality of projections. As further discussed above, the detector 78 detects x-rays that pass through or are attenuated by the subject 28. Generally, however, the detector 78 detects a single projection at a time. The imaging system 36, including the control system 64, either alone or in combination with the processor system 48, may generate a long film or long view of the subject 28 by accumulating and combining (e.g., stitching) a plurality of projections of the subject 28. In various embodiments, the imaging system 36, therefore, may be operated to acquire a plurality of images.

According to various embodiments, for example, less than the entire subject 28 may be imaged. The acquisition of image data of the subject 28, such as a spine 28s of the subject 28, may be made by moving the imaging system 36, including the SDU 98, in the selected manner. For example, as discussed above, a linear or Z-axis image may be acquired of the spine 28s of the subject 28. The source 74 may be moved with the slotted filter 300 to filter the cone 90 to generate or form the fans 440, 444, 448 that impinge on the spine 28s to generate the various projections.

Each of the projections and/or at each of the projection positions, each of the slots in the slotted filter 300 may allow for the acquisition of a different "view" of the subject 28 during scanning of the subject 28. For example, each of the three fans 440, 444, 448 acquire a projection at a single position of the SDU 98. Accordingly, at each view the perspective of the subject 28 may be different. A three-dimensional model of the subject 28 may be reconstructed using the plurality of views of the subject 28 acquired even during the line scans of the subject. A line scan of the subject, as discussed above, may be a substantially linear movement, such as generally parallel with the long axis 106 of the subject 28. Thus, the SDU 98 may not rotate around the subject 28 during the acquisition of the linear scan. Nevertheless, the plurality of projections from the various perspectives, as discussed herein, may be used to reconstruct a three-dimensional model of the subject 28 using the single or two line scans (e.g. AP and lateral line scans). These plurality of projections from various perspectives may also be used to identify and/or localize items or features in the image data (e.g., high-contrast objects, such as bony anatomy or implants). The localized position from each of the more than one slot projections may also be used to generate a three-dimensional model of the subject that is imaged. The different position in the plane determined in each of the projections may be used to generate the 3D model, as is understood in the art.

Figure 6:
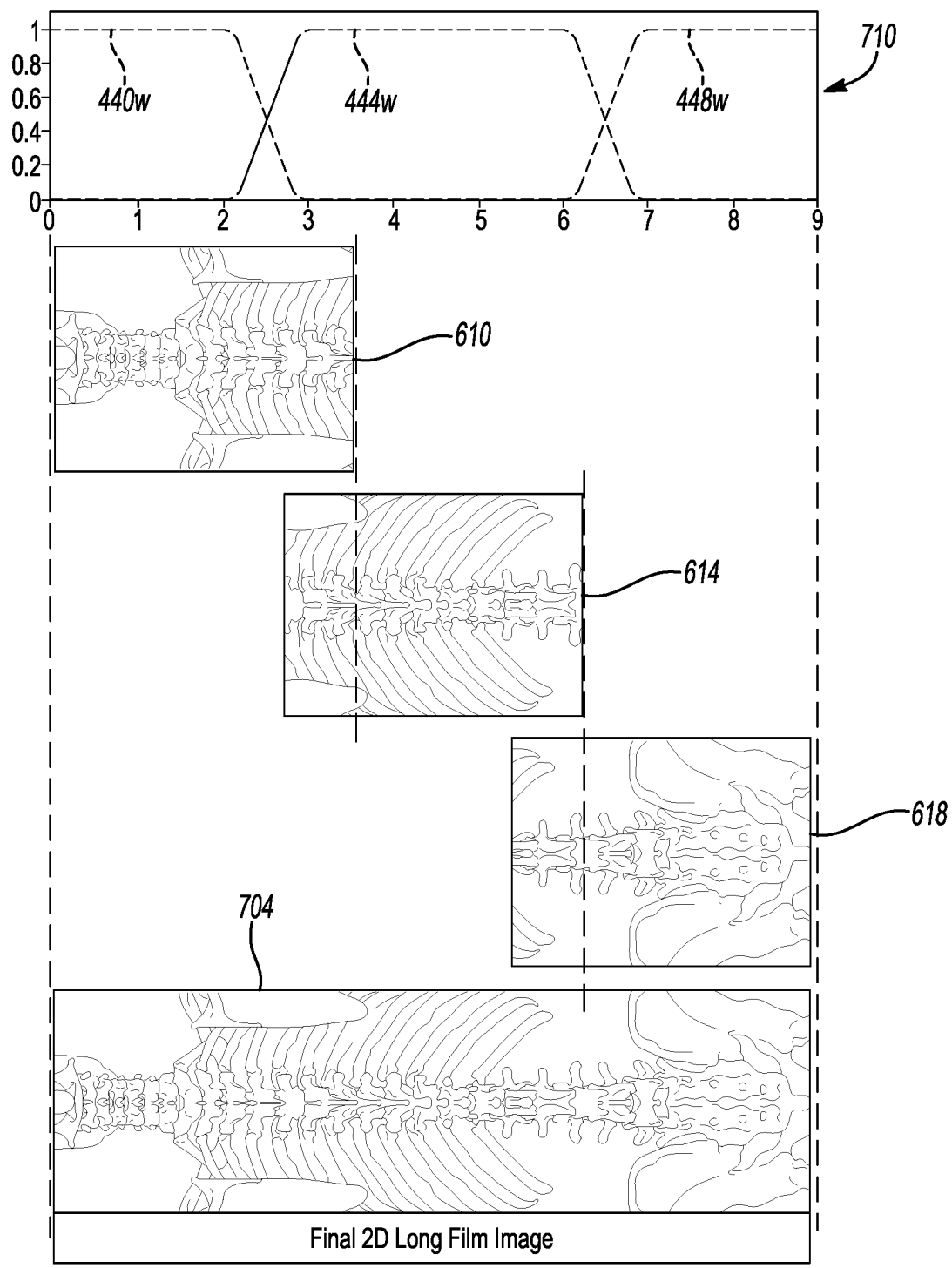
FIG. 6 is a schematic illustration of a formation of a long view with a weighting function.

In various embodiments, turning reference to FIGS. 5 and 6 a reconstruction of a long view 704 may be made as disclosed in U.S. Pat. No. 10,881,371 to Helm et al. and U.S. Pat. No. 11,071,507 to Helm et al., all of the above incorporated herein by reference. The reconstruction may include various intermediate reconstructions and a final complete or long reconstruction. The intermediate reconstructions may be based on the one or more individual slot projections and the complete reconstruction on the individual slot projections and/or the intermediate reconstructions.

The reconstruction of the long view (also referred to herein as reconstructed long view) generally includes various features and steps that may be included as instructions, such as with an algorithm, that are executed by one or more processors or processor systems. For example, the imaging system processor 66 and/or the processing system 48 having a processor 56, may execute instructions to generate the long view based upon the plurality of acquired projections. As discussed above, operation of the imaging system 36 may acquire the plurality of projections, such as with the slotted filter assembly 260. Accordingly, the imaging system 36 may generate projections that are based upon x-rays detected by the detector 78.

The x-ray projections may be acquired at the detector 78 with each of the three slots that generate the respective fans 440, 444, 448. Each of the three fans 440, 444, and 448 will generate three separate series of images or projections 560, 564, 568, respectively. Each of the series of projections includes a plurality of projections that are acquired substantially simultaneously as sets of projections through the slotted filter 300 when the SDU 98 is at a single position. For example, the first series 560 may include a first image slice 560i that will be acquired at the same position of the SDU 98 as a first image slice 564i and 568i respective to each of the fans 440, 444, 448. As the SDU 98 moves in the selected direction, such as along the axis 106 in the direction of the arrow 114, a plurality of projections is acquired through each of the slots 340-348 due to each of the fans 440, 444, 448. Accordingly, three series 560, 564, 568 of projections are acquired due to movement of the imaging system 36 along a selected line scan. Thus, each of the slot projections may be made of or include a plurality of respective slot projection slices, 560i, 56ii, 56iii, etc.; 564i, 564ii, 564iii, etc., 568i, 568ii, 568iii, etc.

The series of projections 560, 564, 568 are the projections from each of the three slots. As discussed further herein, although each of the slots and the respective fans 440, 444, 448 are used to generate respective series of projections 560, 564, 568, all of the image projections may be used to generate the long view that is reconstructed. Accordingly, the input of the x-ray projections from all three slots may include input of all three series of projections 560, 564, 568 which may be analyzed or evaluated separately, in various portions of the reconstruction, and then combined to form the final long view, as discussed further herein. Each of the image slices for each of the series (e.g., 560i, 564i, and 569i) generally and/or substantially are free of parallax distortion due at least in part to the width of the slot 398 and the corresponding length 468 excited on the detector. Thus, the slices may be clearer and have less error or distortion due to the slice width 398.

The reconstruction may further include an input of a motion profile of the imaging system 36. The input of the motion profile of the imaging system may include the distance traveled, time of distance traveled, distance between acquisition of projections, and other motion information regarding the imaging system 36. The motion profile information may be used to determine and evaluate the relative positions of the projections for reconstruction, as discussed herein.

In a first instance, according to various embodiments, the intermediate projection 610, 614, and 618 may be made based on the respective slot slice projections. The intermediate projections 610-618 may also be referred to as slot or intermediate films or images. The intermediate reconstructions may be substantially automatic by executing selected instructions with one or more of the processor modules or systems. The intermediate images may be made at a selected focus plane and may be generated for each of the series 560, 564, 568, as illustrated in FIG. 5. Accordingly, a first intermediate image 610 may be generated based upon the first series of projections 560. A second intermediate image 614 may be based upon the series of projections 564 and a third intermediate image 618 may be based upon the third series of projections 568. Each of the intermediate images 610, 614, 618 may be stitched together using generally known techniques such as image blending, registration, and view manipulations. These may include blending various portions of images that are near matches (e.g., determined to be similar portions) to achieve continuity. Registration includes matching or identifying identical portions of two or more images. Manipulations allow for altering different images or portions thereof, as discussed herein.

The plurality of projections, also referred to as image data portions, in each of the series or sets, such as the first series 560, are taken at a selected rate as the SDU 98 moves relative to the subject 28. As illustrated in FIG. 5, the subject 28 may include the spine 28s. As the SDU 98 moves, for example, the fan 440 is moved a selected distance, such as 1 centimeter (cm) per projection acquisition. Accordingly, each of the image projections, such as the image projection 560i, may be the width on the detector of the fan 440 and a second image projection 560ii may be 1 cm from the first image projection 560i and also the width of the fan 440 on the detector 78. A selected amount of overlap may occur between the two image projections 560i and 560ii that allows for stitching together into the intermediate projection or image 610, as is generally known in the art. Each of the series of projections 560, 564, 568 (which may each include image data portions), therefore, may be stitched together at the respective focus plane to generate the intermediate images 610, 614, 618. As discussed above, the focus plane may be initially set at 0 or arbitrarily set at 0 which is generally the isocenter of the imaging system 36 that acquired the plurality of projections 560, 564, 568. The intermediate images are generated based upon the plurality of projections due to movement of the SDU 98.

Each of the three intermediate images 610, 614, and 618 may then be combined to generate a first or initial long view or long film image 704. The generation or merging of the various intermediate images, such as each of the three intermediate images 610, 614, and 618, may include various steps and features. In various embodiments, an initial deformation of various features may be made when generating each of the three intermediate images 610, 614, and 618. As noted above, each of the three intermediate images 610, 614, and 618 may be generated based on a plurality of projections. Thus, each of the three intermediate images 610, 614, and 618 may include a similar or same feature (e.g., vertebrae). The amount of deformation to generate each of the three intermediate images 610, 614, and 618 may be determined and used in further merging procedures.

According to various embodiments, a weighting function 710 may be used to assist in the combining of the intermediate images 610, 614, and 618 to generate the long view image 704. The weighting function 710 is graphically illustrated in FIG. 6. A first weighting function for the first fan 440w illustrates that pixels or image portions may be weighted more for a selected portion (e.g., the left most portion as illustrated in FIG. 6) of the long view due to the position of the fan 440. The intermediate or central fan 444 may have the function 444w that will weight the pixels for the middle of the long view 704 more from the updated image 614u due to the position of the fan 444. Finally, the fan 448 may have the function 448w to weight the pixels of a selected portion (e.g., the right most portion as illustrated in FIG. 6) due to the position of the fan 448 in the long view 704. It is understood that other appropriate stitching functions may be used to generate the initial long view 704 and that the weighting function 710 is merely exemplary. Further, a greater weight may be given to the selected intermediate image 610, 614, and 618 that has the least deformation when generating the long view. Further, selected deformations, such as geometric deformations, may be made when generating the long view.

As also understood by one skilled in the art, with reference FIG. 1-6, the subject 28 may be imaged. In various embodiments, for example, a spine 28s of the subject 28 may be imaged. The acquisition of image data of the subject 28, such as the spine 28s, may be made by moving the imaging system 36, including the SDU 98, in a selected manner. For example, as discussed above, a linear or Z-axis image may be acquired of the spine 28s. As illustrated in FIG. 6, the source 74 may be moved with the slotted filter 300 to filter the cone 90 to generate the fans 440, 444, 448 that impinge on the spine 28s. The attenuated x-ray from the source of the SDU 98 may then reach the detector 78 for generation of a plurality of projections. As illustrated in FIG. 5A-6, each of the fans may project from the single source 74 and be formed due to the slotted filter 300 such that three individual fans for projections of the spine 28s on the detector 78. Each of the individual projections may be used to generate a single slot image projection that may be combined or stitched together, as discussed further herein. Further, as the SDU 98, including the source 74 and the detector 78, move along an axis such as the axis 106 of the subject 28 in plurality the slotted projections formed by the slotted filter 300.

Accordingly, the acquisition of the image data may be made by positioning the subject 28 relative to the SDU 98. The SDU 98 may then be operated to move, such as along the axis 106 of the subject 28, including the spine 28s, to acquire a plurality of image data projections of the subject 28. At a selected time, the various projections may be used for image identification, feature identification, registration or the like. For example, each of the slots of the filter 300 form or provide a plurality of projection slices for the respective slots. Returning reference to FIG. 6, for example, the slot 340 is used to generate the fan 440 and as the SDU 98 moves and provides or forms the plurality of slices 560, for each be referred to as 560i, 560ii. Each of these may be combined into a single slot film or intermediate image, such as in the first intermediate image 610. Accordingly, each of the other slots that form the other fans 440, 448 generate respective series of images 564, 568 that may be combined into respective slot films or intermediate images such as the second intermediate image 614 and a third intermediate image 618. It is understood, as discussed above, that the slot filter 300 may include a number different than three slots. Accordingly, the three slots and related intermediate images is merely exemplary.

Figure 7:
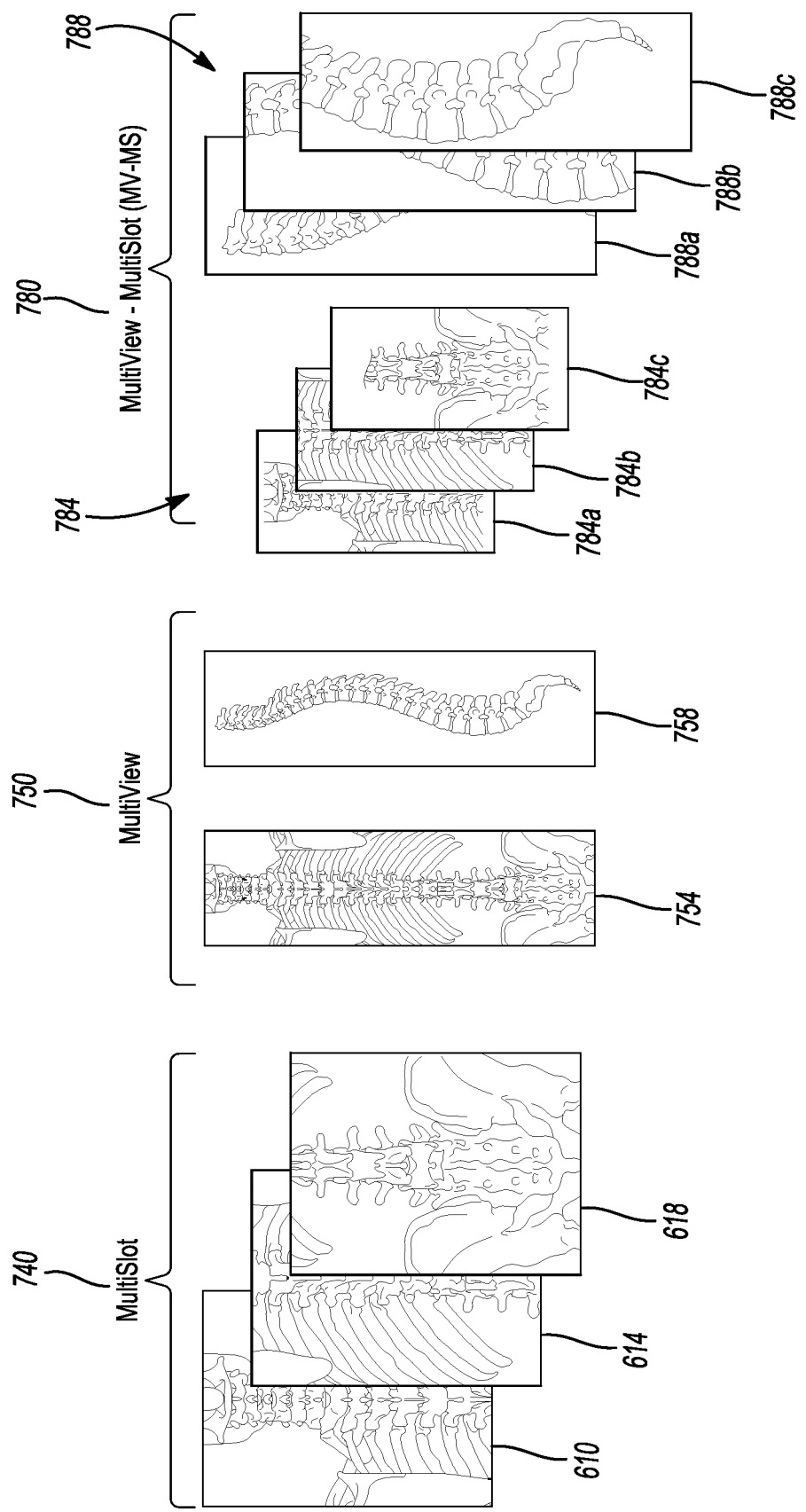
FIG. 7 is a schematic view of a plurality of types of image data acquisition.

Each of the slot films 610, 614, 618 may acquire a selected portion of the spine 28s, or other selected portion of the subject 28. Accordingly, each of the slot film or intermediate images may be combined to form a long film image 704, as illustrated in FIG. 7. The intermediate images 610, 614, 618 may overlap a selected amount, that may depend upon the size of the imaging system 36, the position of the subject 28 relative to the SDU 98, or other considerations. Nevertheless, each of the intermediate films 610, 614, 618 may include overlap regions. The amount of overlap may be any selected amount such as from greater than zero percent to about just less than 100 percent, including about 15 percent to about 75 percent. Accordingly, various portions of the subject 28, such as the spine 28s, may occur in more than one and/or all of the intermediate films 610, 614, 618. As discussed further herein, the appearance of the features in various ones of the different intermediate films may assist in identification of the features. Further, the overlap may allow for generation of the long film 704 in an appropriate manner. For example, the algorithm or system 710 may weight the amount or each pixel in each intermediate images 610, 614, 618 that is used when generating long films 704. Accordingly, each of the fans may have respective weights 440w, 444w, 448w that may change depending upon the translational position or position of the long film relative to the intermediate slices 610, 614, 618. Thus, the long film 704 may be generated with the intermediate films, as discussed above and disclosed in U.S. Pat. No. 10,881,371, incorporated herein by reference. The long film may be used to identify or have identified therein various features, as discussed further herein. Further, the long film may be registered to other acquired image data. Thus, the imaging system 36 may be used to acquire image data of the subject 28 at any appropriate time, such as during an intraoperative procedure or during an operative procedure and it may be used to identify features and/or registration to other image data of the subject 28.

Each of the intermediate images, such as the three intermediate images 610-618, may be made as projections relative to the subject in various manners such as an anterior to posterior (AP) view and/or a lateral view (e.g., from a left side to a right side) of the subject 28. The acquisition of an AP view may be by positioning the source and detector, as illustrated in FIG. 2, in solid lines to generate the AP projections through the subject 28. Lateral projections may be made by moving the source and detector to the phantom lines, as illustrated in FIG. 2. It is understood, however, that a plurality of views, such as more than two may also be acquired with the subject 28 by moving the source and detector to other positions relative to the subject 28. The discussion herein regarding an AP view and a lateral view, which together may be referred to as a multi-view or multiple views, is merely exemplary. It is understood, however, that a process may be performed with only these views.

Exemplary items and/or features of the image data may be acquired, classified, and/or used in selected procedures, such as those discussed further herein, based upon the types of image data acquired or using selected image data acquired. With reference, to FIG. 7, the various types of image data may include multi-slot or multiple-intermediate images or data 740. The multi-slot image data may include the various intermediate images such as the intermediate images 610, 614, 618. As discussed above, each of the multi-slot images 610-618 may be taken at a single perspective relative to the subjects 28. Accordingly, the multi-slot images may be based on a plurality of the slot images acquired through the selected slots of the filter member 300 but all be from a single viewer perspective, such as an AP view.

In addition, and/or alternatively thereto, a multi-view perspective 750 may also be acquired. The multiple view 750 may be include respective long films or stitch films from each of two perspectives, such as a long or stitched film from an AP perspective 754 and a long or stitched film from a lateral view 758. The multiple view 750, therefore, may be include two views that include stitched films or long film that may be stitched as discussed above, such as illustrated in FIG. 7.

Further, a combination of the multi-slot and multiple view may be used to generate a plurality of projections or views in a multi-view-multi-slot (MV-MS) projection 780. The MV-MS 780 may include a plurality of the slot films that are based upon the intermediate images from a selected view or perspective. Accordingly, three intermediate images may be from an AP view including image or perspective projections 784 that may include three slot film or projections from each of the slots or intermediate views such as a first 784*a*, a second 784*b* and third 784*c*. Each of the three projections may be the intermediate views from the perspective slots and to the selected view, such as an AP view. Similarly, three films may be generated from a lateral view including a plurality of lateral view film or intermediate images 788 each of the plurality may include the intermediate images or respective intermediate images at the lateral view from each of the respective slots including a first intermediate 788*a*, a second intermediate image 788*b*, and a third intermediate image view 788*c*. In the MV-MS, each of the respective intermediate films that would be generated from the respective slot images, such as the intermediate images 610-618, discussed above, may be acquired at each of the respective views including an AP and a lateral view. Therefore, for example, six projections or perspectives may be acquired in the MV-MS configuration.

Generally, according to various embodiments, the process or processes as discussed further herein allow for detection and/or classification of one or more features and image data. As discussed further herein, for example, image data may be acquired of a spine of a subject and identification or detection of features therein, such as vertebrae, may be made and classification of the detected features may be made, such as a specific identification of the specific vertebrae (e.g., first thoracic, or first lumbar).

As discussed above, image data may be acquired of the subject according to various procedures and techniques. The image data may be acquired of the subject such as with the imaging system, including the imaging system discussed above, to acquire a plurality of projections of the subject, such as through the slot filter 300. The image data, therefore, may be acquired of the subject at a plurality of perspectives either at a plurality of locations or at a single location including the plurality of perspectives through the slot filter 300. The multiple projections may be used for various procedures, such as identification and/or classification of features in the image data and/or registration of the image data to one or more other images and/or the subject 28. As discussed herein, identification of features in an image may be performed with the plurality projection in a robust and confident manner.

Figure 8:
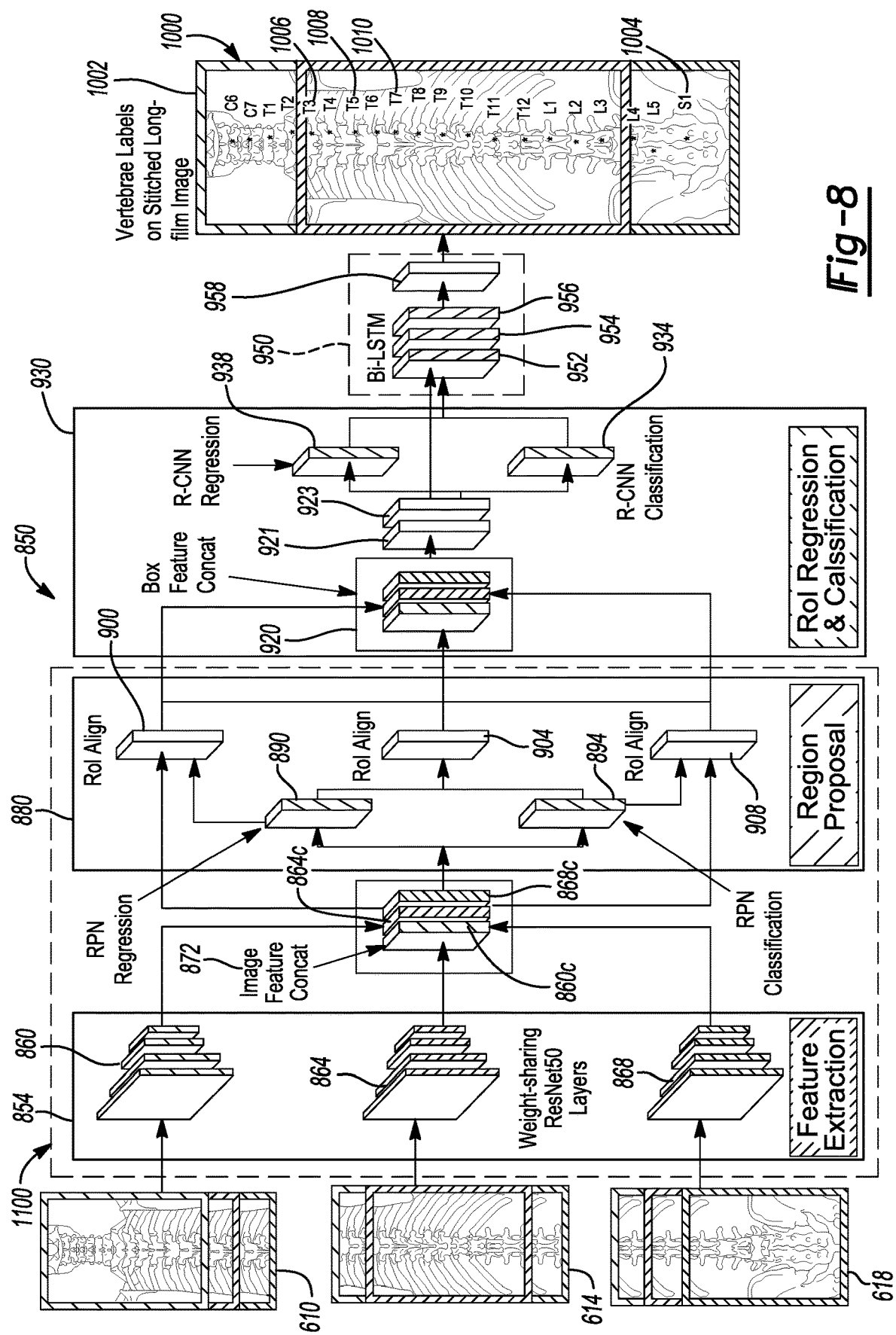
FIG. 8 is a flow diagram for a labeling and classification method, according to various embodiments.

With additional reference to FIG. 8, according to various embodiments, a multi-slot process or procedure 850, as illustrated, may be used to generate the multi-slot images 740. Initially, the multi-slot process or procedure 850 is understood to be carried out partially and/or entirely by executing instructions with a selected processor module or system. As discussed herein, at least portions of the multi-slot process or procedure 850 may include machine learning portions that are useful for assisting in identifying features (e.g., vertebra) and labeling the same (e.g., vertebra T1). It is understood, however, that various inputs may be provided manually (e.g., by a user with a selected input) including a starting portion or region or a label of one or more vertebra. In various embodiments, however, the process 850 may be substantially, including entirely, automatic to receive the input data 610, 614, 618 and output labeled long film 1000, as discussed herein.

As discussed above, each of the slots 340-348 of the slot filter 300 may be used to generate a plurality of image slides or projections that may be formed into separate slot images that are generated from each of the separate slots (also referred to as slot A, slot B, slot C) and therefore allow generation of the three slot images 610, 614, or 618. The three-slot images may be generated at any appropriate time, such as during a procedure including a surgical procedure on the subject. It is understood, however, that the image data may be acquired of the subject 28 at any appropriate time, such as prior to a procedure to assist in planning, etc. Nevertheless, the image data may also be saved and recalled for use in the procedure 850 and/or immediately accessed for the procedure 850. Nevertheless, the procedure 850 may be used to identify and label various portions in the image data, as discussed further herein.

According to various embodiments in the procedure 850 a feature extraction may occur in a first block step 854. The feature extraction may be performed on each of the three-slot projection or images and therefore generate three sets of extracted feature data for each of the separate slots. The feature extraction may extract any appropriate feature. As discussed herein, according to various embodiments, the feature extracted includes at least one and up to all of the vertebrae in the slot images 610, 614, and 618. It is understood that feature extraction, according to various embodiments, may include at least vertebra.

The feature extraction block 854 includes first convolutional layers 860 may be generated based upon the first slot image or projection 610, a second convolutional layers 864 may be generated based upon the second slot image or projection 614, and a third convolutional layers 868 may be formed and based on the third slot image or projection 618. Thus, the features may be extracted related to the individual slot image or projection 610-618 and used further in the procedure 850 to assist in the identification of portions therein. The extracted feature data is illustrated in blocks 872, as discussed herein.

The feature extraction performed in block 854 may be performed in any appropriate manner. For example, a neural-network or machine-learning system may be used to identify features in the feature extraction or detection block 854. In various embodiments, a machine-learning process RESNET 50 may be used on each of the image-slot projections to generate the feature extraction data in the portions that may be formed as convolutional layers 860, 864, 868 relating to each of the slot projections 610-618, respectively. It is understood, however, that any appropriate feature extraction process may be used and RESNET 50 (also referred to as residual) it is merely exemplary for the procedure 850.

Further, the features extracted may be determined according to the procedure 850, which may be a complex multi-step machine learning process and/or may be manually identified or set by the user. In various embodiments, a combination thereof may also be used such as training the RESNET 50 with a selected number of features and/or identifying or labeling features in a training data set for training the RESNET 50 that is applied to the selected data, such as the image data of a selected or current subject.

As illustrated in FIG. 8, the slot images 610-618 are linked to the subject and are generated through the slot filter 300. Generally, the slot filter 300 is at a single position and three slot image or projections are generated through each of the respective slots. These projections from each of the respective slots are then placed together into the single slot image projections 610-618 for each of the respective slots. Thus, slot image 610 may be for all projections from slot 340, slot image 614 from the slot projections 344, and the image 618 from the projections through slot 348. The separate slots projections are each of the position that is used to acquire one portion of the slot images. The separate slot projections are generally formed at a known angle relative to one another, such as about zero to about 10 degrees apart, including about seven degrees between each of the projections, as illustrated in FIG. 4A thus creating a distance or angular distance 472 between projections of each slot 340-348 at a single position of the filter 300. This allows each of the projections or slot portions to be at known positions relative to one another. Moreover, due to the positioning of the imaging system, including the slot filter 300 for generation of the plurality of slot film images, the slot films may overlap each other a selected amount. Accordingly, as illustrated in FIG. 8, the first slot image 610 may overlap a portion of the second slot image 614 and/or the third slot image 618. It is understood, however, that the feature extraction may occur in each of the separate slot images but may be related to each other due to the overlap of the generation of collection of the slot images relative to the subject.

The feature extraction process in block 854, including the image data (e.g., any layers thereof in the machine learning process) may be concatenated to form an image feature concatenate, also referred to as concatenated feature maps, in block 872. The image feature concatenate in block 872, as noted above, may include each of the features that are extracted from the slot images 610-618 as the various slot images may overlap at least a selected amount (including a known amount). The concatenated sets may include one for each of the feature extraction sets and referred to respectively as the concatenated layers 860c, 864c, and 868c. Therefore, the features in the respective slot images 610-618 may be generated as a concatenated feature map or a single concatenated feature maps from the three separate input slot images 610-618.

With the concatenated feature maps from block 872, a region proposal, which may include one or more regions, may be made in block 880. The region proposals may be related to the image data in the concatenated feature maps for identification of selected features or elements in the image data. The region proposals may be used for a region-based convolutional neural network (also referred to as an R-CNN). Thus, the regions identified or selected in the region proposal block 880 may be used for the R-CNN or appropriate machine learning system to identify the features in the image data, as discussed further herein.

Following and performed on the concatenated image feature map 872 may be a region proposal in the region proposal box 880. In the region proposal section or module 880 of the procedure 850, a region proposal regression process may occur in block 890 and a region proposal classification may be performed in block 894. Each of these processes, the region proposal regression 890 and region proposal classification 894, are performed on the concatenated feature map from block 872. Accordingly, the regression and classification occur on all three of these slot films 610-618, simultaneously. This may, among other aspects allow for creation of a region proposal for the projection of the same vertebra on all three slot films in a joint manner so that proposals across different slot films can be associated, as discussed herein.

Moreover, the concatenated feature maps 872 may be more efficiently operated on, as padding may be performed or used to ensure a similar number of features in each slot image 610-618 as each of the portions as the slot filter 300 may generate image data beyond the bounds of the slot films generated through the other slots. For example, as illustrated and discussed above, the slot relating to the slot film 618 may be padded with image data or pixels from the other slot films to ensure that the same vertebrae levels are covered amongst each of these slot film projections.

A classification may be used to classify the features extracted in the feature extraction block 854. The classification may be based upon training classifications and may include, for example, vertebrae, surgical instruments in an image, soft tissue or background features, or other appropriate classifications. In various embodiments, for example, a vertebra may be identified and classified in the image as separate from all other background information. In various embodiments surgical instruments, such as in implant (e.g., a screw), may also and/or alternatively be classified in the image.

A region proposal network (RPN) regression 890 and a RPN classification network 894 may be performed to assist in identify or evaluating various features identified in the respective image data or images. In the regression, understanding that the slot film may be substantially two-dimensional image data, various regressor values may be used to evaluate and/or adjust proposals. The regressors may be used to align the region proposals to the vertebra. In various embodiments, the proposals may be rough estimations of the location and size of the vertebra. They may overlap, but the proposal may not locate exactly on the vertebra. The regressors are used to make small adjustments to better fit the proposals bounding box to the vertebra. Each of the outputs from the RPN regression 890 and the RPN classification 894 may be used to evaluate various regions in the respective slot films and the RPN classification 894 may be used to identify foreground areas including proposals that are likely to contain vertebra. Accordingly, in the region proposal in block 880, a region of interest (ROI) alignment may occur to each of the slot films in respective alignment boxes 900, 904, 908.

To assist in the alignment, however, the RPN classification in block 894 and the RPN regression in block 890 may be used. The regression, as discussed above, may include regressors to identify a position of a bounding box within the respective image or image data, a size of the bounding box within the image data, and a distance between projections of neighboring slot films.

The regressor data points or values may include five regressors, as discussed herein. Two regressors include "$\Delta x$" and "$\Delta y$" that denote differences in coordinates relative to the noted distance of centroids of an identified object or feature from the ground truth. Two regressors "$\Delta w$" and "$\Delta h$" denote a width and a height from a ground truth box. A fifth regressor "s" is a distance between projections of neighboring slot films. The regressor values may be used to identify or evaluating the various features, such as centroids of individual vertebrae within the image data. As discussed above, for example, the slot films 610-618 may be of a spine of a subject and the identified features may include vertebrae. Accordingly, bounding boxes in respect of centroids of vertebrae may be identified and the above identified values may be used to identify the features or a bounding box of feature within the image.

In various embodiments, a single anchor box in an input image may be transformed into a group of three proposals in each of the slot images 610-618. The proposals may be assisted by a given and known distance of each of the slot images 610-618 from one another (i.e., based upon the known distance between the slots in the slot filter 300) and allowed or used to generate three proposals in each of the separate slot images 610-618 given the known distance. In other words, the proposals can be generated from the same anchor box is based on the fact that the distance between projection on slot film A and B is equal to the distance between slot film B and C. The distance between proposals within the same group may be unknown in the projection images and is part of the prediction from the network (the fifth regress s).

Once the RPN regression and classification have been formed, the regions are aligned in the ROI alignment blocks 900-908. The ROI blocks are then concatenated into the set for an ROI regression and classification process 930. The ROI aligned regions are concatenated in the ROI box concatenate block 920 and may then be classified in block 930 including with a region-based convolutional neural network (R-CNN) classification in block 934 and a R-CNN regression in block 938. Two fully connected layers 921, 923 with ReLU activations are used to map the proceeding concatenated box features 920 to intermediate representation for the R-CNN regression 938 and classification 934 that follow. In various embodiments, there may be three inputs given the input concatenated feature boxes 920, as illustrated in FIG. 8. Similar regressor terms may be used to perform the regression in the R-CNN regression block 938 and the R-CNN classification 934 may then be performed or may also be performed, such as substantially simultaneously, to perform a classification of the features in the image data. The R-CNN process 930 may allow for output of classification of the features, such as vertebrae, in the image data.

In addition to the classification in the classification block 930, according to various embodiments, an additional module may assist in identifying or confirming identification or classification of the features in a confirmation block 950, which may also be referred to as a bi-directional long-short term memory (Bi-LSTM) module. The confirmation module 950 may be a module to assist in confirming and ensuring appropriate classification of the features, such as the vertebrae in the procedure 850. As illustrated in FIG. 8, the final long film may be a two-dimensional long film 1000, such as the two-dimensional long film 704 as illustrated in FIG. 6. The long film 1000, however, may include the classification of the features in the image data. For example, each of the vertebrae may be labeled in the long film 1000 that may be otherwise labeled in each of the slot films 610-618, but through the process 850 are labeled in the long film 1000. Therefore, the labeled long film 1000 may include labels of selected vertebrae such as from a sixth cervical vertebra 1002 to a first sacral vertebra 1004. It is understood, however, that any appropriate vertebrae may be classified and identified within the image 1000. Moreover, the image may be of any appropriate portion of the anatomy of a subject in portions therein may be labeled, such as a training of the process 850 that then is used to classify a current or test subject image. The long film 1000, therefore, include portions of each of the slot films that may be overlapped and/or stitched together, as discussed above.

To assist in the proper classification of the selected features, the confirmation block 950 may be used, including the Bi-LSTM process, as discussed further herein. The Bi-LSTM module 950 allows for contextual classification of selected features. For example, in the spine of a subject the label of a specific vertebrae is correct, generally, only when correct relative to adjacent vertebrae. For example, in a spine including appropriate adjacent vertebrae a third thoracic vertebrae will only exist between the second thoracic vertebrae and the fourth thoracic vertebrae. Accordingly, as illustrated in FIG. 8, the vertebrae T3 1006, the fourth thoracic vertebrae T4 1008 and the fifth thoracic vertebrae T5 1010 will only occur in that specific order from a superior position in the image to an inferior position in the image. As the superior and inferior positions in the images are known based upon on the collection of the image data, including the slot films 610-618, the specific order of adjacent vertebrae may also be used. Accordingly, this known order may be used to assist in confirming and/or determining classification of vertebrae in the Bi-LSTM module 950.

Generally, the confirmation module may also be referred to as a recurrent module that may be used following the classification in the classification module 930. It is understood, according to various embodiments, that the confirmation of recurrent module 950 is optional and need not be required for classifying the selected features in the image data. It is understood, however, that the process 850 may be able to classify the vertebra even when one is missing or replaced with an implant is appropriately trained.

The long or vertical information regarding the position of the vertebrae within the image may be used to assist in the confirmation 950. Accordingly, after the classification of features, such as the vertebrae classifications, the vector information regarding the classification of the vertebrae may then be used and fed in to three Bi-LSTM layers 952, 954 and 956 followed by final linear layer 958. It is understood, however, that any appropriate number of layers may be used, the three bi-directional layers and the final single linear layer is merely exemplary. The confirmation module 950 allows for a learning of a sequential relationship of other vertebrae within the spine. In other words, as discussed above, the sequential limitation regarding the identification or classification of specific vertebrae may be used to assist in confirming or appropriately classifying vertebrae within the image.

The recurrent module or confirmation module 950 may allow for a loss function "L" to be expressed as Equation 1:

$$L = \lambda_1 L_{cls}^{RPN} + \lambda_2 L_{reg}^{RPN} + \lambda_3 L_{cls}^{RCNN} + \lambda_4 L_{reg}^{RCNN} + \lambda_5 L_{cls}^{LSTM}$$

In Equation 1, a weighted loss regarding classification losses $L_{cls}$ with respect to ground truth labels and regression losses $L_{reg}$ are computed using a smooth L loss function with respect to ground truth regressors. The weight factors "$\lambda$" are included to balance losses of the different terms. In various embodiments, $\lambda\_1=\lambda\_2=\lambda\_3=\lambda\_4=1$ and $\lambda\_5=0.1$, where each is a loss function weighting term related to RPN classification ($\lambda\_1$), RPN regression ($\lambda\_2$), RCNN classification ($\lambda\_3$), RCNN regression ($\lambda\_4$), and LSTM classification ($\lambda\_5$). In various embodiments, however, the coefficients A may be removed and all set equal to 1.

As discussed above, the process 850 may include a machine learning process including one or more modules that allow for determination of particular vertebrae and/or other features or objects in images and may output a single image based upon multiple input images. The output may be used in a selected procedure, such a spinal surgery performed on the subject 28. As illustrated in FIG. 1, the subject 28 may be positioned relative to the imaging system and/or placed in an operating theater for performing an operation or procedure thereon. Various procedures may include spinal fusions, disc replacements, vertebrae replacements, spinal rod placements, or other appropriate procedures. Accordingly, the procedure 850 may allow for identification and classification of vertebrae within the subject 28 for various purposes. For example, the final image 1000 including the selected label, such as the labels of the vertebrae 1002 and 1004 may allow for confirmation of a procedure, selection or identification or planning a procedure, or the like. Therefore, the image 1000 may be displayed for viewing by the user 24 as the image data 40 on the display device 44. In addition, the image 1000 may be acquired prior to a procedure and used for planning or the like.

The process 850 may include one or more convolutional neural networks, as discussed above. These may allow for identification of the various features in the image and generation of the long image 1000.

In addition, the procedure 850 may include various variations thereof to assist in selected outcomes, such as efficiency of calculation, computation of efficiency or speed, or the like. For example, the feature extraction block 854 and the region proposal block 880 may be performed as a single machine learning block 1100. The single procedure may include all of the inputs of the slot films 610-618 for feature extraction and region proposals therein in a single network or machine-learning process 1100. The procedure 850, therefore, may include an alternative and/or additional processing step or network step of combining the feature extraction and region proposal into a single network. The feature extraction and region proposal may also include or be performed with a convolutional neural network, or any appropriate machine learning procedure. Accordingly, in various embodiments, the procedure 850 may perform the output or produce the output 1000 with an appropriate input subject image based upon the procedure as noted above. In summary, the procedure 850 includes the feature extraction module 854, image feature concatenate 872, the region proposal module 880, box feature concatenate 920, and the ROI Regression and Classification 930 and/or the optional confirmation 950. In various embodiments, the procedure 850 may be performed sequentially and/or being combined together (at least in part) in a single module 1100.

Further, the procedure 850 may include a training phase that trains the procedure 850 of the machine learning process. In various embodiments, for example, a plurality of image data may be used to train the machine learning procedure 850 to achieve a selected output. In various embodiments, for example, a training data set may be generated based upon back projection of CT image data generated of a plurality of subjects. In various embodiments, a plurality of image data may be used to train the machine learning procedure 850 that is generated with the same imaging system as used for the selected output. After training of the procedure 850, a subject or current image data may be input into the trained network to achieve the selected output in the image data 1000. Accordingly, the machine learning procedure 850 may be trained to achieve the selected outcome, such as classification in the long film 1000. It is further understood that each current subject or new subject data may also be used as training data for training or improving the machine learning process 850 for future or later subject image data.

Figure 9:
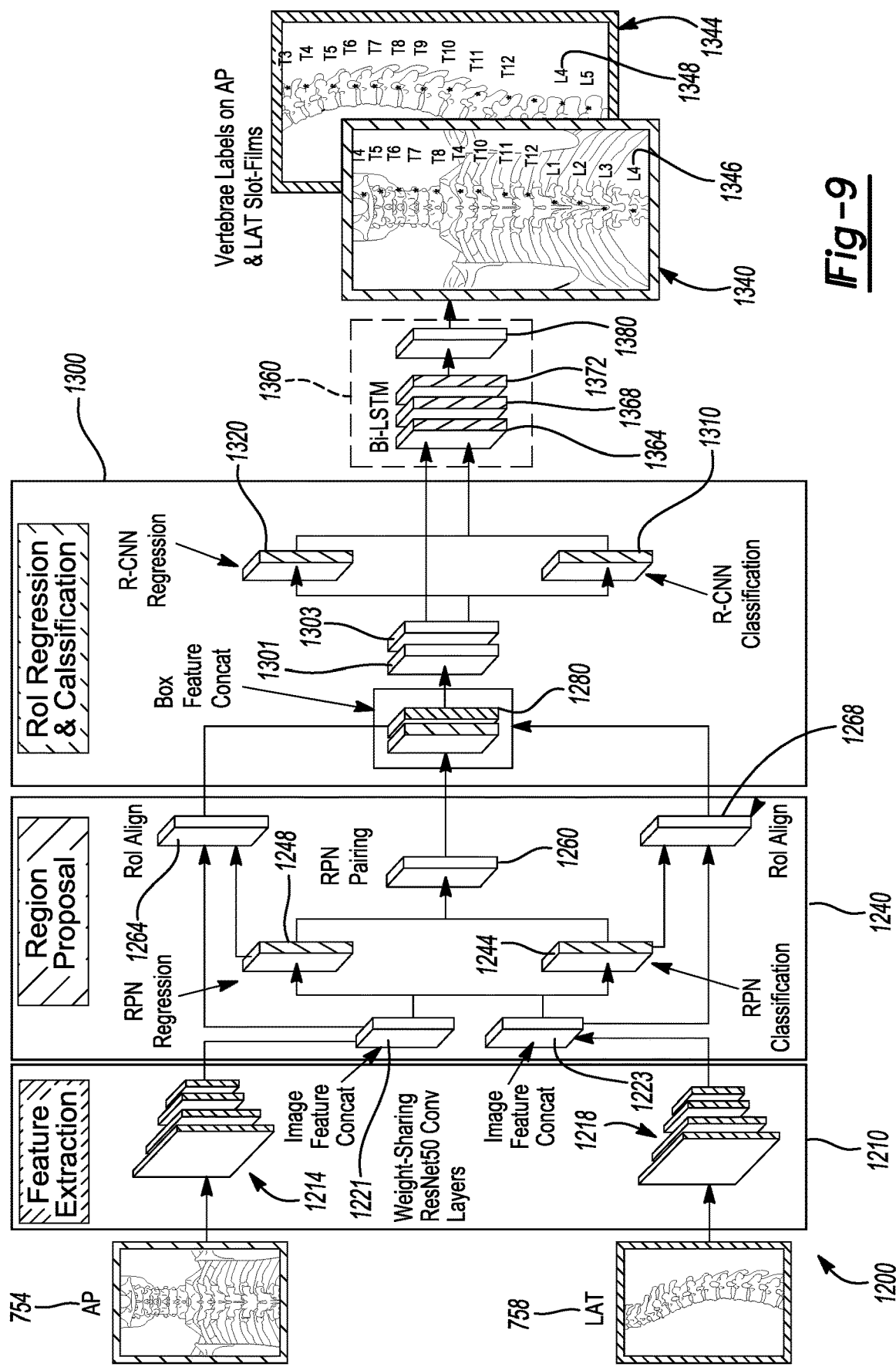
FIG. 9 is a flow diagram for a labeling and classification method, according to various embodiments.

Turning reference to FIG. 9, a procedure 1200 may be used to evaluate input image data for identifying, classifying, and/or confirming features in input image data. The procedure 1200 may include certain modules or portions similar to the procedure 850, as discussed above, and similar features or steps were not to be discussed in great detail here. The procedure 1200 may also be a machine learning system that evaluates input image data from multiple views. In this regard, the procedure 1200 is understood to be partially and/or entirely carried out by executing instructions with a selected processor module or system. As discussed herein, at least portions of the procedure 1200 may include machine learning portions that are useful for assisting in identifying features (e.g., vertebra) and labeling the same (e.g., vertebra T1). It is understood, however, that various inputs may be provided manually (e.g., by a user with a selected input) including a starting portion or region or a label of one or more vertebra. In various embodiments, however, the process 1200 may be substantially, including entirely, automatic to receive the input data 754, 758 and output labeled long film(s) 134, 1344 as discussed herein.

As discussed above, the image data acquired with the imaging system or any appropriate imaging system 30 may be collected at various positions relative to the subject 28, including an AP view that may include the input image or images 754 and a left-to-right, or vice versa, LAT view that may include the input image or images 758. The multi-view images 750, as discussed above in FIG. 7, may be acquired of the subject at any appropriate time. The images may be acquired before a procedure, during a procedure, or at the end of a procedure. In various embodiments, for example, the image data may be acquired of the subject for planning a procedure, confirming that a planned procedure has been performed, or confirming steps and/or planning for steps intermediate during a procedure.

The image data may be acquired of the subject 28 including the imaging system 30. The AP image 754 may include a plurality of slot images that are stitched together, as discussed above, but all taken in the AP perspective or view of the subject 28. Similarly, the lateral view 758 may include a plurality of slot images that are stitched together of the subject 28 that are all taken in the same lateral direction through the subject 28. The multi-view images 754, 758 may include a selected length that is the same (and/or cropped to be the same) of the subject but may be of different perspectives or views of the subject. Again, as illustrated in FIG. 2, an AP view may include an acquisition of the image data with the detector 78 in first position and a lateral view may include acquisition of image data with the detector 78 in a second position 78'. In various embodiments, for example, the AP view 754 and the lateral view 758 may be about 90 degrees offset from one another with respect to the subject 28. For example, the subject 28 may define a long axis 106 and the detector 78 is moved 90 degrees within the gantry 70 to acquire the two view images. The images 754, 758 may, however, be acquired the long view long axis 106 such that they are substantially long views or longitudinal views of the subject 28.

Thus, the procedure 1200 may include input of the AP view 754 and lateral view 758. It is understood, however, that the multiple views of the subject 28 may be any appropriate views and AP and lateral views are merely exemplary. The procedure 1200 may take as inputs multiple views relative to the subject that are offset relative to one another, such as by 50 degrees, 60 degrees, 120 degrees, or the like. Thus, the multiple views may allow for multiple views of the same portion of the subject 28, but the views need not be exactly or nearly 90 degrees offset from one another. Nevertheless, the procedure 1200 takes inputs from multiple views which may include the AP view 754 and the lateral view 758.

Thereafter, a feature extraction occurs in a feature extraction block 1210. The feature extraction block 1210 may be similar to the feature extraction block 854 discussed above, save for the distinctions discussed herein. The feature extraction may extract any appropriate feature. As discussed herein, according to various embodiments, the feature extracted includes at least one and up to all of the vertebrae in the views 754, 758. It is understood that feature extraction, according to various embodiments, may include at least vertebra.

The feature extraction block 1210 may include the RES-NET 50 network, as discussed above. The feature extraction in block 1210, however, may share weights between the input images. Thus, the multiple layers may be inspected to extract features in the input image or image data. As discussed above, for example, features may include vertebrae in the images acquired of the subject 28.

The feature extraction may occur in each of the images separately through the multiple layers represented by the feature extraction layers or convolutional layers 1214 for the AP input 754 and feature extraction layers or convolutional layers 1218 for the lateral input 758. Each of the image inputs 754, 758 may therefore, in the feature extraction module 1210, allow for or have separate features that are extracted therefrom. The convolutional layers 1214, 1218 may then be concatenated into extracted feature data also referred to as feature extraction maps 1221, 1223, respectively. Thus, the AP images data 754 may form feature extraction maps 1221 and the LAT images 758 may form feature extraction maps 1223.

The separate feature extraction for each of the input images may then be used in a region proposal module 1240. In the region proposal module 1240, a region proposal network (RPN) classification network 1244 may be performed and a RPN regression 1248 may also be performed in the perspective modules or blocks 1244, 1248. Due to the respective image dissimilarities, such as due to the differences due to the perspective or position relative to the subject of the acquisition, the RPN classification and regression may be performed separately on the separate extracted feature inputs 1214, 1218.

The differing views of the subject 28 generate image data including image portions or features that may be very different from one another due to the different perspectives and positions of the imaging device relative to the subject 28. The feature extraction in block 1210 and the region proposal in block 1240, therefore, may include procedures and modules that are applied to each of the input images separately. For example, the RPN classification module or block 1244 may be performed on both of the feature extracted data 1214 from the AP views 754 and the feature extracted portions 1218 from the lateral views 758. Thus, the classification of the features in the respective views 754, 758 may be performed separately on the different views. Similarly, the RPN regression in block 1248 may be performed separately on the differing views.

Further, regressors may be defined by eight different regressors that are again differentiated or separated from the two images including a first Δx, Δy, Δw, and Δh that relates to the AP view 754 and four of the same regressors that identify or relate to the lateral view 758. The regressors have the same definition as discussed above in relation to the procedure 850. The regressors may be used to align the region proposals to the vertebra. In various embodiments, the proposals may be rough estimations of the location and size of the vertebra. They may overlap, but the proposal may not locate exactly on the vertebra. The regressors are used to make small adjustments to better fit the proposals bounding box to the vertebra. Accordingly, the RPN classification in block 1244 and the RPN regression in block 1248 may be performed on the separate input image data at the different views including the AP view 754 and lateral view 758.

As discussed above, the image system 30 may acquire the image data of the subject 28 in a selected time or over a selected period. Further, the slot filter 300 that is used in assisting and generating the image data is at a known position relative to the detector 78. Therefore, the imaging system may operate to acquire image data of the subject 28 at a known longitudinal or vertical coordinate along the axis 106 of the subject 28. Therefore, each of the proposed regions or region bounding boxes may be at a known longitudinal coordinate and therefore may be paired in an RPN pairing module or block 1260. The region proposals may be paired in the RPN module 1260 with a joint objectness score computed as a sum of the objectness scores or the two proposals from the two inputs, respectively. Therefore, while the RPN regression and RPN classification may be performed on the input data separately due to the difference of the input image data, the proposals for regions and their respective image data may be paired due to the known longitudinal coordinate which may also be the coordinate of the image data.

With the RPN pairing in block 1260 a region of interest (ROI) alignment may be determined in the respective blocks or modules 1264 and 1268. The alignment may again occur due to the positioning of the respective of 23c proposal regions due to the known longitudinal position of the image data acquired of the subject 28.

The aligned image data from the AP and lateral views 754, 758, after having the proposed regions in the region proposal block 1240, are concatenated are in block 1280. The image data is concatenated via the known alignment, as discussed above. The concatenated image data in block 1280 may be used to perform a classification and regression analysis or network of the proposals in a classification block 1300. The classification of the regions may be performed similar to the classification as discussed above in an R-CNN classification in block 1310. Similarly, an R-CNN regression may occur in block 1320 of the concatenated image data from block 1280. Two fully connected layers 1301, 1303 with ReLU activations are used to map the proceeding concatenated box features 1280 to intermediate representation for the R-CNN regression and classification that follow. In various embodiments, there may be two inputs given the input concatenated feature boxes 1280, as illustrated in FIG. 9. After the classification and regression procedure in block 1300, the long films may be outputted as respective long film AP views 1340 and lateral views 1344. These long views 1340, 1344 may include respective classifications or labels based upon a procedure as discussed above, and a respective long view, such as a label of a fourth lumbar 1346 in the AP view 1340 and 1348 in the lateral view 1344.

Again, a confirmation or Bi-LSTM module 1360 may optionally be provided between the classification module 1300 and the output of the long views 1340, 1344. The Bi-LSTM module may be substantially similar to that as discussed above including a selected number of bi-directional layers, such as three bi-directional layers 1364, 1368 and 1372 and a linear layer 1380. These layers may be interconnected via the Bi-LSTM module or network 1360 to assist in confirming or enforcing a sequence on the identified or classified features. The Bi-LSTM module 1360, however, may perform or operate substantially similar to the Bi-LSTM module 1950, as discussed above.

Therefore, the multi-view process 1200 may be operated to label and identify features in image data in multiple views. Again, the multiple views may include (e.g., generated from) the multiple slot image or projections, as discussed above. Moreover, the multiple views may be input into the procedure 1200 to be used together, such as in the concatenated block 1280 and in the R-CNN classification and regression to classify features identified in the respective image data. Thus, the output image data, including the long films 1340, 1344, may include labels based upon the input data and the procedure 1200.

As discussed above, image analysis may be performed according to various networks on selected image data. The multi-slot analysis may be performed to identify or label features in the image data and a multi-view may also be used to label features in the image data, as discussed above and according to various embodiments. In addition, thereto, a combination may be performed on both a multi-view and a multi-slot in a multi-view-multi-slot (MV-MS) process 1400 to allow for identification in both a multi-view and a multi-slot image data. As discussed above and illustrated in FIG. 7, image data may be acquired from each of the slots and formed into the slot films taken along each of the perspectives, as an AP and a lateral view.

Figure 10:
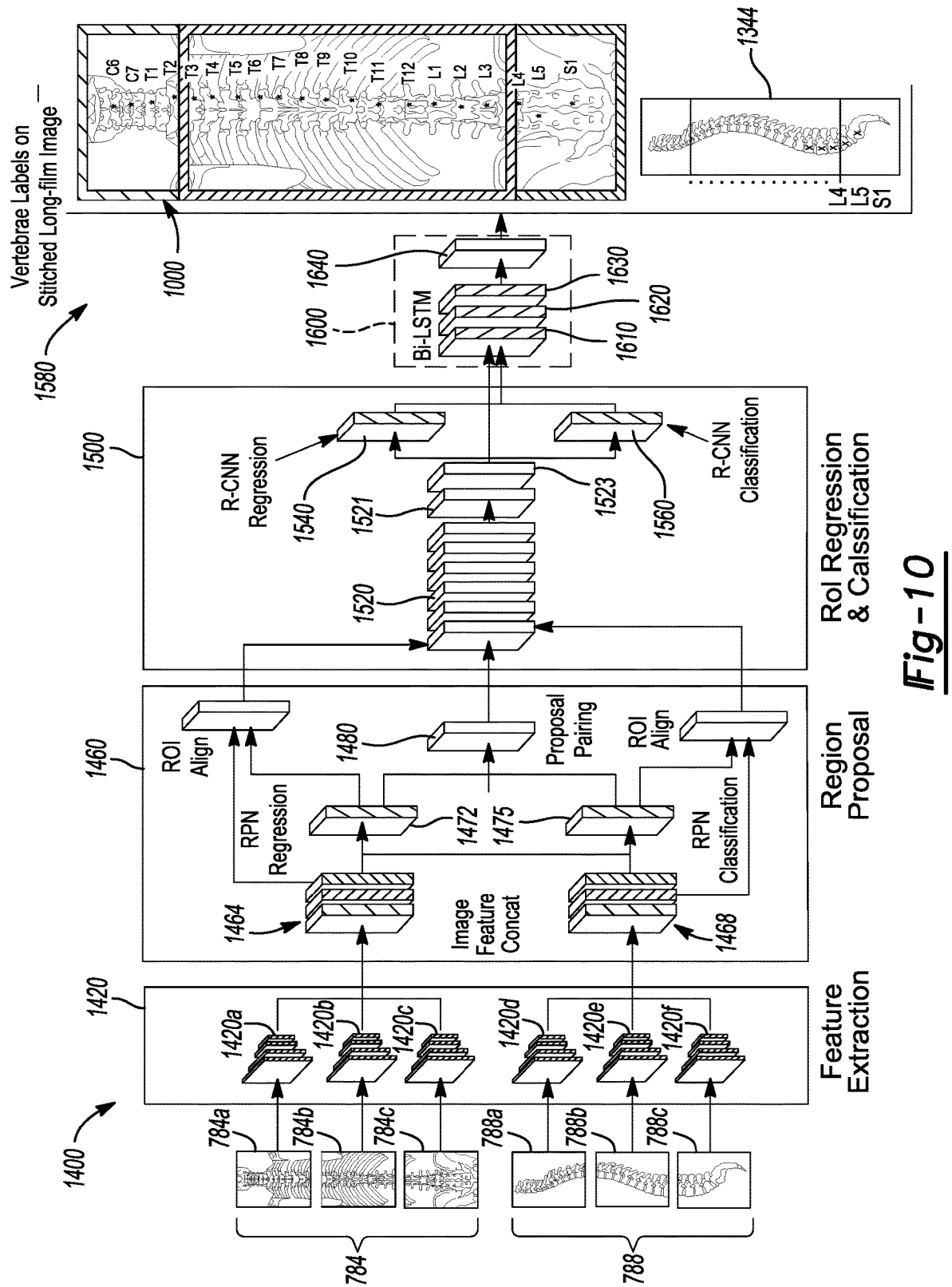
FIG. 10 is a flow diagram for a labeling and classification method, according to various embodiments.

With reference to FIG. 10, the MV-MS process or network 1400 may identify and/or classify or label features in the image data, as discussed further herein. Initially, the process 1400 is understood to be carried out partially and/or entirely by executing instructions with a selected processor module or system. As discussed herein, at least portions of the process 1400 may include machine learning portions that are useful for assisting in identifying features (e.g., vertebra) and labeling the same (e.g., vertebra T1). It is understood, however, that various inputs may be provided manually (e.g., by a user with a selected input) including a starting portion or region or a label of one or more vertebra. In various embodiments, however, the process 1400 may be substantially, including entirely, automatic to receive the input data 784, 788 and output labeled long films 1580, as discussed herein.

The input into the process 1400 can include each of the slot films taken from each of the respective slots of the slot filter 300, as discussed above, from multiple views. As illustrated in FIG. 10, three slots may use to generate three-slot films from each of the views including the AP view 784 and the lateral view 788 to generate the respective slot films 784a, b, and c and 788a, b, and c. The image data may be input to allow for feature extraction in each of the slot films from each view in feature extraction block 1420. As discussed above, the feature extraction may occur in an appropriate manner, such as using the RESNET 50 network system. The feature extraction in block 1420 may allow for extraction of features in each of the respective slot films 784a-c and 788a-c. Each of the respective slot films may have a respective convolutional layers 1420a, 1420b, 1420c, 1420d, 1420e, 1420f. Thus, the feature extraction may occur in each of the individual slot films and for each of the respective views acquired of the subject 28.

Following the feature extraction in each of the respective slot views, a region proposal block 1460 occurs. In the region proposal block 1460, a region proposal may be made in concatenated feature maps based on the views, including a first concatenated feature map also referred to as a feature extraction maps 1464 for the AP view and a second concatenated feature map 1468 for the lateral view. Each of the concatenated feature maps 1464, 1468 include three feature maps that relate to the same view for each of the respective slot films of the respective vies 784, 788. The region proposal 1460 may include a region proposal network regression 1472 and a region proposal network classification 1476. The region proposal regression 1472 and the classification in block 1476 may be formed similar to that discussed above with the multi-view process 1200.

Accordingly, after the regression and classification 1472, 1476, a region proposal pairing may occur in block 1480, also similar to the process 1260 as discussed above. Thus, a total of six proposals for regions of interest may be generated for each of the slot views from the original input and paired in the process 1480. In various embodiments, the pairing in blocks 1480 and 1260 are essentially the same. Longitudinal coordinates of anchor boxes are used for pairing. The difference is that in the process 1260 one proposal box is generated from a given anchor box. In the process 1480 three proposals are generated from one anchor box, as described above.

Following the region proposal pairing in block 1480 and the region proposal block 1460, a region of interest regression and classification block 1500 may also be performed.

The region of interest regression and classification block 1500 may be similar to the regression and classification block as discussed above such as the regression and classification block 1300 in the process 1200. In the regression and classification block 1500, the six proposals are concatenated into a box feature concatenate 1520. The box feature concatenate 1520 may be similar to the box feature concatenate 1280, as discussed above.

The box feature concatenate 1520 may, therefore, be performed in a network or classified in a network also similar to that discussed above. For example, the box feature concatenate 1520 may be placed in a network including an R-CNN regression 1540 and an R-CNN classification 1560. Two fully connected layers 1521, 1523 with ReLU activations are used to map the proceeding concatenated box features 1520 to intermediate representation for the R-CNN regression 1540 and classification 1560 that follow. In various embodiments, there may be six inputs given the input concatenated feature boxes 1520, as illustrated in FIG. 10. The regression and classification may be similar to that discussed above, as well. The regression factors may, however, include a $\Delta x$, $\Delta y$, $\Delta w$, $\Delta h$, s, $\Delta x'$, $\Delta y'$, $\Delta w'$, $\Delta h'$, s'. Each of these regression factors relates to the respective views similar to that discussed above to the multi-view network. Further, the s, s' regressors may also be used given the multiple slot films of the MV-MS process 1400. In this manner, the regressors may be used for confirming the classification of each of the features identified in the region proposals. The regressors may be used to align the region proposals to the vertebra. In various embodiments, the proposals may be rough estimations of the location and size of the vertebra. They may overlap, but the proposal may not locate exactly on the vertebra. The regressors are used to make small adjustments to better fit the proposals bounding box to the vertebra. Therefore, the R-CNN may be applied to the concatenated box features 1520 to input classification in each of the views 780 so that views 1580 may include labels as discussed above. Accordingly, each of the views may include a respective label based upon the analysis of the process 1400.

It is understood that the various views may be combined using various combination techniques, such as morphing or stitching. Thus, the input image data may be used to identify features and labeled the same in output images 1580. As illustrated in FIG. 10, the label films may include one or more similar to the films discussed above. For example, the output may include a long film 1000 similar to the film 1000 discussed and illustrated in FIG. 8. The labeled film may, however be similar to the AP film 1340. Further, the output 1580 may include the long film of the LAT view 1344 similar to the output 1344 illustrated and described in FIG. 9.

Further, a confirmation block 1600 may be added including the Bi-LSTM procedure as discussed above. As discussed above, this may include a three bi-directional networks 1610, 1620 and 1630 and a single linear network 1640 for confirmation and/or applying a rigid or a predetermined order to the labels in the images. The confirmation or Bi-LSTM block 1600 may be used to assist in ensuring a proper or confirmation label of the features in the image data.

Accordingly, according to various embodiments, the input image data may be analyzed according to various procedures, such as a machine-learning process that may be used to label and identify images and input image data. The input image data may be acquired with selected imaging system such as the imaging system 30. The image data may be analyzed using the trained machine-learning process, according to the various procedures as discussed above. The various procedures may be used according to various types of input data, including that discussed above. For example, the slot films may be acquired individually and analyzed according to the machine-learning process 850. Additionally, and/or alternatively, multiple view image data may be analyzed according to the process 1200. Further, various combinations may be used and analyzed, such as according to the machine-learning process 1400. The various processes may include various steps and analysis, as discussed above, that may be performed by selected processor modules including those discussed above and as generally understood by those skilled in the art. Nevertheless, the output may include image data that may be displayed as images for use by the user to view labeled features in the image data. The labeled features may be used to assist in performing a procedure and/or a confirming a planned procedure as also discussed above.

Figure 11:
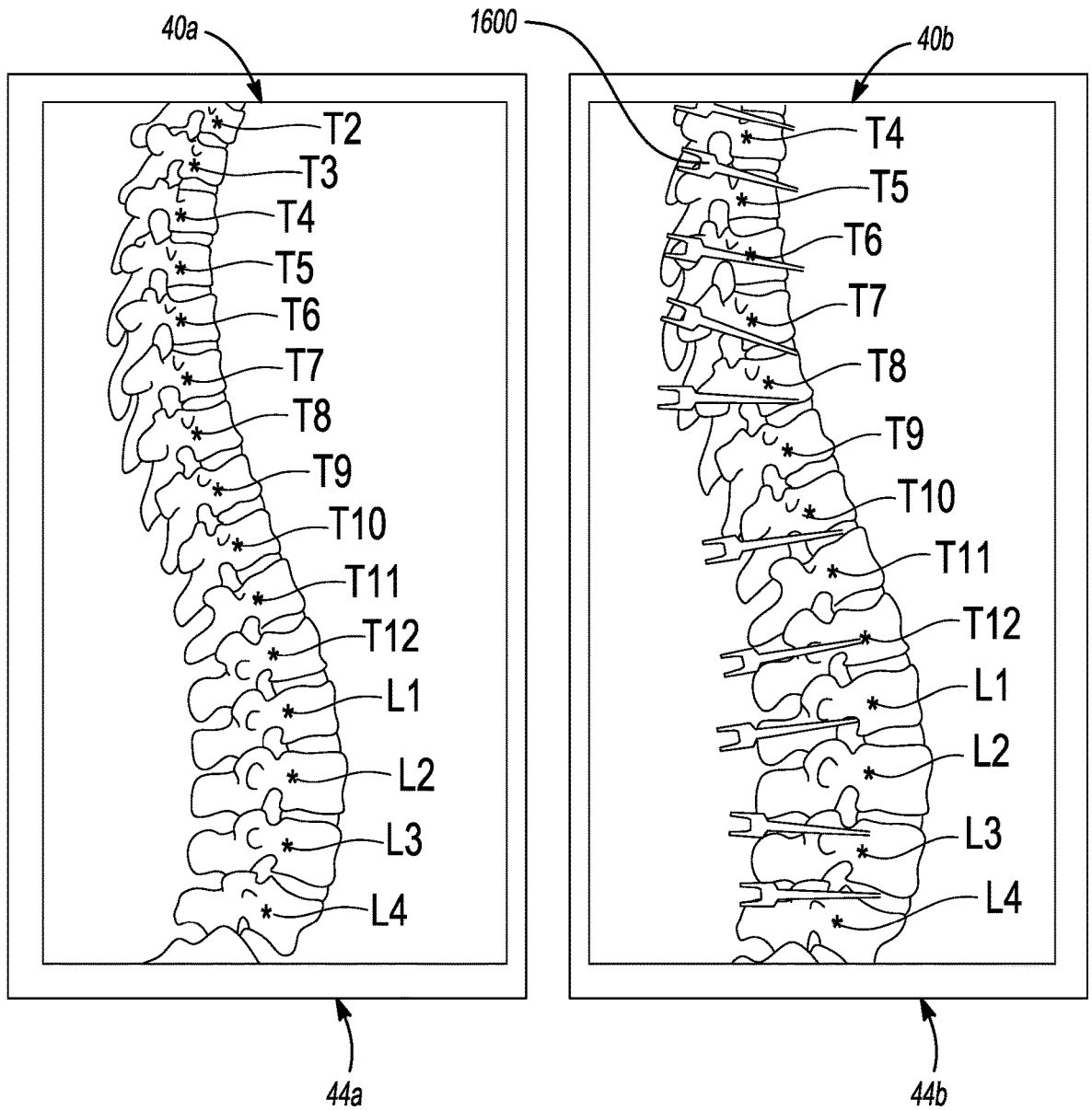
FIG. 11 is an exemplary illustration of a labeled and classified image.

Turning reference to FIG. 11, the labeled images, according to various embodiments as discussed above, may be displayed on the display device. Accordingly, the image data may be labeled image data for use by the user. For example, the display device, which may be in the appropriate display device such as a LCD display, LED display, CRT display, or the like. Nevertheless, the image may be in the labeled image, such as that discussed above. Thus, the image may include labels of one or more vertebrae in the image data that is displayed as the image. The images or image may include the labels that are determined according to the various embodiments, as discussed herein. In various embodiments, for example, the display device may display the image 40 that labels vertebrae when no surgical instruments are in place, such as the image 40*a*. The labels may identify or label centroids that have been identified in the image data and displayed with the display device 44*a*. In addition, and/or alternatively thereto, an image 40*b* may be displayed that labels vertebra even when a surgical instrument or other item is present in the image, such as a screw 1600. The screw 1600 may be any appropriate screw and is exemplary of an item in the image that may be present in addition to anatomical features in the image. Nevertheless, the labeled and displayed image may include features in addition to anatomical features of the subject 28. Thus, the user 24 may view the images with the display device 44*b* to assist in performing and/or confirming a procedure. The labeled portions of the image may be labeled with or without non-anatomical features, such as surgical instruments including implants.

The imaging system 30, or any appropriate imaging system, may be used to acquire image data of the subject 28. The image data may be analyzed, as discussed above, including labeling various features in the image data. The features may include anatomical portions in the image data, implants or surgical instruments in the image data or any other appropriate portion in the image data. According to various embodiments, various machine-learning systems, such as networks, may be trained to identify one or more features in the image data. As discussed above, the image data labels or identification may include centroids of vertebra. It is understood, however, that various portions of the image data may also be classified to be identified in the image data. Accordingly, during a selected procedure or at an appropriate time, image data may be acquired of the subject 28 with an appropriate imaging system, such as the imaging system 30, and features therein may be identified and/or labeled.

In various embodiments, a procedure may occur on the subject 28, such as placement of implants therein. Pre-acquired image data may be acquired of the subject, such as three-dimensional image data including a Computed Tomography (CT), Magnetic Resonance Imaging (MRI), or the like. The image data may be acquired prior to performing any portion of a procedure on the subject, such as for planning a procedure on the subject. The pre-acquired image data may be then used during a procedure to assist in performing the procedure such as navigating an instrument relative to the subject (e.g., a screw) and/or confirming a pre-planned procedure. In various embodiments, image data acquired of the subject during a procedure or after the acquisition of the initial or prior acquired image data may be registered to the prior or pre-acquired image data. For example, image data may be acquired with the imaging system 30 and may be registered to the pre-acquired image data according to various embodiments, including those discussed herein.

The registered image data may assist in allowing a user, such as the user surgeon 24, to understand a position of the subject at a given period of time after the acquisition of the initial pre-acquired image data. For example, the subject 28 may have moved and/or be repositioned for a procedure. Thus, image data acquired with the imaging system 30 may be registered to the pre-acquired image data.

The registration to the pre-acquired image data may include various portions as discussed further herein. Moreover, the registration of the image data to the pre-acquired image data may include registration of a large portion of the subject 28. For example, the imaging system 30 may acquire image data of the subject including several vertebrae, such as five or more, 10 or more, including about 10, 11, 12, 13, 14, or more vertebrae. As understood by one skilled in the art, the vertebrae may not be rigidly connected to one another and, therefore, may move relative to one another over time, such as between acquisition of pre-acquired data and acquisition of a current image data. Therefore, a registration process may and/or need to account for the possible movement. In various embodiments, therefore, a computer implemented system may be operated to account for and/or be flexible enough to account for movement of portions in the image data (e.g., vertebrae) relative to one another while being able to determine a registration between the prior acquired image data and the current image data.

As discussed above, and illustrated in various figures including FIG. 5, FIG. 6, and FIG. 11, a long film or long view image of the subject 28 may be generated with the system 20, including the imaging system 30 and/or various processing systems to stitch together various slot films and/or slot projections or the subject 28. Therefore, the long film may include a plurality of vertebrae of the subject 28 and various anatomical features included in the subject 28 including features of the vertebrae, other hard tissues (e.g., ribs, pelvis) and various soft tissues, such as cartilage, musculature, etc. The images or projections may be stitched or placed together, as discussed above. In various embodiments, the reconstruction from the three slots may include Tomosynthesis. This may allow for an image to be generated that is up to about 64 centimeters in length. The length may relate to a physical length of the film and/or a physical length of the object, such as the subject 28, being image that is included in the image data image in the long film.

The long film, or any appropriate projection image, including those as discussed above, may be registered to pre-acquired image data. The pre-acquired image data may include appropriate image data such a three-dimensional (3D) image data. That may be generated or acquired from various imaging modalities such as CT, MRI or the like. In various registration techniques, computer implemented algorithms and/or machine-learning processes may be used to perform the registration. For example, in various embodiments, a patient registration between the three-dimensional image and the intraoperative or intra-procedure or later acquired images, which may be two-dimensional images. A device registration may also be performed using known component registration methods. Various known component registration methods include those disclosed in U.S. Pat. No. 11,138,768, incorporated herein by a reference.

Figure 12:
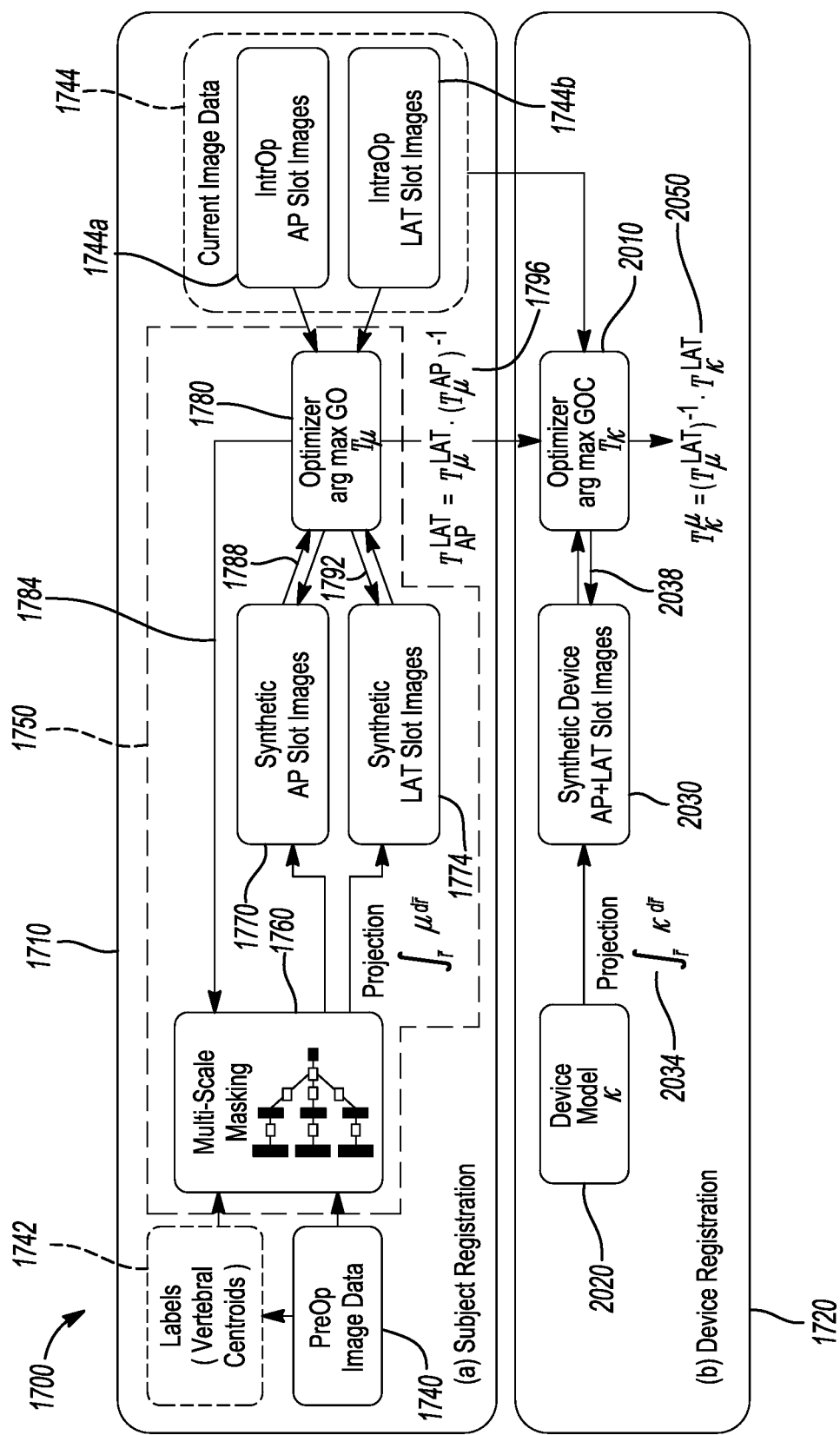
FIG. 12 is a flow diagram of a registration process, according to various embodiments.

With reference to FIG. 12, a registration procedure system 1700 is illustrated. The registration procedure 1700 may include two main portions that may be performed sequentially and/or separately. The registration method 1700 may include a patient registration 1710 and a device registration 1720. The patient registration 1710 may generally register the pre-acquired image data to a current or intraoperative image data of the subject, such as the subject 28. Therefore, the patient registration or subject registration 1710 may include registering image data of the subject 28 that is acquired at two different times. The second registration 1720 may be a device or instrument registration which may register a tract position of the instrument or an image position of the instrument to a determined position. In the device registration 1720, information regarding the instrument may be known and viewed, such as known components (e.g., a two-dimensional model, three-dimensional model, material selection or inclusion) used to assist in the registering or analyzing the image of the subject 28 including the instrument or device. Thus, the registration 1700 may include the two main registration steps or portion including the subject registration 1710 and the device registration 1720.

The registration 1700, including the two main registration steps or portion including the subject registration 1710 and the device registration 1720 is understood to be carried out partially and/or entirely by executing instructions with a selected processor module or system. As discussed herein, at least portions of the registration process may include machine learning portions that are useful for assisting in identifying features (e.g., vertebra) and/or masking the same. It is understood, however, that various inputs may be provided manually (e.g., by a user with a selected input) including a starting portion or region or a label of one or more vertebra. In various embodiments, however, the registration 1700 may be substantially, including entirely, automatic to receive input data, such as preoperative and current image data and output a registration therebetween.

With continuing reference to FIG. 12, the subject registration 1710 performs a registration (also referred to as morphing or non-rigid deformation) of prior acquired or preoperative image data 1740. The preoperative image data 1740 may be acquired at any time prior to a current image data or intraoperative image data. Moreover, the preoperative image data may be any appropriate type of image data including 2-dimension and/or 3-dimensional image data. In various embodiments, for example, the preoperative image data 1740 may include CT image data. The CT image data may be generated as a 3-dimensional image data of the subject 28. It is understood, however, that any appropriate image data may be acquired of the subject and preoperative CT image data is merely exemplary. Other types of image data include MRI image data, ultrasound image data, or the like. The preoperative image data 1740 is acquired prior to a current image data 1744, that is the current image data 1744 may be acquired of the subject 28 at any appropriate time, such as during an operative procedure, following a portion of an operative procedure or the like. The current image data 1744 is acquired of the subject and generally includes at least a portion of the subject that is included in the preoperative image data 1740. Thus, the current image data 1744 may include the image data, such as that discussed above. For example, the current image data 1744 may include image data that is labeled of the subject 28, such as identifying centroids of vertebral bodies in the image data. The labeled portions of the image may be labeled based upon the processes, as discussed above. Thus, the current image data may include identification of various portions within the image data such as the vertebrae, implants in the image, or other appropriate features. According to various embodiments, labels may be applied to portions of the image data and identification of vertebrae and/or centroids of vertebrae is merely exemplary.

The subject registration 1710 allows for a registration of the preoperative image data 1740 to current image data 1744 even if there has been a deformation or a change in relative position of various elements with the image data between the preoperative image data 1740 and the current image data 1744. For example, as discussed above, the preoperative image data 1740 and the current image data 1744 may include a plurality of vertebrae. The plurality of vertebrae may be the same vertebrae between the two image data sets 1740, 1744 but may be in different relative positions due to movement of the respective vertebrae during a time period between the acquisition of the preoperative image data 1740 and the current image data 1744. Nevertheless, a masking and optimization subroutine 1750 is operable to allow for registration between the preoperative image data 1740 and the current image data 1744. The current image data may also include or be referred to as intraoperative image data, as discussed above. The masking subroutine 1750 may include a machine-learning process to allow for training of a machine-learning process to then register the specific or patient specific preoperative image data 1740 to the current image data 1744.

The registration process 1750 includes the input of the current images 1744 that may include multi-view images, as discussed above. The multi-view images may include an AP slot image or film 1744a and a lateral slot image or film 1744b. Thus, the current image data 1744 may include a plurality of views such as an AP and a lateral view as discussed above. Moreover, as also discussed above, these views may be labeled according to the processes, such as the labeling process MV-MS 1400. Similarly, the preoperative image data 1740 may also be labeled, such as the labeling of vertebral centroid 1742. The labeling of the preoperative image data may be performed in any appropriate manner such as a manual process (e.g., user identified in the image), an automatic process (e.g., the processes disclosed above), or a combination thereof. In various embodiments, a machine-learning process may be used to identify and label the centroids or portions of the image in the preoperative image 1740. In various embodiments, a user, such as a surgeon, may alternatively or also identify the centroids or anatomical feature or other features in the preoperative image data and may be input as labels which may include the vertebral centroids 1742. Accordingly, the preoperative image data 1740 and the current image data 1744 may be input into the registration subprocess 1750.

In the registration subprocess, a further multi-scale mask subprocess 1760 may occur. As discussed herein, the multi-scale masking 1760 may allow for successively smaller portions of the input image data to be masked and registered to the current image data. The multi-scale masking allows for registration when there is deformation or relative change of features that are included in both the preoperative image data 1740 and the current image data 1744. For example, the various vertebrae, such as T4 and T5, may move relative to each other and be in different relative position between the preoperative image data 1740 and the current image data 1744. Thus, the multi-scale masking subroutine 1760, as discussed further herein, may be used to assist in the registration. In various embodiments, masking process 1760 may require only requires knowledge of the vertebral centroids as opposed to a pixel-wise segmentation. Thus, masking may also be referred to as a "local region of support".

The preoperative image data may then be used to generate synthetic slot images that may relate to the current image data including a synthetic AP slot image 1770 and a synthetic lateral slot image 1774. The synthetic images may be generated such as by forming projections through the input preoperative image data 1740 to generate the synthetic images 1770, 1774. The projection is generally computed by forward projection of the preoperative image 1740 through the image data at selected orientations to generate the synthetic slot images 1770, 1774.

The respective slot images may then be matched or registered to the current image data 1744 in an optimization subroutine 1780. The optimization subroutine may generally include an optimization of a gradient orientation (GO) metric that is optimization using a covariant matrix adaptation evolution strategy. Such strategies may include those disclosed by Hansen, N. and Ostermeier, A., "Completely derandomized self-adaptation in evolution strategies.," Evol. Comput. 9(2), 159-195 (2001).

The optimization procedure 1780 optimizes similarity between the synthetic slot images 1770, 1774 and the current image data 1744, that can include equivalent current slot data 1744a, 1744b. The optimization optimizes the similarity between synthetic slot images 1770, 1774 to the current image data 1744 to determine a registration of the preoperative image data 1740 (from which the synthetic slot images are generated 1770, 1774) to the current image data. Accordingly, the optimization process 1780 includes one or more feedback including a multi-scale feedback 1784, a synthetic AP slot image feedback 1788, and a synthetic lateral slot image feedback 1792. Thus, the synthetic slot images 1770, 1774 may be updated to optimize a match to the current image data 1744. The multi-scale masking 1760 may be updated, as discussed further herein, to optimize the synthetic slot images 1770, 1774 in the optimization subroutine 1780 to achieve an optimization similarity to the current image data 1744.

Therefore, the subject registration 1710 may output a transformation of the current image data, including the AP slot images 1744a and the lateral slot images 1744b, to one another and to the preoperative image data 1740 according to the transformation 1796. The transformation 1796 may then be output to the device registration process 1720 to register devices in the current image data to the preoperative image data 1740 to assist in following a procedure and/or confirming a plan for a procedure.

As discussed above, the subject registration process 1710 may include a subroutine 1750 to optimize the similarity or generation of synthetic slot images 1770, 1774 relative to the current image data 1744. As a part of the optimization subroutine 1750, the multi-scale masking 1760 subprocess is further carried out. In the multi-scale masking 1760 a plurality of masking steps and/or progression of masking steps occurs. With continued reference to FIG. 12 and additional reference to FIG. 13, the multi-scale masking subroutine 1760 will be described in further detail. It is understood that the multi-scale masking 1760 described in FIG. 13 and herein may and/or is incorporated into the optimization subroutine 1750, discussed above. Therefore, the multi-scale masking 1760 may be understood to be a part of the subject registration 1710.

The multi-scale masking (hereby referred to as masking) may occur in a plurality of stages or steps wherein each stage masks a selected number of vertebrae for generation of the synthetic slot images 1710, 1774 for the optimization in block 1780. It is understood that the illustration in FIG. 13 includes three stages referred to as stage K=1 1820, stage K=2 1824 and stage K=3 1826. Each of the stages 1820, 1824, and 1826 may be referred to as a selected number of vertebrae that are masked. It is also understood that the subject registration 1710 may refer to registration of patient subject images of a spinal column, as discussed herein. In various embodiments, however, the subject registration may include registration of a non-human subject and/or non-spinal elements in a human or animal subject. Accordingly, the reference herein to vertebrae is merely exemplary. For example, any appropriate identified feature or labeled feature in the images may be registered.

It is also understood that the three stages are also exemplary. More or fewer stages may be used. The selected number may be based upon a speed of computation, achievement of registration convergence time, confidence in registration, or other appropriate factors. For example, a greater number of stages may reduce the number of masked portions from stage to stage, while increasing computational time, but may achieve greater confidence in registration. Further, fewer stages may decrease computational time and increase the number of elements removed per stage but may have a reduced confidence in registration. It is understood, therefore, that an appropriate number of stages may be selected for various purposes.

In general, the multi-stage masking 1760 allows for registration and/or efficient registration between a first image and a second image where features are not at the same positions relative to one another between two images. For example, a preoperative image data 1740 may be acquired of the subject 28 at a period of time prior to an operative procedure, which may be proceeded by hours or days. Moreover, a subject may be moved to a convenient position for an operative procedure that is different than the position for acquiring the preoperative image data 1740. Accordingly, the current image data 1744 that may include intraoperative or post-operative images the image of the subject 28 may include features that are at different relative positions than in the preoperative images 1740. The masking procedure 1760 allows for achieving a registration between a preoperative image data 1740 and the current image data 1744 when the features are at different relative positions, such a due to movement of the subject 28.

The registration process 1710 allows for determining a transformation of the preoperative image data 1740 such that it matches or is similar to the intraoperative image data 1744. Accordingly, the transformation may include a mathematical definition of a change or transformation between the two image data and, as discussed further herein, may be directed to a plurality of vertebrae and for a single vertebrae, and sequentially from plurality to a single vertebrae. Therefore, a single vertebrae within the preoperative image data 1740 may be registered to a single vertebrae in the current image data 1744. The single vertebrae is generally defined or identified as the same vertebrae in both the preoperative image data 1740 and the current image data 1744. The registration allows the portions identified (e.g., segmented) in the first image to be overlayed (e.g., superimposed) on the same portion in the second image.

The preoperative image data may generally have labeled features therein that will be similar or identical to the labeled features in the current image data 1744. As discussed above, features may be labeled in the image data according to the various machine-learning processes. The machine-learning processes may be used to identify or label the features in the preoperative image data 1740 and/or the features in the current image data 1744. Therefore, the machine-learning procedures may be trained with preoperative image data or a selected type of preoperative image data such as CT, MRI, or the like. For example, the preoperative image data may be 3-dimensional image data while the current image data may be 2-dimensional image data. Further, the features in the preoperative image data may also be labeled by a user. For example, a user, such as a surgeon or technician, may identify vertebrae, including vertebral centroids, and label them in a preoperative image data. The features may also be identified by other appropriate mechanisms or algorithm such as using a neural network method for automatically labeling vertebrae in 3D images. Various techniques may also include those disclosed in Huang, Y., Uneri, A., Jones, C. K., Zhang, X., Ketcha, M. D., Aygun, N., Helm, P. A. and Siewerdsen, J. H., "3D vertebrae labeling in spine CT: An accurate, memory-efficient (Ortho2D) framework," Phys. Med. Biol. 66(12) (2021), incorporated herein by reference.

As an introduction, the masking process 1760 may end with the final stage where a single element, such as a vertebra, is a local region of support and may also be referred to as masked. The final stage 1826 may be a third stage as illustrated above. However, more stages or less stages may be used. Moreover, the final stage may be achieved after an intermediate stage where only one or two vertebrae are masked relative to the target vertebra as illustrated in step 1824. This may be preceded by a stage where a plurality of vertebrae may be masked. In various embodiments, in the first stage 1820 an entire range of view or field of view may be masked as a single element to initiate a rigid registration. It is understood that an identified feature within the full field of view, such as a labeled vertebra by a user in the 3-dimensional image, may be used to identify a target vertebra. Accordingly, a plurality of segments including vertebrae around the target vertebra may be masked together for the masking process 1760.

Further, it is understood that masking an entire field of view may mask a plurality of elements that may be later individually masked, such as in the individual mask step 1826. Accordingly, for example, if 15 vertebrae are identified the process 1760 may be carried out for each of the 15 vertebrae to allow a target (e.g., selected one or more) vertebra to be individually masked in the final stage 1826 for each vertebra identified in the input image data. Therefore, the procedure 1760 illustrated for a single exemplary element, such as a vertebra, is merely exemplary and may be carried out a number of times necessary for each element within an image.

Figure 13:
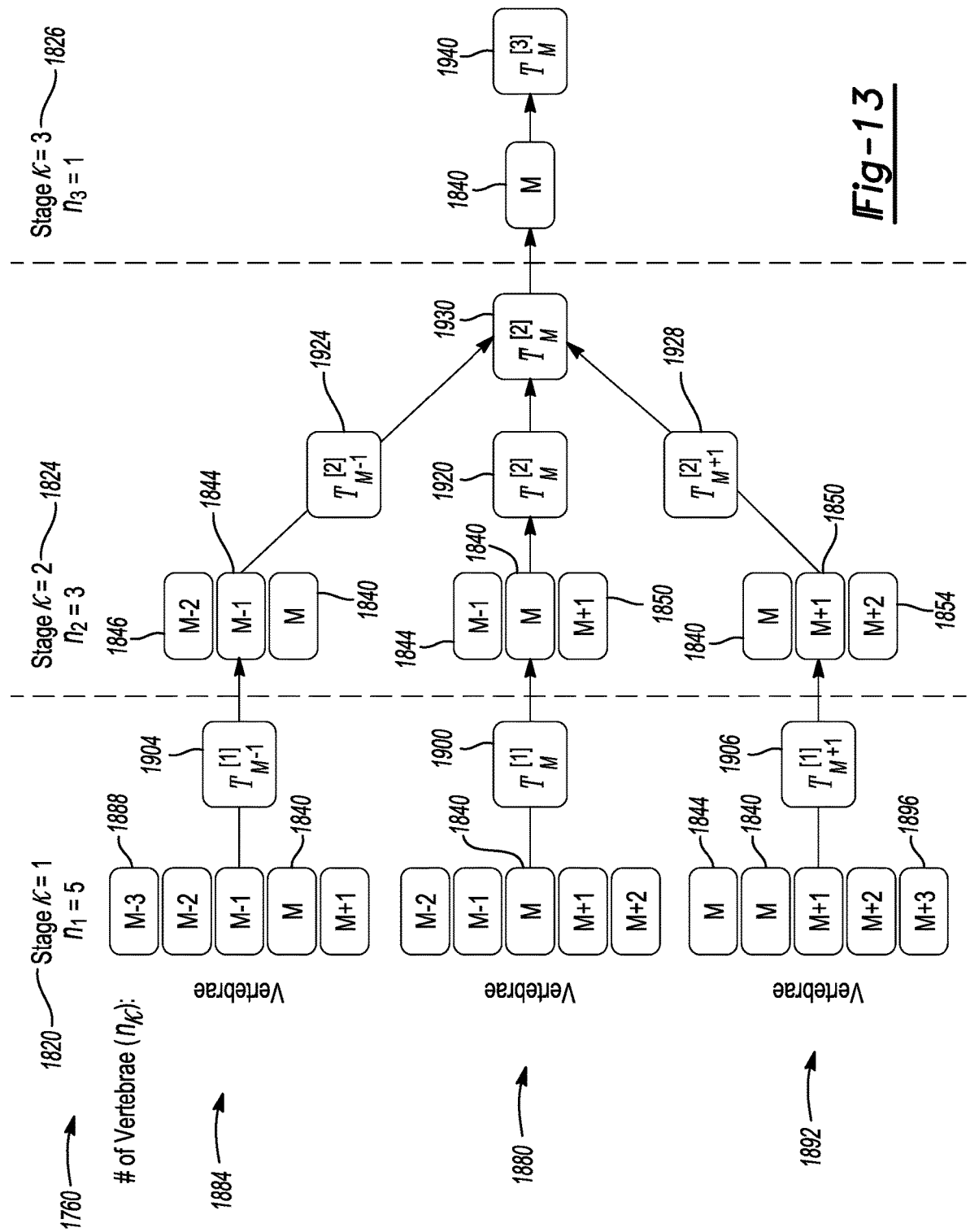
FIG. 13 is a tree diagram of a multi-scale masking process for registration, according to various embodiments.

The process of the multi-step masking 1760 will be described in greater detail with continuing reference to FIG. 13 and additional reference to FIG. 14. As noted above, the elements in the pre-operative data 1740 may be identified, such as with the vertebral centroids in block 1742. Accordingly, the identified features may also be segmented, such as the vertebra may be segmented within the pre-operative image data 1740. The pre-operative image data may then be rigidly registered to the current image data in a selected manner, such as discussed above, as exemplary illustrated in FIG. 14 in frame 1834. Therein, the pre-operative image data may be segmented or otherwise identified, such as identifying edges or boundaries, and illustrated relative to the current image data 1744. In the rigid registration illustration, the vertebral centroids 1742 may be identified as elements 1836 relative to the current image data 1744. It is understood, however, that the rigid transformation need not be illustrated and may simply be identified or created for the process 1700 and stored internally on a memory to be accessed by the processor.

The rigid transformation may allow for an initial placement of the vertebra or selected elements relative to the current image data 1744. Accordingly, at the first step 1820, five vertebrae may be masked relative to a selected vertebra, such as the vertebra L1 1840. Herein, while the vertebra L1 may be the patient vertebra, being registered, alone or with the other vertebra, for the generally discussion the specific member is identified as "M" and those superior and information relative there to as +n and −n, where "n" is the number away from the specific member M. The masked vertebra or selected vertebra in step 1820 may be masked relative to the selected or identified vertebra 1840 and in the appropriate number, such as including two superior and two inferior relative to the selected vertebra 1840. Accordingly, the selected vertebra elements may be generally referred to as the identified elements and a selected element plus or minus the identified element. In various embodiments, as illustrated in FIG. 14, specific vertebrae may be identified. In the current example, if the vertebra L1 is identified as the target vertebra 1840, the other four masked vertebrae may be include the two vertebrae immediately superior of the vertebra L1 (M) which may include two superior vertebra T12 (M+1) 1844 and T11 (M+2) 1846 and two inferior vertebra L2 (M−1) 1850 and L3 (M−2) 1854. It is understood, however, in various instances a spinal element may have been removed or fused and the vertebrae may not be the normal vertebrae. Nevertheless, in various embodiments, the adjacent vertebrae may include two superior and two inferior vertebrae, as noted above. In various embodiments, a selected number of vertebrae may include a total other than five and a different selected number of inferior and superior vertebrae. Further, as discussed herein, further sub-portions of the Steps K=1 and K=2 include different vertebrae masked relative to the target vertebrae.

The masks used in each of the stages 1820, 1824, 1826 of the masking process 1760 may be volumetric masks that are defined relative to the centroids 1742 in the pre-operative image data 1740. The centroids 1742 or appropriate labeled portions can be accomplished via manual methods (e.g., labeling by a surgeon) and/or by automatic methods, including those based on appearance models, probabilistic models, and convolutional neural networks as discussed in Klinder, T., Ostermann, J., Ehm, M., Franz, A., Kneser, R. and Lorenz, C., "Automated model-based vertebra detection, identification, and segmentation in CT images," Med. Image Anal. 13(3), 471-482 (2009); Schmidt, S., Kappes, J., Bergtholdt, M., Pekar, V., Dries, S., Bystrov, D. and Schnorr., C., "Spine Detection and Labeling Using a Parts-Based Graphical Model," Bienn. Int. Conf. Inf. Process. Med. Imaging, 122-133 (2007); Chen, Y., Gao, Y., Li, K., Zhao, L. and Zhao, J., "Vertebrae Identification and Localization Utilizing Fully Convolutional Networks and a Hidden Markov Model," IEEE Trans. Med. Imaging 39(2), 387-399 (2020); and/or Huang, Y., Uneri, A., Jones, C. K., Zhang, X., Ketcha, M. D., Aygun, N., Helm, P. A. and Siewerdsen, J. H., "3D vertebrae labeling in spine CT: An accurate, memory-efficient (Ortho2D) framework," Phys. Med. Biol. 66(12) (2021), all incorporated by reference.

In various embodiment, the masks may be defined in an appropriate manner, and the following are exemplary masks. A process of defining a volumetric mask with a 3-D spline curve fitted to the centroids in the pre-operative image data 1740 may be performed with no additional user input. Accordingly, the centroids may be defined and the masks may be defined relative thereto as a 3-D spline curve. A volume of the mask may generally be defined as 5 cm×5 cm×3.5 cm that define a volumetric region about the fitted curve. In various embodiments, thresholding may also be performed to remove non-bone tissue, such as defining an intensity to threshold for the bone. It is understood, however, that other appropriate thresholds and/or other appropriate volumetric regions or 2-D regions may be used to define masks for various types of image data. Further, the various steps 1820, 1824, 1826 may include cropping of the pre-operative image data 1740, the synthetic images 1770, 1774 therefrom due to the masking regions and/or the current image data 1744 to minimize memory usage regarding the target 1840 and the respective limited number of masked regions relative thereto.

In the masking procedure 1760, the target vertebrae 1840 masked in the step 1826 may include a process where an average is identified or used relative to a selected number of vertebrae relative to the target vertebrae 1840 in the prior two steps 1820, 1824. For example, in a main or primary path 1880 two superior and two inferior vertebrae may be identified. In a first auxiliary path 1884 one inferior and three superior vertebrae may be identified, including a further superior vertebra 1888. In a further auxiliary path 1892 a single selected superior vertebra 1884 may be identified and three inferior may be identified including a third inferior vertebrae 1896. Therefore, the primary and the auxiliary paths 1880-1892 may be used to generate information regarding a registration of the target vertebrae 1840 and the final single masking step 1826.

Accordingly, as illustrated in the process 1760, the final registration of the target vertebrae 1840 may include an average of three transformations that occur along the respective paths 1880, 1884, and 1892. The primary path 1880 initializes with five vertebrae two superior and two inferior to the target vertebrae 1840. The first and second auxiliary paths 1884, 1892 register the target vertebrae 1840 with different or including different vertebrae to register the target vertebrae 1840 to the current image data 1744. Therefore, after the initial step 1820 masking, the five vertebrae including the target vertebrae 1840, three respective transformations are generated to register the target vertebrae to the current image 1744 and for initialization of the second step 1824 including three vertebrae. In this manner, the primary path 1880 generates a primary transform 1900. The first auxiliary path 1884 generates a second transform 1904 and the second auxiliary path 1892 generates a third transform 1906. The respective transforms 1900-1906 initialize the registration and the second step 1824. Therefore, the initial transform 1820, as illustrated in FIG. 14, includes a registration that may have an error relative to the current image data for all of the vertebrae but may be minimized for the target vertebrae 1840. Further, the registration 1820 may be saved in a memory for access for further steps and/or displayed on a display device, as illustrated in FIG. 14. It is understood that it is not required to be displayed for the process 1760.

Following the initial transforms 1900-1906, the second stage k=2 1824 may occur with masking of the target vertebrae with only two vertebrae relative thereto. Accordingly, the target vertebrae 1840 is identified and masked along with two vertebrae relative thereto. In the primary path 1880, one inferior and one superior vertebra is masked 1850 and 1844. In the first auxiliary path 1884, the two superior vertebrae are masked 1844 and 1846 in addition to the target vertebrae 1840. In the third auxiliary pathway, the target vertebrae 1840 is masked with the two inferior vertebrae 1850 and 1854. Accordingly, the second stage 1824 masks three vertebrae in each of the three paths 1880-1892. Again, each of these allow for a transformation to register the target vertebrae 1840 to the current vertebrae, as illustrated in FIG. 14 at 1824. Each of the paths generates a respective transform including the primary path 1880 generating the transform 1920, the first auxiliary path generating the transform 1924 and the third auxiliary path 1892 generating the transform 1928. Again, each of the transforms 1920-1928 allow for a registration regarding the target vertebrae 1840 to the current image 1744 including information regarding the respective two other vertebrae.

Each of the three transforms 1920-1924 are averaged to a transform 1930. The average transform 1930 is an estimated transform that is computed by averaging a 3×1 translation vector along each degree of freedom (DOF) and a 3×3 rotation matrix. The average transform is computed using the arithmetic mean of each DOF, and the average rotation is calculated using the chordal L2 mean as disclosed in Hartley, R., Trumpf, J., Dai, Y. and Li, H., "Rotation averaging," Int. J. Comput. Vis. 103(3), 267-305 (2013), incorporated herein by reference. Therefore, the average transformation 1930 may be used to initialize the final step 1826 for generation of the transformation of the target vertebrae to the current image data 1744.

Figure 14:
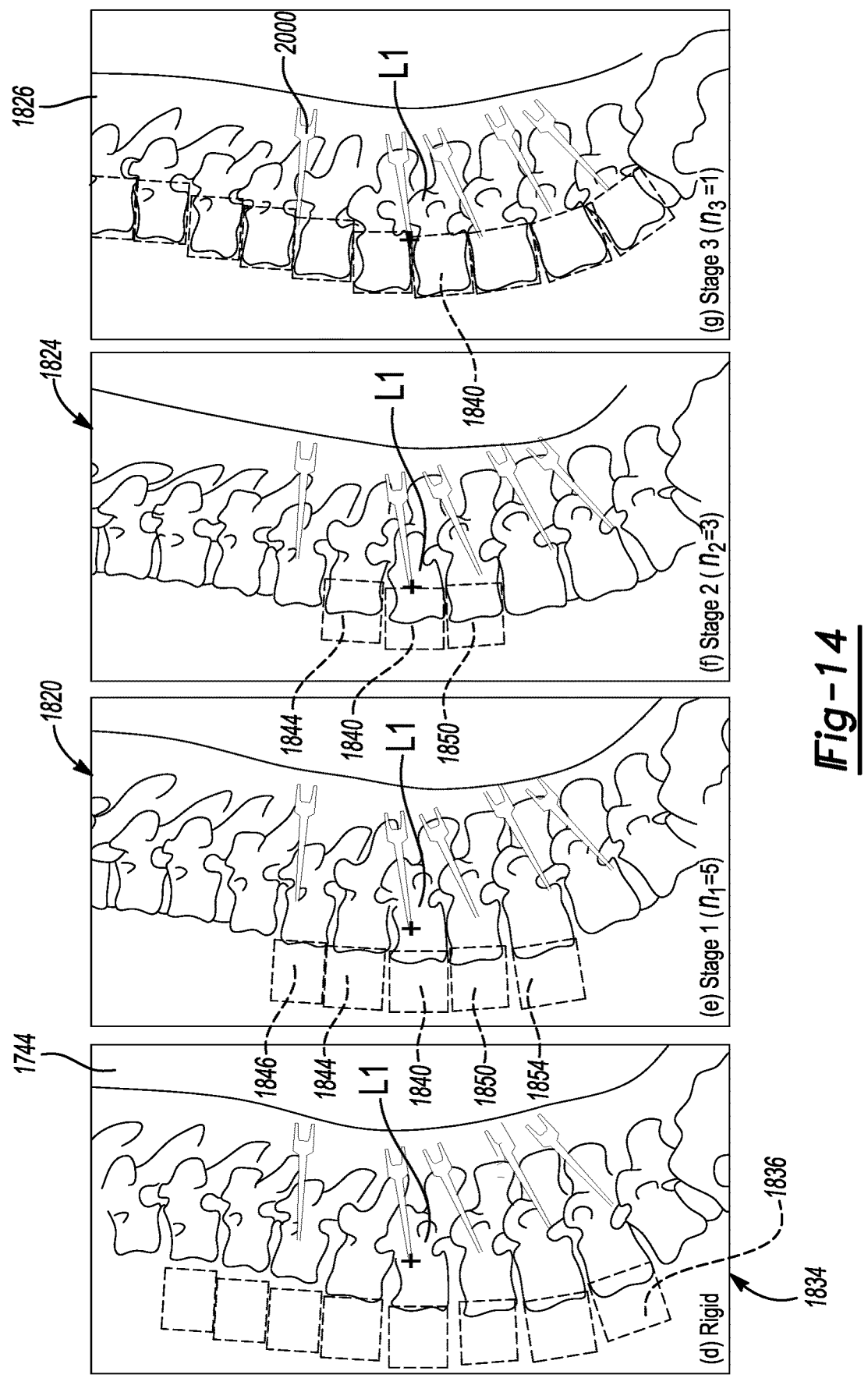
FIG. 14 is a graphical illustration of the process of FIG. 13.

The transformation of the target vertebrae 1840 to the target image data may be illustrated at 1826 in FIG. 14 and includes a mask that surrounds or includes the single target vertebrae 1840. The single target vertebrae may be registered to the current image data 1744 by a transformation 1940. The transformation 1940 includes information regarding the transformation of the single target vertebrae 1840 from the pre-operative image data 1740 to the current image data 1744. As illustrated in FIG. 14, the process 1760 may be carried out for each of the identified vertebrae in the pre-operative image data 1740 to allow for transformation of each of the individual vertebra to the current image data 1744. Thus, the transformation step 1826 may occur for each of the vertebrae in the field of view of the pre-operative image data 1740 to register it to elements in the current image data 1744.

As noted above, the masking process 1760 allows for a transformation of an individual vertebra even though a deformation (i.e., a change in relative position of a registered element) has occurred between the preoperative image data 1740 and a current image data 1744. As illustrated in FIG. 14, in the rigid registration 1834, the pre-operative image data may include a registration mismatch relative to the current image data 1744 as deformation is not accounted. Therefore, the deformation may be accounted for by the multi-mask process 1760.

Moreover, an efficiency may be included by increasing a resolution of the respective image data, including the pre-operative image data 1740 and the current image data 1744 between each of the sets 1820, 1824, 1826. That is the first registration step 1820 include a more coarse or less resolution relative to the final step 1826. This may reduce computational time and minimize finding of local minima to enhance the registration of the target vertebrae. Further, it is understood that the target vertebrae may be identified in a plurality of the masking processes 1760 for each selected vertebra, which may include all of the vertebrae in the field of the pre-operative image 1740 and/or the current image data 1744.

The registration procedure 1700, as illustrated in FIG. 12 and discussed above, may register the pre-operative image data 1740 to current image data 1744, as also discussed above, and exemplary illustrated in FIG. 14. Further, devices present in the current image data may also be registered, that is identified in the current image data 1744 and registered to the pre-operative image data, in part 1720 of the registration 1700. An exemplary illustrated device may include a medical screw 2000, illustrated in the targeted vertebra 1840 in FIG. 14. Various pre-known or pre-determined information regarding the device 2000 may also be used in the registration and proper illustration of a pose of the device 2000 relative to the pre-operative image data 1740. This may assist in confirming and/or identifying a procedure relative to the subject 28.

With continuing reference to FIG. 12 and additional reference to FIG. 15, the device registration to the image data, including the registered pre-operative image data 1740 may occur with and/or subsequently to the registration of the pre-operative image data 1740 to the current image data 1744. As discussed above, the current image data may be acquired during an operative procedure which may include the placement of various instruments, such as the medical screw 2000. The device registration portion 1720 of the registration 1700 may include an input of the current image data 1744 which may include image data of the devices, such as the medical screw 2000 and input of the transform or registered pre-operative image data, according to the procedure 1710 as discussed above. The input in the device registration 1720 may include the current image data and the registered image data to an optimization procedure 2010 which may be similar to the optimization procedure as discussed above. Generally, the optimization is a gradient correlation (GC) based upon known parameters also referred to as known components (KC) of the device.

The device registration 1720 further includes an input of a device model 2020. The device model 2020 may include known components of the device, such as the medical screw 2000. The known components may be based upon the parameters of the device, such as known dimensions, materials, range of relative motion (e.g., a pedal screwhead relative to a shank), etc. In various embodiments, for example, the device 2000 may include the device model 2020 that includes 10° of freedom of movement of the pedal head relative to the change and this may included in the known components. Others may include six degrees of freedom of position for a screw shaft, three degrees of freedom of position for rotation of a tulip head relative to the screw shaft, and one degrees of freedom of position for translational offset between the tulip head and the shaft. Known components may be determined or evaluated according to various techniques such as that disclosed in U.S. Pat. No. 11,138,768, incorporated herein by a reference. Further, determination of known components and various degrees of freedom thereof may also include that disclosed in Uneri, A., De Silva, T., Stayman, J. W., Kleinszig, G., Vogt, S., Khanna, A. J., Gokaslan, Z. L., Wolinsky, J. P. and Siewerdsen, J. H., "Known-component 3D-2D registration for quality assurance of spine surgery pedicle screw placement," Phys. Med. Biol. 60(20), 8007-8024 (2015), incorporated herein by reference.

The device model 2020 may be used to create or generate synthetic projections equivalent to the synthetic slot images 1770, 1774. Synthetic images may be synthetic device slot images 2030. The model may be projected or a projection of the model may be made with projection 2034 to generate the synthetic device slot images. The synthetic device slot images may also, therefore, be AP and LAT. The synthetic device slot images may then be optimized in the optimized process 2010 including generation of additional or altered slot images in the iteration process 2038. Accordingly, once the device model is determined, which may be input from a memory system, entered by a user, or otherwise accessed by a processor to form a projection to form the synthetic device slot images 2030 and then optimized through an iterative process of altering the projections to achieve a similarity, such as a gradient correlation, to the devices in the current image data. Once the optimization is achieved a transformation 2050 may be output to translate or transform the position of the device, such as the medical screw 2000, to the pre-operative image data.

Figure 15:
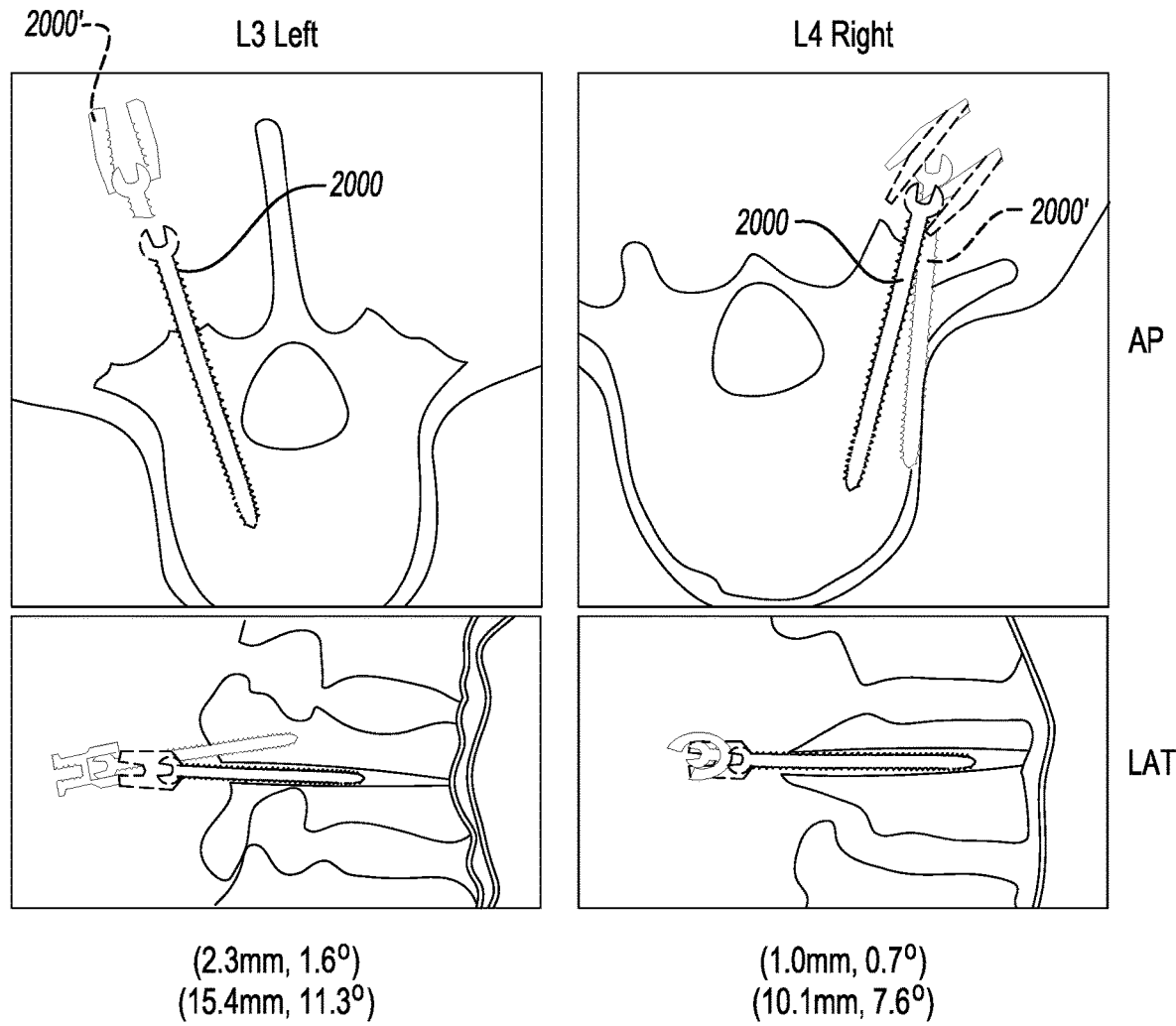
FIG. 15 is an exemplary illustration of a result of the registration process of FIG. 12.

With continuing reference to FIG. 12 and with additional reference to FIG. 15, an exemplary registration with and without the multi-scale transformation is illustrated. As illustrated in FIG. 15, for example, a multi-scale registration 1700 is shown in solid lines and a rigid transformation is shown in solid lines. Each of the columns illustrate a respective vertebra, such as in L3 vertebra and a L4 vertebra and the top row illustrates AP images and the bottom row illustrates lateral images. As illustrated in FIG. 15, the registered position with the multi-scale transformation according to the registration 1720 discussed above, differs from that of the rigid process transformation. The study performed found that the multi-scale transformation due to the device registration 1720 was more accurate to a confirmed position of the implanted device than the rigid transformation. As illustrated in the L3 AP view, the multi-scale registration illustrates the device 2000 far deeper into the vertebrae than the rigid transformation device 2000'. Similarly, in the AP view of the L4 vertebra the multi-scale transformation of the device 2000 is illustrated completely within the vertebra while the rigid transformation of the device 2000' is illustrated to have pierced the vertebra. Accordingly, the multi-scale registration 1720 more accurately illustrates the confirmed and determined position of the device 2000 in the subject 28.

The current image data may not precisely illustrate the position of the device 2000 in the subject due to various interferences such as metallic interference, or other interference. Accordingly, the device registration 1720 including known components of the device from the device model 2020 assists in determining a registration of the device 2000 with a selected accuracy.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of detecting and classifying a feature in a plurality of individual image projections generated with an imaging system, the method comprising:
   acquiring a first plurality of individual image projections as a plurality of input images of a first view of a subject;
   acquiring a second plurality of individual image projections as a plurality of input images of a second view of the subject;
   determining in at least a first sub-plurality of the acquired first plurality of individual image projections whether the feature is in each image projection of the first sub-plurality of image projections of the acquired plurality of individual image projections;
   determining in at least a second sub-plurality of the acquired second plurality of individual image projections whether the feature is in each image projection of the second sub-plurality of image projections of the acquired plurality of individual image projections;
   concatenating a feature map of the first sub-plurality of the acquired first plurality of individual image projections;
   concatenating a feature map of the second sub-plurality of the acquired second plurality of individual image projections;
   pairing region proposals in the first sub-plurality of the acquired first plurality of individual image projections with the second sub-plurality of the acquired second plurality of individual image projections using regression and classification;

performing a convolutional neural-network classification of the paired region proposals;

outputting a determination of the position of the feature in each image projection; and display on a display device the outputted position of the determined feature and the determined feature using the plurality of individual image projections of the subject;

wherein displaying the determined feature allow for confirmation, selection, identification, or planning of a procedure.

2. The method of claim 1, wherein the first view is different than the second view.

3. The method of claim 2, wherein the first view is a lateral view and the second view is an anterior-to-posterior view.

4. The method of claim 2, wherein the determination process is a machine learning algorithm operable to recognize the feature in the input image.

5. The method of claim 2, wherein acquiring each of the first and second plurality of individual image projections includes acquiring a set of individual slot image projections is acquired of a subject with an imaging head at a selected position relative to the subject;

wherein a filter including a plurality of slots causes the acquisition of the set of individual slot image projections simultaneously;

wherein each individual slot image projection of the set of individual slot image projections has a unique perspective of the subject relative to each other individual slot image projection.

6. The method of claim 5, wherein the first plurality of individual image projections is acquired with the slot filter at an anterior-to-posterior perspective relative to the subject;

wherein the second plurality of individual image projections is acquired with the slot filter at lateral perspective relative to the subject.

7. The method of claim 6, wherein acquiring each of the first and second plurality of individual image projections comprises:

providing instructions to the imaging system to move the imaging head to a plurality of positions relative to the subject; and projecting x-rays through the subject to a detector to generate the plurality of the sets of individual slot image projections.

8. The method of claim 2, further comprising:

combining the first plurality of individual image projections by stitching together selected individual slot image projections of the acquired plurality of the sets of individual slot image projections to generate a first combined image of the subject; and combining the second plurality of individual image projections by stitching together selected individual slot image projections of the acquired plurality of the sets of individual slot image projections to generate a second combined image of the subject;

wherein outputting the determination of the position of the feature in each image projection includes labeling at least one of the first combined image or the second combined image.

9. The method of claim 8, further comprising:

confirming an order of the classified regions in at least one of the first combined image or the second combined image.

10. The method of claim 2, further comprising:

adjusting weights in layers of a convolutional machine learning system for the determination in at least the first sub-plurality of the acquired first plurality of individual image projections whether the feature is in each image projection of the first sub-plurality of image projections of the acquired plurality of individual image projections and the determination in at least the second sub-plurality of the acquired second plurality of individual image projections whether the feature is in each image projection of the second sub-plurality of image projections of the acquired plurality of individual image projections.

11. A system operable to detect and classify a feature in a plurality of individual image projections generated with an imaging system, comprising:

a processor module configured to execute instructions to:

acquire a first plurality of individual image projections as a plurality of input images of a first view of a subject;

acquire a second plurality of individual image projections as a plurality of input images of a second view of the subject;

determine in at least a first sub-plurality of the acquired first plurality of individual image projections whether the feature is in each image projection of the first sub-plurality of image projections of the acquired plurality of individual image projections;

determine in at least a second sub-plurality of the acquired second plurality of individual image projections whether the feature is in each image projection of the second sub-plurality of image projections of the acquired plurality of individual image projections;

concatenate a feature map of the first sub-plurality of the acquired first plurality of individual image projections;

concatenate a feature map of the second sub-plurality of the acquired second plurality of individual image projections;

pair region proposals in the first sub-plurality of the acquired first plurality of individual image projections with the second sub-plurality of the acquired second plurality of individual image projections using regression and classification;

perform a convolutional neural-network classification of the paired region proposals;

output a determination of the position of the feature in each image projection; and display on a display device the outputted position of the determined feature and the determined feature using the plurality of individual image projections of the subject;

wherein displaying the determined feature allow for confirmation, selection, identification, or planning of a procedure.

12. The system of claim 11, wherein the first view is acquired at a different than the second view relative to the subject.

13. The system of claim 12, wherein the first view is a lateral view of the subject and the second view is an anterior-to-posterior view of the subject.

14. The system of claim 12, wherein the processor module configured to execute instructions includes a machine learning algorithm operable to recognize the feature in the input image.

15. The system of claim 12, wherein the processor module configured to execute instructions further includes instructions to:

acquire each of the first and second plurality of individual image projections includes acquiring a set of individual slot image projections is acquired of a subject with an imaging head at a selected position relative to the subject;

wherein a filter including a plurality of slots causes the acquisition of the set of individual slot image projections simultaneously;

wherein each individual slot image projection of the set of individual slot image projections has a unique perspective of the subject relative to each other individual slot image projection.

16. The system of claim 15, wherein the first plurality of individual image projections is acquired with the slot filter at an anterior-to-posterior perspective relative to the subject;

wherein the second plurality of individual image projections is acquired with the slot filter at lateral perspective relative to the subject.

17. The system of claim 16, wherein acquiring each of the first and second plurality of individual image projections comprises:

executing instructions to move an imaging head to a plurality of positions relative to the subject; and project x-rays through the subject to a detector to generate the plurality of the sets of individual slot image projections.

18. The system of claim 12, wherein the processor module is further operable to execute instructions to:

combine the first plurality of individual image projections by stitching together selected individual slot image projections of the acquired plurality of the sets of individual slot image projections to generate a first combined image of the subject; and combine the second plurality of individual image projections by stitching together selected individual slot image projections of the acquired plurality of the sets of individual slot image projections to generate a second combined image of the subject;

wherein outputting the determination of the position of the feature in each image projection includes labeling at least one of the first combined image or the second combined image.

19. The system of claim 18, wherein the processor module is further operable to execute instructions to:

confirm an order of the classified regions in at least one of the first combined image or the second combined image.

20. The system of claim 12, wherein the processor module is further operable to execute instructions to:

adjust weights in layers of a convolutional machine learning system for the determination in at least the first sub-plurality of the acquired first plurality of individual image projections whether the feature is in each image projection of the first sub-plurality of image projections of the acquired plurality of individual image projections and the determination in at least the second sub-plurality of the acquired second plurality of individual image projections whether the feature is in each image projection of the second sub-plurality of image projections of the acquired plurality of individual image projections.

* * * * *